United States Patent
Zabar et al.

(10) Patent No.: US 12,038,322 B2
(45) Date of Patent: Jul. 16, 2024

(54) DEVICES AND METHODS FOR TESTING ABLATION SYSTEMS

(71) Applicant: Eximo Medical Ltd., Rehovot (IL)

(72) Inventors: Yoel Zabar, Nes Ziona (IL); Ilan Ben Oren, Modiin (IL); Oren Meshulam Stern, Shilo (IL); Yonatan Romm, Efrat (IL)

(73) Assignee: EXIMO MEDICAL LTD., Rehovot (IL)

( * ) Notice: Subject to any disclaimer, the term of this patent is extended or adjusted under 35 U.S.C. 154(b) by 0 days.

(21) Appl. No.: 18/339,052

(22) Filed: Jun. 21, 2023

(65) Prior Publication Data
US 2023/0408329 A1 Dec. 21, 2023

Related U.S. Application Data

(60) Provisional application No. 63/354,081, filed on Jun. 21, 2022.

(51) Int. Cl.
*G01J 1/42* (2006.01)
*A61B 18/20* (2006.01)

(52) U.S. Cl.
CPC ............. *G01J 1/4257* (2013.01); *A61B 18/20* (2013.01)

(58) Field of Classification Search
CPC . A61B 18/20; A61B 18/22; A61B 2018/2015; A61B 2018/202;
(Continued)

(56) References Cited

U.S. PATENT DOCUMENTS

| 1,706,161 | A | 3/1929 | Hollnagel |
| 2,699,770 | A | 1/1955 | Fourestier |

(Continued)

FOREIGN PATENT DOCUMENTS

| CA | 1326800 | 2/1994 |
| CA | 3017252 C | 12/2019 |

(Continued)

OTHER PUBLICATIONS

Pace, E., et al, Fast Stable Visible-blind and Highly Sensitive CVD Diamond UV Photo Detectors for Laboratory and Space Applications, Diamond and Related Materials, vol. 9, Issues 3-6 (Apr.-May 2000) pp. 987-993.

(Continued)

*Primary Examiner* — John R Lee
(74) *Attorney, Agent, or Firm* — Kevin P. Radigan, Esq.; Heslin Rothenberg Farley & Mesiti P.C.

(57) ABSTRACT

A system for testing an ablation system comprising an optical box and a catheter connector is disclosed. The system comprises a qualitative beam assessment device, a quantitative beam assessment device, and a processor. The qualitative beam assessment device has a camera configured to record signals related to a beam profile of a beam emitted by the optical box. The quantitative beam assessment device has an energy sensor configured to measure a beam energy of the beam. The processor is configured to receive the signals from the beam assessment devices, determine a qualitative condition of the beam based on the beam profile signals, and determine a quantitative condition of the beam based on the beam energy signals.

20 Claims, 25 Drawing Sheets

(58) Field of Classification Search
CPC .... A61B 2018/2023; A61B 2018/2035; A61B 2018/204; A61B 2018/2045; A61B 2018/205; A61B 2018/2055; G01J 1/42; G01J 1/4257; H01S 3/00; H01S 3/0007; H01S 3/0014
See application file for complete search history.

(56) References Cited

U.S. PATENT DOCUMENTS

| | | | |
|---|---|---|---|
| 3,043,910 A | 7/1962 | Hicks, Jr. | |
| 3,051,035 A | 8/1962 | Root | |
| 3,051,166 A | 8/1962 | Hrair | |
| 3,068,742 A | 12/1962 | Hicks, Jr. | |
| 3,423,581 A | 1/1969 | Baer | |
| 3,455,625 A | 7/1969 | Brumley | |
| 3,572,325 A | 3/1971 | Bazell | |
| 3,605,750 A | 9/1971 | Sheridan | |
| 3,622,743 A | 11/1971 | Muncheryan | |
| 3,641,332 A | 2/1972 | Reick | |
| 3,643,653 A | 2/1972 | Takahashi | |
| 3,678,741 A | 7/1972 | Burley | |
| 3,704,996 A | 12/1972 | Borner | |
| 3,710,798 A | 1/1973 | Bredemeier | |
| 3,726,272 A | 4/1973 | Mori | |
| 3,756,688 A | 9/1973 | Hudson | |
| 3,768,146 A | 10/1973 | Braun | |
| 3,780,295 A | 12/1973 | Kapron | |
| 3,790,791 A | 2/1974 | Anderson | |
| 3,796,905 A | 3/1974 | Maeda | |
| 3,802,440 A | 4/1974 | Ziegler | |
| 3,808,549 A | 4/1974 | Maurer | |
| 3,832,028 A | 8/1974 | Kapron | |
| 3,834,391 A | 9/1974 | Block | |
| 3,834,803 A | 9/1974 | Tsukada | |
| 3,843,865 A | 10/1974 | Nath | |
| 3,846,010 A | 11/1974 | Love | |
| 3,849,947 A | 11/1974 | Bunkoczy | |
| 3,858,577 A | 1/1975 | Bass | |
| 3,861,781 A | 1/1975 | Hasegawa | |
| 3,866,599 A | 2/1975 | Johnson | |
| 3,874,783 A | 4/1975 | Cole | |
| 3,880,452 A | 4/1975 | Fields | |
| 3,906,221 A | 9/1975 | Mercier | |
| 3,910,677 A | 10/1975 | Becker | |
| 3,920,980 A | 11/1975 | Nath | |
| 3,932,184 A | 1/1976 | Cohen | |
| 3,972,585 A | 8/1976 | Dalgleish | |
| 4,005,522 A | 2/1977 | Dalgleish | |
| 4,008,948 A | 2/1977 | Dalgleish | |
| 4,087,158 A | 5/1978 | Lewis | |
| 4,148,554 A | 4/1979 | Magnusson | |
| 4,191,446 A | 3/1980 | Arditty | |
| 4,233,493 A | 11/1980 | Nath | |
| 4,273,109 A | 6/1981 | Enderby | |
| 4,273,127 A | 6/1981 | Auth | |
| 4,313,431 A | 2/1982 | Frank | |
| 4,380,365 A | 4/1983 | Gross | |
| 4,449,535 A | 5/1984 | Renault | |
| 4,564,011 A | 1/1986 | Goldman | |
| 4,573,761 A | 3/1986 | McLachlan | |
| 4,578,061 A | 3/1986 | Lemelson | |
| 4,592,353 A | 6/1986 | Daikuzono | |
| 4,641,912 A * | 2/1987 | Goldenberg | A61B 18/245 606/7 |
| 4,654,532 A | 3/1987 | Hirschfeld | |
| 4,660,925 A | 4/1987 | McCaughan, Jr. | |
| 4,662,368 A | 5/1987 | Hussein | |
| 4,666,426 A | 5/1987 | Aigner | |
| 4,671,273 A | 6/1987 | Lindsey | |
| 4,672,961 A | 6/1987 | Davies | |
| 4,693,244 A | 9/1987 | Daikuzono | |
| 4,693,556 A | 9/1987 | McCaughan, Jr. | |
| 4,695,697 A | 9/1987 | Kosa | |
| 4,697,595 A | 10/1987 | Breyer | |
| 4,707,134 A | 11/1987 | McLachlan | |
| 4,729,763 A | 3/1988 | Henrie | |
| 4,732,448 A * | 3/1988 | Goldenberg | G02B 6/06 606/7 |
| 4,736,743 A | 4/1988 | Daikuzono | |
| 4,740,047 A | 4/1988 | Abe | |
| 4,743,084 A | 5/1988 | Manning | |
| 4,773,413 A | 9/1988 | Hussein | |
| 4,800,876 A | 1/1989 | Fox | |
| 4,802,650 A | 2/1989 | Stricker | |
| 4,812,003 A | 3/1989 | Dambach | |
| 4,816,670 A | 3/1989 | Kitamura | |
| 4,817,601 A | 4/1989 | Roth | |
| 4,830,460 A | 5/1989 | Goldenberg | |
| 4,832,024 A | 5/1989 | Boussignac | |
| 4,834,493 A | 5/1989 | Cahill | |
| 4,844,062 A | 7/1989 | Wells | |
| 4,862,887 A | 9/1989 | Weber | |
| 4,889,129 A | 12/1989 | Dougherty | |
| 4,919,508 A | 4/1990 | Grace | |
| 4,955,882 A | 9/1990 | Hakky | |
| 4,966,596 A | 10/1990 | Kuntz | |
| 4,968,306 A | 11/1990 | Huss | |
| 4,968,314 A | 11/1990 | Michaels | |
| 4,975,925 A | 12/1990 | Derrickson | |
| 4,979,797 A | 12/1990 | Nemeth | |
| 4,979,939 A | 12/1990 | Shiber | |
| 4,985,029 A | 1/1991 | Hoshino | |
| 4,988,163 A | 1/1991 | Cohen | |
| 4,993,412 A | 2/1991 | Murphy-Chutorian | |
| 4,995,691 A | 2/1991 | Purcell, Jr. | |
| 4,998,794 A | 3/1991 | Holzman | |
| 5,011,254 A | 4/1991 | Edwards | |
| 5,011,279 A | 4/1991 | Auweter | |
| 5,016,964 A | 5/1991 | Donnelly | |
| 5,026,366 A | 6/1991 | Leckrone | |
| 5,029,588 A | 7/1991 | Yock | |
| 5,030,201 A | 7/1991 | Palestrant | |
| 5,037,180 A | 8/1991 | Stone | |
| 5,037,421 A | 8/1991 | Boutacoff | |
| 5,041,109 A | 8/1991 | Abela | |
| 5,042,980 A | 8/1991 | Baker | |
| 5,053,033 A | 10/1991 | Clarke | |
| 5,060,557 A | 10/1991 | Dunn | |
| 5,074,632 A | 12/1991 | Potter | |
| 5,093,877 A | 3/1992 | Aita | |
| 5,100,507 A | 3/1992 | Cholewa | |
| 5,112,127 A | 5/1992 | Carrabba | |
| 5,129,896 A | 7/1992 | Hasson | |
| 5,135,531 A | 8/1992 | Shiber | |
| 5,146,917 A | 9/1992 | Wagnieres | |
| 5,147,353 A | 9/1992 | Everett | |
| 5,147,354 A | 9/1992 | Boutacoff | |
| 5,151,096 A | 9/1992 | Khoury | |
| 5,152,744 A | 10/1992 | Krause | |
| 5,154,708 A | 10/1992 | Long | |
| 5,157,750 A | 10/1992 | Grace | |
| 5,164,945 A | 11/1992 | Long | |
| 5,166,756 A | 11/1992 | McGee | |
| 5,188,632 A | 2/1993 | Goldenberg | |
| 5,188,635 A | 2/1993 | Radtke | |
| 5,190,536 A | 3/1993 | Wood | |
| 5,193,526 A | 3/1993 | Daikuzono | |
| 5,196,004 A | 3/1993 | Sinofsky | |
| 5,196,005 A | 3/1993 | Doiron | |
| 5,207,669 A | 5/1993 | Baker | |
| 5,222,966 A | 6/1993 | Perkins | |
| 5,250,045 A | 10/1993 | Bohley | |
| 5,253,312 A | 10/1993 | Payne | |
| 5,254,114 A | 10/1993 | Reed, Jr. | |
| 5,263,951 A | 11/1993 | Spears | |
| 5,263,952 A | 11/1993 | Grace | |
| 5,267,979 A | 12/1993 | Appling | |
| 5,267,993 A | 12/1993 | Grace | |
| 5,267,995 A | 12/1993 | Doiron | |
| 5,269,777 A | 12/1993 | Doiron | |
| 5,275,622 A | 1/1994 | Lazarus | |
| 5,290,275 A | 3/1994 | Kittrell | |
| 5,292,311 A | 3/1994 | Cope | |
| 5,292,320 A | 3/1994 | Brown | |

(56) References Cited

U.S. PATENT DOCUMENTS

| | | |
|---|---|---|
| 5,293,872 A | 3/1994 | Alfano |
| 5,300,066 A | 4/1994 | Manoukian |
| 5,306,274 A | 4/1994 | Long |
| 5,312,396 A | 5/1994 | Feld |
| 5,312,399 A | 5/1994 | Hakky |
| 5,315,614 A | 5/1994 | Grace |
| 5,321,783 A | 6/1994 | Nielson |
| 5,330,465 A | 7/1994 | Doiron |
| 5,342,383 A | 8/1994 | Thomas |
| 5,343,543 A | 8/1994 | Novak, Jr. |
| 5,346,488 A | 9/1994 | Prince |
| 5,349,590 A | 9/1994 | Amirkhanian |
| 5,350,377 A | 9/1994 | Winston |
| 5,352,221 A | 10/1994 | Fumich |
| 5,354,294 A | 10/1994 | Chou |
| 5,360,416 A | 11/1994 | Ausherman |
| 5,370,649 A | 12/1994 | Gardetto |
| 5,377,683 A | 1/1995 | Barken |
| 5,383,199 A | 1/1995 | Laudenslager |
| 5,395,361 A | 3/1995 | Fox |
| 5,400,428 A | 3/1995 | Grace |
| 5,401,270 A | 3/1995 | Mueller |
| 5,402,508 A | 3/1995 | O'Rourke |
| 5,404,218 A | 4/1995 | Nave |
| 5,415,633 A | 5/1995 | Lazarus |
| 5,415,653 A | 5/1995 | Wardle |
| 5,415,655 A | 5/1995 | Fuller |
| 5,419,312 A | 5/1995 | Arenberg |
| 5,421,928 A | 6/1995 | Knecht |
| 5,423,806 A | 6/1995 | Dale |
| 5,425,723 A | 6/1995 | Wang |
| 5,428,699 A | 6/1995 | Pon |
| 5,429,604 A | 7/1995 | Hammersmark |
| 5,429,617 A | 7/1995 | Hammersmark |
| 5,432,880 A | 7/1995 | Diner |
| 5,445,608 A | 8/1995 | Chen |
| 5,456,680 A | 10/1995 | Taylor |
| 5,464,395 A | 11/1995 | Faxon |
| 5,466,234 A | 11/1995 | Loeb |
| 5,470,330 A | 11/1995 | Goldenberg |
| 5,484,433 A | 1/1996 | Taylor |
| 5,486,170 A | 1/1996 | Winston |
| 5,495,541 A | 2/1996 | Murray |
| 5,498,258 A | 3/1996 | Hakky |
| 5,499,975 A | 3/1996 | Cope |
| 5,509,917 A | 4/1996 | Cecchetti |
| 5,514,128 A | 5/1996 | Hillsman |
| 5,534,000 A | 7/1996 | Bruce |
| 5,536,248 A | 7/1996 | Weaver |
| 5,536,265 A | 7/1996 | Van den Bergh |
| 5,562,657 A | 10/1996 | Griffin |
| 5,571,098 A | 11/1996 | Domankevitz |
| 5,624,026 A | 4/1997 | Chernoff |
| 5,631,986 A | 5/1997 | Frey |
| 5,643,251 A | 7/1997 | Hillsman |
| 5,643,253 A | 7/1997 | Baxter |
| 5,643,257 A | 7/1997 | Cohen |
| 5,653,696 A | 8/1997 | Shiber |
| 5,662,646 A | 9/1997 | Fumich |
| 5,688,263 A | 11/1997 | Hauptmann |
| 5,693,029 A | 12/1997 | Leonhardt |
| 5,693,043 A | 12/1997 | Kittrell |
| 5,695,482 A | 12/1997 | Kaldany |
| 5,695,583 A | 12/1997 | Van den Bergh |
| 5,700,243 A | 12/1997 | Narciso, Jr. |
| 5,710,626 A | 1/1998 | O'Rourke |
| 5,717,807 A | 2/1998 | Theroux |
| 5,720,894 A | 2/1998 | Perry |
| 5,725,521 A | 3/1998 | Mueller |
| 5,728,091 A | 3/1998 | Payne |
| 5,754,717 A | 5/1998 | Esch |
| 5,764,840 A | 6/1998 | Wach |
| 5,769,868 A | 6/1998 | Yock |
| 5,782,797 A | 7/1998 | Schweich, Jr. |
| 5,807,389 A | 9/1998 | Gardetto |
| 5,810,662 A | 9/1998 | Van Becelaere |
| 5,817,144 A | 10/1998 | Gregory |
| 5,836,940 A | 11/1998 | Gregory |
| 5,836,946 A | 11/1998 | Diaz |
| 5,843,073 A | 12/1998 | Sinofsky |
| 5,868,734 A | 2/1999 | Soufiane |
| 5,878,178 A | 3/1999 | Wach |
| 5,897,551 A | 4/1999 | Everett |
| 5,908,415 A | 6/1999 | Sinofsky |
| 5,916,210 A | 6/1999 | Winston |
| 5,947,959 A | 9/1999 | Sinofsky |
| 5,951,482 A | 9/1999 | Winston |
| 5,951,543 A | 9/1999 | Brauer |
| 5,976,124 A | 11/1999 | Reiser |
| 5,989,243 A | 11/1999 | Goldenberg |
| 5,991,404 A | 11/1999 | Brahami |
| 6,013,072 A | 1/2000 | Winston et al. |
| 6,027,450 A | 2/2000 | Brown |
| 6,033,398 A | 3/2000 | Farley |
| 6,048,349 A | 4/2000 | Winston |
| 6,053,809 A | 4/2000 | Arceneaux |
| 6,056,743 A | 5/2000 | Ellis |
| 6,063,093 A | 5/2000 | Winston |
| 6,096,011 A | 8/2000 | Trombley, III |
| 6,102,905 A | 8/2000 | Baxter |
| 6,106,515 A | 8/2000 | Winston |
| 6,117,125 A | 9/2000 | Rothbarth |
| 6,126,654 A | 10/2000 | Giba |
| 6,139,543 A | 10/2000 | Esch |
| 6,152,919 A | 11/2000 | Hakky |
| 6,162,214 A | 12/2000 | Mueller |
| 6,164,280 A | 12/2000 | Everett |
| 6,179,808 B1 | 1/2001 | Boukhny |
| 6,193,676 B1 | 2/2001 | Winston |
| 6,206,898 B1 | 3/2001 | Honeycutt |
| 6,210,400 B1 | 4/2001 | Hebert |
| 6,228,076 B1 | 5/2001 | Winston |
| 6,251,100 B1 | 6/2001 | Flock |
| 6,258,084 B1 | 7/2001 | Goldman |
| 6,263,236 B1 | 7/2001 | Kasinkas |
| 6,270,492 B1 | 8/2001 | Sinofsky |
| 6,270,495 B1 | 8/2001 | Palermo |
| 6,283,951 B1 | 9/2001 | Flaherty |
| 6,302,875 B1 | 10/2001 | Makower |
| 6,344,048 B1 | 2/2002 | Chin |
| 6,352,549 B1 | 3/2002 | Everett |
| 6,375,651 B2 | 4/2002 | Grasso, III |
| 6,394,976 B1 | 5/2002 | Winston |
| 6,398,777 B1 | 6/2002 | Navarro |
| 6,439,944 B1 | 8/2002 | La Fata |
| 6,440,125 B1 | 8/2002 | Rentrop |
| 6,447,477 B2 | 9/2002 | Burney |
| 6,451,010 B1 | 9/2002 | Angeley |
| 6,454,790 B1 | 9/2002 | Neuberger |
| 6,463,313 B1 | 10/2002 | Winston |
| 6,485,485 B1 | 11/2002 | Winston |
| 6,514,217 B1 | 2/2003 | Selmon |
| 6,522,806 B1 | 2/2003 | James, IV |
| 6,539,944 B1 | 4/2003 | Watson |
| 6,544,230 B1 | 4/2003 | Flaherty |
| 6,547,757 B1 | 4/2003 | Kranz |
| 6,547,779 B2 | 4/2003 | Levine |
| 6,551,302 B1 | 4/2003 | Rosinko |
| 6,554,824 B2 | 4/2003 | Davenport |
| 6,555,827 B1 | 4/2003 | Kockott |
| 6,561,998 B1 | 5/2003 | Roth |
| 6,599,277 B2 | 7/2003 | Neubert |
| 6,611,720 B2 | 8/2003 | Hata |
| 6,628,519 B2 | 9/2003 | Umetsu |
| 6,652,803 B2 | 11/2003 | Watanabe |
| 6,663,621 B1 | 12/2003 | Winston |
| 6,673,064 B1 | 1/2004 | Rentrop |
| 6,673,065 B1 | 1/2004 | Veligdan |
| 6,685,648 B2 | 2/2004 | Flaherty |
| 6,692,466 B1 | 2/2004 | Chow |
| 6,701,044 B2 | 3/2004 | Arbore |
| 6,716,210 B2 | 4/2004 | Lin |
| 6,746,422 B1 | 6/2004 | Noriega |
| 6,752,800 B1 | 6/2004 | Winston |

(56) References Cited

U.S. PATENT DOCUMENTS

| | | |
|---|---|---|
| 6,752,803 B2 | 6/2004 | Goldman |
| 6,767,338 B2 | 7/2004 | Hawk |
| 6,769,433 B2 | 8/2004 | Zikorus |
| 6,772,014 B2 | 8/2004 | Coe |
| 6,775,447 B2 | 8/2004 | Nicholson |
| 6,796,710 B2 | 9/2004 | Yates |
| 6,842,639 B1 | 1/2005 | Winston |
| 6,845,193 B2 | 1/2005 | Loeb |
| 6,852,109 B2 | 2/2005 | Winston |
| 6,926,692 B2 | 8/2005 | Katoh |
| 6,951,554 B2 | 10/2005 | Johansen |
| 6,962,584 B1 | 11/2005 | Stone |
| 6,962,585 B2 | 11/2005 | Poleo, Jr. |
| 6,967,767 B2 | 11/2005 | Nicholson |
| 6,970,732 B2 | 11/2005 | Winston |
| 6,978,783 B2 | 12/2005 | Svendsen |
| 6,986,764 B2 | 1/2006 | Davenport |
| 6,986,766 B2 | 1/2006 | Caldera |
| 6,989,004 B2 | 1/2006 | Hinchliffe |
| 7,050,692 B2 | 5/2006 | Harlan |
| 7,059,330 B1 | 6/2006 | Makower |
| 7,063,610 B2 | 6/2006 | Mysker |
| 7,063,695 B2 | 6/2006 | Nield |
| 7,128,735 B2 | 10/2006 | Weston |
| 7,141,041 B2 | 11/2006 | Seward |
| 7,163,535 B2 | 1/2007 | Ryba |
| 7,167,622 B2 | 1/2007 | Temelkuran |
| 7,172,576 B2 | 2/2007 | Sawa |
| 7,186,252 B2 | 3/2007 | Nobis |
| 7,247,162 B1 | 7/2007 | Thornton |
| 7,257,302 B2 | 8/2007 | Fermann |
| 7,267,674 B2 | 9/2007 | Brucker |
| 7,273,469 B1 | 9/2007 | Chan |
| 7,273,478 B2 | 9/2007 | Appling |
| 7,284,981 B2 | 10/2007 | Schmid |
| 7,288,087 B2 | 10/2007 | Winston |
| 7,303,533 B2 | 12/2007 | Johansen |
| 7,331,954 B2 | 2/2008 | Temelkuran |
| 7,357,797 B2 | 4/2008 | Ryba |
| 7,377,910 B2 | 5/2008 | Katoh |
| 7,379,648 B1 | 5/2008 | Brooks |
| 7,381,200 B2 | 6/2008 | Katoh |
| 7,391,561 B2 | 6/2008 | Di Teodoro |
| 7,412,132 B1 | 8/2008 | Liu |
| 7,430,352 B2 | 9/2008 | Di Teodoro |
| 7,450,618 B2 | 11/2008 | Dantus |
| 7,458,967 B2 | 12/2008 | Appling |
| 7,479,147 B2 | 1/2009 | Honeycutt |
| 7,483,204 B2 | 1/2009 | Harter |
| 7,499,756 B2 | 3/2009 | Bowe |
| 7,503,914 B2 | 3/2009 | Coleman |
| 7,513,886 B2 | 4/2009 | Konstantino |
| 7,519,253 B2 | 4/2009 | Islam |
| 7,524,289 B2 | 4/2009 | Lenker |
| 7,524,316 B2 | 4/2009 | Hennings |
| 7,559,329 B2 | 7/2009 | Appling |
| 7,563,262 B2 | 7/2009 | Winston |
| 7,567,596 B2 | 7/2009 | Dantus |
| 7,572,254 B2 | 8/2009 | Hebert |
| 7,644,715 B2 | 1/2010 | Hayes |
| 7,651,503 B1 | 1/2010 | Coe |
| 7,666,161 B2 | 2/2010 | Nash |
| 7,699,790 B2 | 4/2010 | Simpson |
| 7,724,787 B2 | 5/2010 | Murison et al. |
| 7,779,842 B1 | 8/2010 | Russo |
| 7,787,506 B1 | 8/2010 | Jiang |
| 7,809,222 B2 | 10/2010 | Hartl |
| 7,811,281 B1 | 10/2010 | Rentrop |
| 7,828,793 B2 | 11/2010 | Thompson |
| 7,834,331 B2 | 11/2010 | Ben-Yakar |
| 7,837,677 B2 | 11/2010 | Thompson |
| 7,837,678 B2 | 11/2010 | Thompson |
| 7,846,153 B2 | 12/2010 | Hebert |
| 7,879,011 B2 | 2/2011 | Chang |
| D634,007 S | 3/2011 | Zinger |
| 7,912,554 B2 | 3/2011 | Capuano |
| 7,921,854 B2 | 4/2011 | Hennings |
| 7,924,892 B2 | 4/2011 | Chuang |
| 7,927,784 B2 | 4/2011 | Simpson |
| 7,929,579 B2 | 4/2011 | Hohm |
| 7,931,659 B2 | 4/2011 | Bose |
| 7,942,852 B2 | 5/2011 | Mas |
| 7,951,094 B2 | 5/2011 | Johansen |
| 7,957,790 B2 | 6/2011 | Kleen |
| 7,959,608 B2 | 6/2011 | Nash |
| 7,963,947 B2 | 6/2011 | Kurth |
| 7,963,961 B2 | 6/2011 | Thompson |
| 7,963,962 B2 | 6/2011 | Thompson |
| 7,975,528 B2 | 7/2011 | Hart |
| 7,976,533 B2 | 7/2011 | Larsson |
| 7,993,359 B1 | 8/2011 | Atwell |
| 8,016,784 B1 | 9/2011 | Hayzelden |
| 8,043,285 B2 | 10/2011 | Thompson |
| 8,059,274 B2 | 11/2011 | Splinter |
| 8,062,226 B2 | 11/2011 | Moore |
| 8,073,019 B2 | 12/2011 | Liu |
| 8,097,012 B2 | 1/2012 | Kagarise |
| 8,100,893 B2 | 1/2012 | Dadisman |
| 8,104,483 B2 | 1/2012 | Taylor |
| 8,114,429 B2 | 2/2012 | Michal |
| 8,128,951 B2 | 3/2012 | Michal |
| 8,157,747 B2 | 4/2012 | Grata |
| 8,182,474 B2 | 5/2012 | Winston |
| 8,189,971 B1 | 5/2012 | Vaissie |
| 8,202,268 B1 | 6/2012 | Wells |
| 8,238,386 B2 | 8/2012 | Limpert |
| 8,246,580 B2 | 8/2012 | Hopkins |
| 8,257,722 B2 | 9/2012 | Michal |
| 8,291,915 B2 | 10/2012 | Farley |
| 8,298,215 B2 | 10/2012 | Zinn |
| 8,300,669 B2 | 10/2012 | Dantus |
| 8,317,779 B2 | 11/2012 | Mirkov |
| 8,321,019 B2 | 11/2012 | Esch |
| 8,348,844 B2 | 1/2013 | Kunjan |
| 8,350,183 B2 | 1/2013 | Vogel |
| 8,353,899 B1 | 1/2013 | Wells |
| 8,365,741 B2 | 2/2013 | Hennings |
| 8,366,735 B2 | 2/2013 | Bose |
| 8,413,664 B2 | 4/2013 | Appling |
| 8,414,568 B2 | 4/2013 | Harlan |
| 8,422,134 B2 | 4/2013 | Wu |
| 8,425,501 B2 | 4/2013 | Appling |
| 8,428,747 B2 | 4/2013 | Coe |
| 8,435,235 B2 | 5/2013 | Stevens |
| 8,439,874 B2 | 5/2013 | Hertweck |
| 8,460,312 B2 | 6/2013 | Bose |
| 8,465,467 B2 | 6/2013 | Gao |
| 8,465,480 B2 | 6/2013 | Winston |
| 8,470,010 B2 | 6/2013 | Jakubowski |
| 8,486,051 B2 | 7/2013 | Larsson |
| 8,491,925 B2 | 7/2013 | Michal |
| 8,500,697 B2 | 8/2013 | Kurth |
| 8,512,326 B2 | 8/2013 | Shadduck |
| 8,535,360 B2 | 9/2013 | O'Dowd |
| 8,545,432 B2 | 10/2013 | Renati |
| 8,545,468 B2 | 10/2013 | Fabo |
| 8,551,067 B2 | 10/2013 | Zinger |
| 8,563,023 B2 | 10/2013 | Michal |
| 8,587,864 B2 | 11/2013 | Harter |
| 8,636,726 B1 | 1/2014 | Wells |
| 8,636,729 B2 | 1/2014 | Esch |
| 8,657,785 B2 | 2/2014 | Torrance |
| 8,668,665 B2 | 3/2014 | Gerg |
| 8,673,332 B2 | 3/2014 | Michal |
| 8,684,953 B2 | 4/2014 | Cabiri |
| 8,684,994 B2 | 4/2014 | Lev |
| 8,696,695 B2 | 4/2014 | Patel |
| 8,702,773 B2 | 4/2014 | Keeler |
| 8,721,634 B2 | 5/2014 | Esch |
| 8,728,066 B2 | 5/2014 | Shadduck |
| 8,734,825 B2 | 5/2014 | Michal |
| 8,752,598 B2 | 6/2014 | Denenburg |
| 8,753,325 B2 | 6/2014 | Lev |
| 8,758,333 B2 | 6/2014 | Harlan |

(56) References Cited

U.S. PATENT DOCUMENTS

| | | |
|---|---|---|
| 8,767,287 B2 | 7/2014 | Clowes |
| 8,784,394 B2 | 7/2014 | Kerr |
| 8,808,074 B2 | 8/2014 | Kim |
| 8,814,922 B2 | 8/2014 | Hennings |
| 8,840,606 B2 | 9/2014 | Appling |
| 8,852,145 B2 | 10/2014 | Denenburg |
| 8,852,165 B2 | 10/2014 | Mackay, II |
| 8,852,178 B2 | 10/2014 | Thompson |
| 8,855,151 B2 | 10/2014 | Harter |
| 8,861,075 B2 | 10/2014 | Dantus |
| 8,864,754 B2 | 10/2014 | Appling |
| 8,864,755 B2 | 10/2014 | Appling |
| 8,881,735 B2 | 11/2014 | Mitchell |
| 8,887,733 B2 | 11/2014 | Appling |
| D720,451 S | 12/2014 | Denenburg |
| 8,905,994 B1 | 12/2014 | Lev |
| 8,915,896 B2 | 12/2014 | Sanders |
| 8,920,402 B2 | 12/2014 | Nash |
| 8,953,648 B2 | 2/2015 | Ishaaya |
| 8,956,376 B2 | 2/2015 | Alvarez |
| 8,961,551 B2 | 2/2015 | Taylor |
| 8,979,792 B2 | 3/2015 | Lev |
| 8,979,828 B2 | 3/2015 | Fix |
| 8,998,875 B2 | 4/2015 | Lev |
| 8,998,936 B2 | 4/2015 | Alvarez |
| 9,028,520 B2 | 5/2015 | Taylor |
| 9,034,362 B2 | 5/2015 | Michal |
| 9,044,829 B2 | 6/2015 | Crist |
| 9,050,127 B2 | 6/2015 | Bonnette |
| 9,066,736 B2 | 6/2015 | Islam |
| 9,066,742 B2 | 6/2015 | Splinter |
| D734,868 S | 7/2015 | Gilboa |
| 9,119,656 B2 | 9/2015 | Bose |
| 9,119,907 B2 | 9/2015 | Sherman |
| 9,125,562 B2 | 9/2015 | Spencer |
| 9,132,211 B2 | 9/2015 | Michal |
| D740,946 S | 10/2015 | Szabo |
| 9,162,038 B2 | 10/2015 | Rottenberg |
| D742,520 S | 11/2015 | Szabo |
| D742,521 S | 11/2015 | Szabo |
| D742,522 S | 11/2015 | Szabo |
| 9,198,968 B2 | 12/2015 | Michal |
| 9,199,011 B2 | 12/2015 | Locke |
| 9,216,056 B2 | 12/2015 | Datta |
| 9,220,523 B2 | 12/2015 | Taylor |
| D748,266 S | 1/2016 | Szabo |
| 9,238,122 B2 | 1/2016 | Malhi |
| 9,248,221 B2 | 2/2016 | Look |
| 9,254,175 B2 | 2/2016 | Winston |
| 9,283,039 B2 | 3/2016 | Harlan |
| 9,283,040 B2 | 3/2016 | Hendrick |
| 9,287,677 B2 | 3/2016 | Clowes |
| 9,289,173 B2 | 3/2016 | Splinter |
| 9,289,226 B2 | 3/2016 | Taylor |
| 9,291,663 B2 | 3/2016 | Grace |
| 9,295,373 B2 | 3/2016 | Torrance |
| D753,289 S | 4/2016 | Shimon |
| D753,290 S | 4/2016 | Shimon |
| 9,308,047 B2 | 4/2016 | Taylor |
| 9,320,530 B2 | 4/2016 | Grace |
| 9,333,007 B2 | 5/2016 | Escudero |
| 9,339,337 B2 | 5/2016 | Fix |
| 9,345,508 B2 | 5/2016 | Hendrick |
| 9,345,510 B2 | 5/2016 | Patel |
| 9,358,042 B2 | 6/2016 | Magee |
| 9,368,931 B2 | 6/2016 | Bragagna |
| 9,408,665 B2 | 8/2016 | Sauro |
| 9,408,998 B2 | 8/2016 | Alvarez |
| 9,413,896 B2 | 8/2016 | Bowe |
| 9,421,035 B2 | 8/2016 | Hendrick |
| 9,421,065 B2 | 8/2016 | Splinter |
| 9,456,672 B2 | 10/2016 | Condon |
| 9,456,872 B2 | 10/2016 | Hendrick |
| 9,510,854 B2 | 12/2016 | Mallaby |
| D775,728 S | 1/2017 | Cavada et al. |
| 9,566,116 B2 | 2/2017 | Winston |
| 9,603,618 B2 | 3/2017 | Grace |
| 9,622,819 B2 | 4/2017 | Mitchell |
| 9,623,211 B2 | 4/2017 | Hendrick |
| 9,636,482 B2 | 5/2017 | McDaniel |
| 9,642,646 B2 | 5/2017 | Patel |
| 9,649,158 B2 | 5/2017 | Datta |
| 9,649,159 B2 | 5/2017 | Keeler |
| 9,655,633 B2 | 5/2017 | Leynov |
| 9,662,478 B2 | 5/2017 | Browd |
| 9,668,765 B2 | 6/2017 | Grace |
| 9,668,766 B2 | 6/2017 | Rottenberg |
| 9,675,371 B2 | 6/2017 | Shimon |
| 9,675,415 B2 | 6/2017 | Varghese |
| 9,676,167 B2 | 6/2017 | Marjanovic |
| 9,678,405 B2 | 6/2017 | Mironov |
| 9,681,882 B2 | 6/2017 | Garrison |
| 9,694,118 B2 | 7/2017 | Esnouf |
| 9,724,122 B2 | 8/2017 | Hendrick |
| 9,730,756 B2 * | 8/2017 | Ben Oren ........ A61B 17/32053 |
| 9,731,098 B2 | 8/2017 | Hendrick |
| 9,731,113 B2 | 8/2017 | Grace |
| 9,757,200 B2 | 9/2017 | Magee et al. |
| 9,760,518 B2 | 9/2017 | Grossman |
| 9,763,692 B2 | 9/2017 | Bowe |
| 9,770,536 B2 | 9/2017 | Speck |
| 9,774,161 B2 | 9/2017 | Zach |
| 9,775,969 B2 | 10/2017 | Alvarez |
| 9,795,505 B2 | 10/2017 | Yu |
| 9,801,650 B2 | 10/2017 | Taylor |
| 9,803,973 B1 | 10/2017 | Sajedi |
| 9,808,275 B2 | 11/2017 | Taylor |
| 9,808,277 B2 | 11/2017 | Nash |
| 9,814,862 B2 | 11/2017 | Alvarez |
| 9,820,761 B2 | 11/2017 | Garrison |
| 9,821,090 B2 | 11/2017 | Triffo |
| 9,827,055 B2 | 11/2017 | Hendrick |
| 9,844,410 B2 | 12/2017 | Mitchell |
| 9,844,485 B2 | 12/2017 | Locke |
| 9,848,952 B2 | 12/2017 | Khanna |
| 9,855,100 B2 | 1/2018 | Splinter |
| 9,855,374 B2 | 1/2018 | Sherman |
| 9,864,140 B2 * | 1/2018 | Adler ................ G02B 27/0911 |
| 9,878,399 B2 | 1/2018 | Liu |
| 9,882,342 B2 | 1/2018 | Zach |
| 9,883,877 B2 | 2/2018 | Look |
| 9,883,885 B2 | 2/2018 | Hendrick |
| 9,884,184 B2 | 2/2018 | Triffo |
| 9,895,473 B2 | 2/2018 | Look |
| 9,907,614 B2 | 3/2018 | Grace |
| 9,907,615 B2 | 3/2018 | Keeler |
| 9,913,688 B1 | 3/2018 | Karavitis |
| 9,918,729 B2 | 3/2018 | Taylor |
| 9,925,316 B2 | 3/2018 | Sanders |
| 9,925,366 B2 | 3/2018 | Grace |
| 9,925,371 B2 | 3/2018 | Grace |
| 9,931,166 B2 | 4/2018 | Sauro |
| 9,937,005 B2 | 4/2018 | Hendrick |
| 9,949,753 B2 | 4/2018 | Bowe |
| 9,958,385 B2 | 5/2018 | Manassen |
| 9,962,527 B2 | 5/2018 | Laudenslager |
| 9,980,743 B2 | 5/2018 | Grace |
| 9,999,468 B2 | 6/2018 | Chalfant |
| 10,010,657 B2 | 7/2018 | Torrance |
| 10,039,569 B2 | 8/2018 | Hendrick |
| 10,046,093 B2 | 8/2018 | Michal |
| 10,052,129 B2 | 8/2018 | Grace |
| 10,079,466 B2 | 9/2018 | Ishaaya |
| 10,080,608 B2 | 9/2018 | Datta |
| 10,085,883 B2 | 10/2018 | Auld |
| 10,092,357 B2 | 10/2018 | Fix |
| 10,092,363 B2 | 10/2018 | Magee |
| 10,105,533 B2 | 10/2018 | Grace |
| 10,111,709 B2 | 10/2018 | Taylor |
| 10,117,970 B2 | 11/2018 | Michal |
| 10,135,225 B2 | 11/2018 | Weichmann |
| 10,136,913 B2 | 11/2018 | Grace |
| 10,141,709 B2 | 11/2018 | Ishaaya |
| 10,149,718 B2 | 12/2018 | Fiser |

(56) References Cited

U.S. PATENT DOCUMENTS

| | | |
|---|---|---|
| 10,166,375 B2 | 1/2019 | Browd |
| 10,183,150 B2 | 1/2019 | McDaniel |
| 10,183,151 B2 | 1/2019 | Alvarez |
| 10,201,315 B2 | 2/2019 | Peatfield |
| 10,201,387 B2 | 2/2019 | Grace |
| 10,206,745 B2 | 2/2019 | Hendrick |
| 10,219,819 B2 | 3/2019 | Grace |
| 10,226,263 B2 | 3/2019 | Look |
| 10,236,952 B1 | 3/2019 | Sadot |
| 10,245,107 B2 | 4/2019 | Sierra |
| 10,258,792 B2 | 4/2019 | Archuleta |
| 10,265,520 B2 | 4/2019 | Grace |
| 10,271,904 B2 | 4/2019 | Islam |
| 10,285,726 B2 | 5/2019 | Nguyen |
| 10,305,244 B2 | 5/2019 | Sierra |
| 10,321,931 B2 | 6/2019 | Aljuri |
| 10,342,902 B2 | 7/2019 | Bagwell |
| 10,363,398 B2 | 7/2019 | Gerrans |
| 10,391,275 B2 | 8/2019 | Burnett |
| 10,405,924 B2 | 9/2019 | Bowe |
| 10,499,944 B2 | 12/2019 | Mallaby |
| 10,531,883 B1 | 1/2020 | Deville |
| 10,603,415 B2 | 3/2020 | Look |
| 10,702,292 B2 | 7/2020 | Look |
| 10,716,583 B2 | 7/2020 | Look |
| 10,716,880 B2 | 7/2020 | Culbert |
| 10,722,253 B2 | 7/2020 | Deville |
| 10,765,592 B2 | 9/2020 | Locke |
| 10,772,683 B2 * | 9/2020 | Zabar ................... G02B 6/4296 |
| 10,792,103 B2 | 10/2020 | Zabar |
| 10,835,647 B2 | 11/2020 | Sherman |
| 10,835,711 B2 | 11/2020 | Yang |
| 10,993,731 B2 | 5/2021 | Leynov |
| 11,051,832 B2 | 7/2021 | Look |
| 11,090,117 B2 | 8/2021 | Zabar |
| 11,096,712 B2 | 8/2021 | Teigen |
| 11,197,683 B1 | 12/2021 | Teigen |
| 11,247,030 B2 | 2/2022 | Browd |
| 11,259,821 B2 | 3/2022 | Buck |
| 11,317,787 B2 * | 5/2022 | Hillman ............. G02B 21/0028 |
| 11,337,712 B2 | 5/2022 | Teigen |
| 11,357,951 B2 | 6/2022 | Burnett |
| 11,369,435 B2 | 6/2022 | Khan |
| 11,400,255 B1 | 8/2022 | Chou |
| 11,406,402 B2 | 8/2022 | Deville |
| 11,432,835 B2 | 9/2022 | Shaffer |
| 11,464,528 B2 | 10/2022 | Brady |
| 11,471,582 B2 | 10/2022 | Yee |
| 11,490,909 B2 | 11/2022 | Look |
| 11,497,521 B2 | 11/2022 | Mallaby |
| 11,547,426 B2 | 1/2023 | Deville |
| 11,835,707 B2 * | 12/2023 | Liang ...................... A61B 1/07 |
| 2001/0001314 A1 | 5/2001 | Davison |
| 2001/0016739 A1 | 8/2001 | Goldman |
| 2001/0016749 A1 | 8/2001 | Blatter |
| 2002/0016624 A1 | 2/2002 | Patterson |
| 2002/0045811 A1 | 4/2002 | Kittrell |
| 2002/0072680 A1 | 6/2002 | Schock |
| 2002/0095087 A1 | 7/2002 | Mourad |
| 2002/0173811 A1 | 11/2002 | Tu |
| 2002/0183729 A1 | 12/2002 | Farr |
| 2003/0009157 A1 | 1/2003 | Levine |
| 2003/0050686 A1 | 3/2003 | Raeder-Devens |
| 2003/0078568 A1 | 4/2003 | Caldera |
| 2003/0120256 A1 | 6/2003 | Lary |
| 2003/0125709 A1 | 7/2003 | Eidenschink |
| 2003/0125719 A1 | 7/2003 | Furnish |
| 2003/0171691 A1 * | 9/2003 | Casscells, III ....... A61B 5/0075 |
| | | 600/549 |
| 2003/0181823 A1 | 9/2003 | Gatto |
| 2003/0181847 A1 | 9/2003 | Bruno-Raimondi |
| 2003/0181938 A1 | 9/2003 | Roth |
| 2003/0191460 A1 | 10/2003 | Hobbs |
| 2003/0199860 A1 | 10/2003 | Loeb |
| 2003/0199960 A1 | 10/2003 | Paskar |
| 2004/0044337 A1 | 3/2004 | Shafirstein |
| 2004/0093044 A1 | 5/2004 | Rychnovsky |
| 2004/0102766 A1 | 5/2004 | Poleo |
| 2004/0138562 A1 | 7/2004 | Makower |
| 2004/0142654 A1 | 7/2004 | Stammer |
| 2004/0162516 A1 | 8/2004 | Mandrusov |
| 2004/0193055 A1 | 9/2004 | Field |
| 2004/0236228 A1 | 11/2004 | Stoltz |
| 2005/0015123 A1 | 1/2005 | Paithankar |
| 2005/0020901 A1 | 1/2005 | Belson |
| 2005/0107738 A1 | 5/2005 | Slater |
| 2005/0113798 A1 | 5/2005 | Slater |
| 2005/0131400 A1 | 6/2005 | Hennings |
| 2005/0177132 A1 | 8/2005 | Lentz |
| 2005/0187537 A1 | 8/2005 | Loeb |
| 2005/0203497 A1 | 9/2005 | Speeg |
| 2005/0244101 A1 | 11/2005 | Kitabayashi |
| 2005/0251116 A1 | 11/2005 | Steinke |
| 2005/0288655 A1 | 12/2005 | Root |
| 2006/0069417 A1 | 3/2006 | Farley |
| 2006/0095015 A1 | 5/2006 | Hobbs |
| 2006/0095059 A1 | 5/2006 | Bleich |
| 2006/0106338 A1 | 5/2006 | Chang |
| 2006/0137345 A1 | 6/2006 | Cho |
| 2006/0142747 A1 | 6/2006 | Appling |
| 2006/0149218 A1 | 7/2006 | Slater |
| 2006/0189967 A1 | 8/2006 | Masotti |
| 2006/0229515 A1 | 10/2006 | Sharareh |
| 2006/0241495 A1 | 10/2006 | Kurtz |
| 2006/0241572 A1 | 10/2006 | Zhou |
| 2006/0253112 A1 | 11/2006 | Suarez |
| 2006/0264905 A1 | 11/2006 | Eskridge |
| 2007/0016177 A1 | 1/2007 | Vaynberg |
| 2007/0073160 A1 | 3/2007 | Imam |
| 2007/0073268 A1 | 3/2007 | Goble |
| 2007/0073278 A1 | 3/2007 | Johnson |
| 2007/0123846 A1 | 5/2007 | Hennings |
| 2007/0129706 A1 | 6/2007 | Katoh |
| 2007/0135791 A1 | 6/2007 | Slater |
| 2007/0149985 A1 | 6/2007 | Cole |
| 2007/0167937 A1 | 7/2007 | Brown |
| 2007/0179485 A1 | 8/2007 | Yeik |
| 2007/0179486 A1 | 8/2007 | Welch |
| 2007/0179575 A1 | 8/2007 | Esch |
| 2007/0208400 A1 | 9/2007 | Nadkarni |
| 2007/0270688 A1 | 11/2007 | Gelbart |
| 2007/0299404 A1 | 12/2007 | Katoh |
| 2007/0299431 A1 | 12/2007 | Jakubowski |
| 2008/0015559 A1 | 1/2008 | Appling |
| 2008/0071333 A1 | 3/2008 | Hayes |
| 2008/0082091 A1 * | 4/2008 | Rubtsov .................. A61B 18/24 |
| | | 606/17 |
| 2008/0114428 A1 | 5/2008 | Trembly |
| 2008/0119869 A1 | 5/2008 | Teague |
| 2008/0146918 A1 | 6/2008 | Magnin |
| 2008/0154257 A1 | 6/2008 | Sharareh |
| 2008/0154293 A1 | 6/2008 | Taylor |
| 2008/0177186 A1 | 7/2008 | Slater |
| 2008/0188843 A1 | 8/2008 | Appling |
| 2008/0188910 A1 | 8/2008 | Spaide |
| 2008/0200873 A1 | 8/2008 | Espinosa |
| 2008/0208180 A1 | 8/2008 | Cartier |
| 2008/0221560 A1 | 9/2008 | Arai |
| 2008/0249399 A1 | 10/2008 | Appling |
| 2008/0262465 A1 | 10/2008 | Zinger |
| 2008/0275445 A1 | 11/2008 | Kelly |
| 2008/0300583 A1 | 12/2008 | Foley |
| 2008/0300662 A1 | 12/2008 | Taylor |
| 2008/0319418 A1 | 12/2008 | Chong |
| 2009/0018486 A1 | 1/2009 | Goren |
| 2009/0018603 A1 | 1/2009 | Mitelberg |
| 2009/0082760 A1 | 3/2009 | Zinn |
| 2009/0105654 A1 | 4/2009 | Kurth |
| 2009/0125007 A1 | 5/2009 | Splinter |
| 2009/0163899 A1 | 6/2009 | Burton |
| 2009/0182281 A1 | 7/2009 | Kurth |
| 2009/0209907 A1 | 8/2009 | Grata |
| 2009/0234344 A1 | 9/2009 | Lavender |
| 2009/0234378 A1 | 9/2009 | Escudero |

(56) References Cited

U.S. PATENT DOCUMENTS

| | | |
|---|---|---|
| 2009/0247823 A1 | 10/2009 | Yamamoto |
| 2009/0254078 A1 | 10/2009 | Just |
| 2009/0264875 A1 | 10/2009 | Appling |
| 2009/0299351 A1 | 12/2009 | Dadisman |
| 2010/0016857 A1 | 1/2010 | McKenna |
| 2010/0057056 A1 | 3/2010 | Gurtner |
| 2010/0069897 A1 | 3/2010 | Spikker |
| 2010/0125253 A1 | 5/2010 | Olson |
| 2010/0152720 A1 | 6/2010 | Sauro |
| 2010/0168572 A1 | 7/2010 | Sliwa |
| 2010/0168823 A1 | 7/2010 | Strisower |
| 2010/0191178 A1 | 7/2010 | Ross |
| 2010/0198150 A1 | 8/2010 | Michal |
| 2010/0198240 A1 | 8/2010 | Simpson |
| 2010/0198247 A1 | 8/2010 | Chang |
| 2010/0210995 A1 | 8/2010 | Jakubowski |
| 2010/0234925 A1 | 9/2010 | Harris |
| 2010/0280504 A1 | 11/2010 | Manzke et al. |
| 2010/0286791 A1 | 11/2010 | Goldsmith |
| 2010/0296531 A1 | 11/2010 | Hohm |
| 2010/0305475 A1 | 12/2010 | Hinchliffe |
| 2010/0305715 A1 | 12/2010 | Mathis |
| 2010/0312263 A1 | 12/2010 | Moberg |
| 2010/0318067 A1 | 12/2010 | Klima |
| 2011/0034922 A1 | 2/2011 | Thompson |
| 2011/0060300 A1 | 3/2011 | Weig |
| 2011/0134523 A1 | 6/2011 | Wu |
| 2011/0172586 A1 | 7/2011 | Hennings |
| 2011/0213446 A1 | 9/2011 | Tucek |
| 2011/0251519 A1 | 10/2011 | Romoscanu |
| 2011/0270238 A1 | 11/2011 | Rizq |
| 2012/0065490 A1 | 3/2012 | Zharov |
| 2012/0109191 A1 | 5/2012 | Marano, Jr. |
| 2012/0130415 A1 | 5/2012 | Tal |
| 2012/0265183 A1 | 10/2012 | Tulleken |
| 2012/0271170 A1 | 10/2012 | Emelianov |
| 2013/0005236 A1 | 1/2013 | Kim |
| 2013/0096545 A1 | 4/2013 | Laudenslager |
| 2013/0131643 A1 | 5/2013 | Parodi |
| 2013/0131644 A1 | 5/2013 | Parodi |
| 2013/0197306 A1 | 8/2013 | Armand |
| 2013/0211379 A1 | 8/2013 | Clair |
| 2013/0231660 A1 | 9/2013 | Edwards |
| 2013/0261614 A1 | 10/2013 | Appling |
| 2013/0274674 A1 | 10/2013 | Fischell |
| 2013/0304034 A1 | 11/2013 | Cabiri |
| 2013/0310680 A1 | 11/2013 | Werahera |
| 2013/0345541 A1 | 12/2013 | Nau, Jr. |
| 2014/0031800 A1 | 1/2014 | Ben Oren |
| 2014/0052114 A1 | 2/2014 | Ben-Oren |
| 2014/0081292 A1 | 3/2014 | Moll |
| 2014/0133814 A1 | 5/2014 | Stevens |
| 2014/0180034 A1 | 6/2014 | Hoseit |
| 2014/0188062 A1 | 7/2014 | James |
| 2014/0263207 A1 | 9/2014 | Liu |
| 2014/0276682 A1 | 9/2014 | Hendrick |
| 2014/0276689 A1 | 9/2014 | Grace |
| 2014/0343482 A1 | 11/2014 | Mackay |
| 2014/0358134 A1 | 12/2014 | Appling |
| 2015/0038953 A1 | 2/2015 | Varghese |
| 2015/0057648 A1 | 2/2015 | Swift |
| 2015/0164573 A1 | 6/2015 | Delaney |
| 2015/0238091 A1 | 8/2015 | Iyer |
| 2015/0320480 A1 | 11/2015 | Cosman, Jr. |
| 2015/0359595 A1 | 12/2015 | Ben Oren et al. |
| 2016/0135883 A1 | 5/2016 | Herscher |
| 2017/0100142 A1 | 4/2017 | Look |
| 2017/0246444 A1 | 8/2017 | Domatch |
| 2018/0028794 A1 | 2/2018 | Browd |
| 2018/0207397 A1 | 7/2018 | Look |
| 2019/0015157 A1 | 1/2019 | Grace |
| 2019/0216476 A1 | 7/2019 | Barry |
| 2019/0290815 A1 | 9/2019 | Antonicelli |
| 2019/0336732 A1 | 11/2019 | Laudenslager |
| 2019/0343445 A1 | 11/2019 | Burnett |
| 2020/0009301 A1 | 1/2020 | Yee |
| 2020/0015840 A1 | 1/2020 | Mallaby |
| 2020/0022711 A1 | 1/2020 | Look |
| 2020/0179576 A1 | 6/2020 | Wood |
| 2020/0179578 A1 | 6/2020 | Look |
| 2020/0206457 A1 | 7/2020 | Boling |
| 2020/0281610 A1 | 9/2020 | Look |
| 2020/0289722 A1 | 9/2020 | Culbert |
| 2020/0297362 A1 | 9/2020 | Deville |
| 2020/0337772 A1* | 10/2020 | Ben-Oren .............. A61B 18/24 |
| 2020/0367917 A1 | 11/2020 | Teigen |
| 2020/0397957 A1 | 12/2020 | Teigen |
| 2021/0038306 A1 | 2/2021 | McLoughlin |
| 2021/0069467 A1 | 3/2021 | Garrison |
| 2021/0093756 A1 | 4/2021 | Sherman |
| 2021/0109743 A1* | 4/2021 | Liang ................. A61B 1/00188 |
| 2021/0128182 A1 | 5/2021 | Teigen |
| 2021/0315598 A1 | 10/2021 | Buck |
| 2022/0008090 A1 | 1/2022 | Look |
| 2022/0031930 A1 | 2/2022 | Downey |
| 2022/0096104 A1 | 3/2022 | Ogle |
| 2022/0152345 A1 | 5/2022 | Simiele |
| 2022/0152346 A1 | 5/2022 | Burnett |
| 2022/0176031 A1 | 6/2022 | Cheng |
| 2022/0193366 A1 | 6/2022 | Cheng |
| 2022/0211437 A1* | 7/2022 | Ben-Oren .............. A61B 18/24 |
| 2022/0218365 A1 | 7/2022 | Deville |
| 2022/0257268 A1 | 8/2022 | Culbert |
| 2022/0280171 A1 | 9/2022 | Teigen |
| 2022/0338887 A1 | 10/2022 | Nair |
| 2022/0339338 A1 | 10/2022 | Nair |
| 2022/0339339 A1 | 10/2022 | Nair |
| 2022/0378443 A1 | 12/2022 | Look |
| 2022/0378450 A1 | 12/2022 | Culbert |
| 2022/0379081 A1 | 12/2022 | Look |
| 2022/0379082 A1 | 12/2022 | Look |
| 2022/0379083 A1 | 12/2022 | Look |
| 2022/0379084 A1 | 12/2022 | Look |
| 2022/0379085 A1 | 12/2022 | Look |
| 2022/0379086 A1 | 12/2022 | Look |
| 2022/0387052 A1 | 12/2022 | Look |
| 2022/0387752 A1 | 12/2022 | Look |
| 2022/0387753 A1 | 12/2022 | Look |
| 2023/0026412 A1 | 1/2023 | Teigen |
| 2023/0099283 A1 | 3/2023 | Deville |
| 2023/0100426 A1 | 3/2023 | Deville |
| 2023/0301708 A1* | 9/2023 | Mickelsen .............. A61B 18/14 |
| 2023/0329780 A1* | 10/2023 | Liu .................... A61B 18/1492 |
| 2023/0408329 A1* | 12/2023 | Zabar .................... G01J 1/4257 |

FOREIGN PATENT DOCUMENTS

| | | |
|---|---|---|
| CA | 3105728 A1 | 1/2020 |
| CN | 1049287 A | 2/1991 |
| CN | 1261774 A | 8/2000 |
| CN | 2713994 | 8/2005 |
| CN | 101170959 | 4/2008 |
| CN | 101795630 | 8/2010 |
| CN | 112533550 A | 3/2021 |
| DE | 8905642 U1 | 8/1989 |
| DE | 60316175 T2 | 5/2008 |
| EP | 0311295 A2 | 4/1989 |
| EP | 0341943 | 11/1989 |
| EP | 1567082 | 8/2005 |
| EP | 1610855 A2 | 1/2006 |
| EP | 1709987 | 10/2006 |
| EP | 2226031 A1 | 9/2010 |
| EP | 2399507 | 12/2011 |
| EP | 3025175 A1 | 6/2016 |
| EP | 3423124 A4 | 10/2019 |
| EP | 3806757 A4 | 5/2022 |
| GB | 1533204 A | 11/1978 |
| IL | 224434 A | 12/2016 |
| JP | H01178011 | 7/1989 |
| JP | 2021532850 A | 12/2021 |
| KR | 20210035811 A | 4/2021 |
| WO | 9214515 A1 | 9/1992 |
| WO | 9509575 A1 | 4/1995 |
| WO | 9834673 | 8/1998 |

(56) References Cited

FOREIGN PATENT DOCUMENTS

| | | |
|---|---|---|
| WO | 0245601 A1 | 6/2002 |
| WO | 03057060 A1 | 7/2003 |
| WO | 2004021886 A1 | 3/2004 |
| WO | 2004043280 A1 | 5/2004 |
| WO | 2007125638 | 11/2007 |
| WO | 2008124790 | 10/2008 |
| WO | 02011107117 A1 | 9/2011 |
| WO | 2012114333 A1 | 8/2012 |
| WO | 2012114334 A1 | 8/2012 |
| WO | 2012151396 | 11/2012 |
| WO | 2013172970 A1 | 11/2013 |
| WO | 2014118738 A1 | 8/2014 |
| WO | 2017155994 A1 | 9/2017 |
| WO | 2018019829 A1 | 2/2018 |

OTHER PUBLICATIONS

Pandya et al (2015) Radiofrequency ablation of pancreatic ductal adenocarcinoma: The past, the present and the future, World Journal of Gastrointestinal Oncology, Feb. 15, 2015, vol. 7, No. 2, pp. 6-11.
Papaioannou, Thanassis, et al., Excimer Laser Assisted Thrombolysis: The Effect of Fluence, Repetition Rate, and Catheter Size, Lasers in Surgery: Advanced Characterization, Therapeutics, and systems XII, Kenneth E. Bartels et al., Editors, Proceedings of SPIE vol. 4609 (2002), 6 pages.
Papaioannou, Thanassis, et al., Particulate debris analysis during excimer laser thrombolysis: An in-vitro study., Lasers in Surgery: Advanced Characterization, Therapeutics, and systems XII, Kenneth E. Bartels et al., Editors, Proceedings of SPIE vol. 4609 (2002), 9 pages.
Park, et al, Fluoroscopy-Guided Endovenous Foam Sclerotherapy Using a Microcatheter in Varicose Tributaries Followed by Endovenous Laser Treatment of Incompetent Saphenous Veins: Technocal Feasibility and Early Results, Dermatol Surg 2009, 35:804-812.
Partial European Search Report, EP19177412, Jul. 17, 2019, 1 page.
Pories and Albrecht (2001) Etiology of type II diabetes mellitus: role of the foregut. World J Surg 25(4): 527-31.
Pories et al., (2011) The surgical treatment of type two diabetes mellitus. Surg Clin North Am 91(4): 821-36.
Prince, M.R., et al, Preferential Light Absorption in Atheromas in Vitro—Implications for Laser Angioplasty, J of Clin Investigation, vol. 78(1) (Jul. 1986) pp. 295-302.
Proebstle, et al, Thermal Damage of The Inner Vein Wall During Endovenous Laser Treatment: Key Role of Energy Absorption by Intravascular Blood, Dermatol Surf 2002:28596-600.
Proebstle, et al, Treatment of the Incompetent Great Saphenous Vein by Endovenous RF Powered Segmental Therman Ablation: First Clinical Experience, Journal of Vascular Surgery, 2008, pp. 151-156.e1.
Richou, B, et al., Delivery of 10-mw Nd:YAG Laser Pulses by Large Core Optical Fibers: Dependence of the Laser-Itensity Profile on Beam Propagation, Applied Optics, vol. 36, No. 7 (1997) pp. 1610-1614.
Ronkainen et al., (2005) Prevalence of Barrett's esophagus in the general population: an endoscopic study. Gastroenterology 129(6): 1825-1831.
Ronkainen, Jukka, et al., Prevalence of Barrett's Esophagus in the General Population: An Endoscopic Study, Gastroenterology 2005; 129:1825-1831.
Rubino and Gagner (2002) Potential of surgery for curing type 2 diabetes mellitus. Ann Surg 236(5): 554-559.
Rubino and Marescaux (2004) Effect of duodenal-jejunal exclusion in a non-obese animal model of type 2 diabetes: a new perspective for an old disease. Ann Surg 239(1): 1-11.
Rubino et al, (2006) The mechanism of diabetes control after gastrointestinal bypass surgery reveals a role of the proximal small intestine in the pathophysiology of type 2 diabetes. Ann Surg 244(5): 741-749.
Rubino et al., (2004) The early effect of the Roux-en-Y gastric bypass on hormones involved in body weight regulation and glucose metabolism. Ann Surg 240(2): 236-42.
Schmedt, et al., Evaluation of Endovenous RF Ablation and Laser Therapy with Endoluminal Optical Coherence Tomography in an Ex Vivo Model, Journal of Vase Surg, 2007, pp. 1047-1058.
Schmidt-Uhling, T, et al, New Simplified Coupling Scheme for the Delivery of 20MW Nd:YAG Laser Pulses by Large Core Optical Fibers, Applied Physics B, Lasers and Optics, vol. 72, (2001) pp. 183-186.
Schwarz, et al., Endovenous Laser Ablation of Varicose Veins with the 1470-nm Diode Laser, Journal of Vase Surg vol. 51, No. 6, pp. 1474-1478. (2010).
Schwarzwälder and Zeller (2010) Debulking procedures: potential device specific indications. Tech Vasc Interv Radiol 13(1): 43-53.
Shangguan, HanQun, et al., Microsecond Laser Ablation of Thrombus and Gelatin Under Clear Liquids: Contact Versus Noncontact, IEEE Journal of Selected Topics in Quantum Electronics, vol. 2, No. 4, Dec. 1996, 8 pages.
Shuto, et al, Fiber Fuse Phenomenon in Step-Index Single-Mode Optical Fibers, IEEE Journal of Quantum Electronics, vol. 40, No., 8, 2004, pp. 1113-1121.
Sikorska and Pan (2004) The Effect of Waveguide Material and Shape on Acoustic Emission Transmission Characteristics, Part 1: Traditional Features. Journal of Acoustic Emission 22: 264-273.
Skorczakowski et al., (2010) Mid-infrared Q-switched Er:YAG laser for medical applications. Laser Physics Letters 7 (7): 498-504.
Smucler, et al, Invasive Leg Veins Treatment with 1064/1319 Nd:YAG Laser/Combination with Dye Laser Treatment, SPIE vol. 3590, pp. 78-87. (1999).
Tabbara, et al, Laser-Fused Biologic Vascular Graft Anastomoses, Journal of Investigative Surgery, 6:3, 289-295. (1993).
Taylor, et al, Long Saphenous Vein Stripping Under Local Anaesthesia, Annals of the Royal College of Surgeons of England, 1981, vol. 63, pp. 206-207.
Taylor, Rod S., et al., Dependence of the XeCI Laser Cut Rate of Plaque on the Degree of Calcification, Laser Fluence, and Optical Pulse Duration, Lasers in Surgery and Medicine, vol. 10, Issue 5, (1990) pp. 414-419.
Topaz, On, M.D et al., "Optimally Spaced" Excimer Laser Coronary Catheters: Performance Analysis, Journal of Clinical Laser Medicine & Surgery vol. 19, No. 1, 2001, Mary Ann Liebert, Inc., pp. 9-14.
Verdam et al., (2012) An update on less invasive and endoscopic techniques mimicking the effect of bariatric surgery. J Obes 2012:597871, pp. 1-11.
Vuylsteke, et al, Intraluminal Fibre-Tip Centring Can Improve Endovenous Laser Ablation: A Histological Study, Eur J Vase Endovasc Surg, 2009, pp. 1-7.
Wang et al, (2013) Total transmission and total reflection of acoustic wave by zero index metamatehals loaded with general solid defects. Journal of Applied Physics 114(19): 194502, pp. 1-5.
Written Opinion of the International Searching Authority PCT/IL2017/050498; Mailed Sep. 10, 2017, 6 pages.
Written Opinion of the International Searching Authority, PCT/IL2012/000089, Jul. 13, 2012, 8 pages.
Written Opinion of the International Searching Authority, PCT/IL2014/058688, Jun. 15, 2014, 6 pages.
Written Opinion of the International Searching Authority, PCT/IL2015/050480, Oct. 21, 2015, 7 pages.
Written Opinion of the International Searching Authority, PCT/IL2015/050529, Sep. 16, 2015, 5 pages.
Written Opinion of the International Searching Authority, PCT/IL2017/050498, Nov. 9, 2017, 6 pages.
Albagli, D., et al., Time Dependence of Laser-Induced Surface Breakdown in Fused Silica at 355nm in the Nanosecond Regime, SPIE vol. 1441, Laser Induced Damage in Optical Materials, 1990, 8 pages.
Alexander (1991) Tissue pathologies uncovered by spectral analysis. J Clin Laser Med Surg 9(4): 238-241.

(56) References Cited

OTHER PUBLICATIONS

Almeida, et al, RF Endovenous ClosureFAST Versus Laser Ablation for the Treatment of Great Saphenous Reflux: A Multicenter, Single-blinded, Randomized Study, J Vasc Interv Radiol 2009, 20:752-759.

Ambrosini, V. et al., Excimer laser in acute myocardial infarction: Single centre experience on 66 patients, International Journal of Cardiology 127 (2008) 98-102.

Chong, et al, Technical Tip: Cold Saline Infiltration Instead of Local Anaesthetic in Endovenous Laser Treatment, Phlebology vol. 21 No. 2, 2006, oo 88-89.

Coe, M. Sean, et al., Excimer Laser Lead Extraction Catheter with Increased Laser Parameters, Lasers in Surgery: Advanced Characterization, Therapeutics, and Systems Xi, R. Rox Anderson et al., Editors, Proceedings of SPIE vol. 4244 (2001), 8 pages.

Cordis® Outback® Re-Entry Catheter, Chronic Total Occlusion (CTO) Technologies brochure, Dec. 2008.

Cummings et al., (2004) Gastric bypass for obesity: mechanisms of weight loss and diabetes resolution. J Clin Endocrinol Metab 89(6): 2608-15.

Dimatteo, et al (2010) EUS-guided Nd: YAG laser ablation of normal pancreatic tissue: a pilot study in a pig model, Gastrointest. Endosc. 72(2): 358-63.

Doganci, et al, Comparison of 980 nm Laser and Bare-tip Fibre with 1470 nm Laser and Radial Fibre in the Treatment of Great Saphenous Vein Varicosities: A Prospective Randomised Clinical Trial, Eur J Vase Endovasc Surg, 2010, pp. 254-259.

Du, etal, PhotochemCAD: A Computer-Aided Design and Reseach Tool in Photochemistry, Photochemisty and Photobiology, 1998, 68(2), pp. 141-142.

Dunst, et al, Diffuse Phlegmonous Phlebitis After Endovenous Laser Treatment of the Greater Saphenous Vein, Journal of Vascular Surgery, vol. 43 No. 5, 2006, pp. 1056-1058.

Elias, et al, Treating the Small Saphenous Vein, Endovascular Today, Aug. 2008, pp. 60-64.

Endovascular Today, Supplement to Endovascular Today, Nov./Dec. 2004, pp. S1-S35.

Esenaliev, R.O., et al, Laser Ablation of Atherosclerotic Blood Vessel Tissue Under Various Irradiation Conditions, IEEE Transactions on Biomedical Engineering, vol. 36, No. 12, (Dec. 1989) pp. 1188-1194.

European Notice of Allowance issued in App. No. EP19177412, dated Nov. 22, 2023, 40 pages.

Fleischer and Sharma (2008) Endoscopic Ablation of Barrett's Esophagus Using the Halo System. Dig Dis 26(4): 280-284.

Fleischer and Sharma (2009) Endoscopic Ablation of Barrett's Esophagus Using the Halo® System. Dig Dis 26(4): 280-284.

Fleischer and Sharma, Endoscopic Ablation of Barrett's Esophagus Using the Halo® System. Mönkemüller K, Wilcox CM, Muñoz-Navas M (eds): Interventional and Therapeutic Gastrointestinal Endoscopy. Front Gastrointest Res. Basel, Karger, 2010, vol. 27, pp. 140-146.

Grundfest et al., (1985) Pulsed ultraviolet lasers and the potential for safe laser angioplasty. Am J Surg 150(2): 220-226.

Herzog, Amir et al., Spatial-coherence effect on damage occurrence in multimode optical fibers using nanosecond pulses, Advanced Photonics © 2014 OSA, 1 page.

Hongbao, Ma et al., Interaction of excimer laser with blood components and thrombosis, Life Science Journal, vol. 5, Mo 3, 2008, 8 pages.

International Preliminary Report on Patentability, PCT/IL2017/050498, Nov. 6, 2018, 7 pages.

International Search Report 03763292_SESR, dated Jan. 28, 2010.

International Search Report 04256733 ESR, dated Jan. 14, 2005.

International Search Report EP03252158_AESR dated Aug. 29, 2003, 1 page.

International Search Report for PCT/IL2015/050480 Completed Oct. 19, 2015; Mailed Oct. 21, 2015, 6 pages.

International Search Report PCT-US-03-21213 ISR, dated Mar. 29, 2004.

International Search Report PCT-US-08-059791 IPRP, dated Nov. 4, 2008.

International Search Report PCT-US-08-059791 ISR, dated Nov. 4, 2008.

International Search Report PCT-US-08-059791 WOSA, Nov. 4, 2008.

International Search Report PCT/IL2017/050498 Completed Aug. 15, 2017; Mailed Sep. 10, 2017, 4 pages.

International Search Report, PCT/IB2014/058688, Jun. 15, 2014, 5 pages.

International Search Report, PCT/IL2012/000088, Jul. 17, 2012, 2 pages.

International Search Report, PCT/IL2012/000089, Jul. 13, 2012, 2 pages.

International Search Report, PCT/IL2015/050529, Sep. 16, 2015, 5 pages.

International Search Report, PCT/IL2017/050498, Nov. 17, 2017, 4 pages.

Jackson (2009) High-power and highly efficient diode-cladding-pumped holmium-doped flouride fiber laster operating at 2.94 microm. Opt Lett 34(15):2327-2329.

Jackson et al., (2007) Directly diode-pumped holmium fiber lasers. Optics Letters 32(17): 2496-2498.

Jansen, E. Duco et al., Excimer, Ho: YAG, and Q-switched Ho: YAG ablation of aorta: a comparison of temperatures and tissue damage in vitro, Applied Optics, vol. 32, No. 4, Feb. 1, 1993, 9 pages.

Kabnick, et al, EVL Ablation Using Jacket-Tip Laser Fibers, Endovascular Today, Jul. 2009, pp. 77-81.

Leopardi, et al., Systematic Review of Treatments for Varicose Veins, Ann Vasc Surg 2009: 23:264-276.

Litvack, et al, (1988) Pulsed laser angioplasty: wavelength power and energy dependencies relevant to clinical application. Lasers Surg Med 8(1): 60-65.

Mackay, et al, Saphenous Vein Ablation, Endovascular Today, Mar. 2006, pp. 44-48.

Memetoglu, et al, Combination Technique of Tumescent Anesthesia During Endovenous Laser Therapy of Saphenous Vein Insufficiency, Interactive Cardiovascular and Thoracic Surgery 11, 2010, pp. 774-778.

Min, et al, Endovenous Laser Treatment of Saphenous Vein Reflux: Long-Term Results, J Vasc Interv Radiol 2003, 14:991-996.

Min, et al, Endovenous Laser Treatment of the Incompetent Greater Saphenous Vein, J Vasc Interv Radiol 2001, 12:1167-1171.

Murphy-Chutorian et al., (1985) Selective absorption of ultraviolet laser energy by human atherosclerotic plaque treated with tetracycline. Am J Cardiol 55(11): 1293-1297.

Neev, Joseph, Ph. D., Two-Lasers Assisted Ablation: A Method for Enhancing Conventional Laser Ablation of Materials, Lasers in Surgery and Medicine 19:130-134 (1996).

Oraevsky, Alexander A., Plasma Mediated Ablation of Biological Tissues with Nanosecond-to-Femtosecond Laser Pulses: Relative Role of Linear and Nonlinear Absorption, IEEE Journal of Selected Topics in Quantum Electronics, vol. 2, No. 4, Dec. 1996, 9 pages.

* cited by examiner

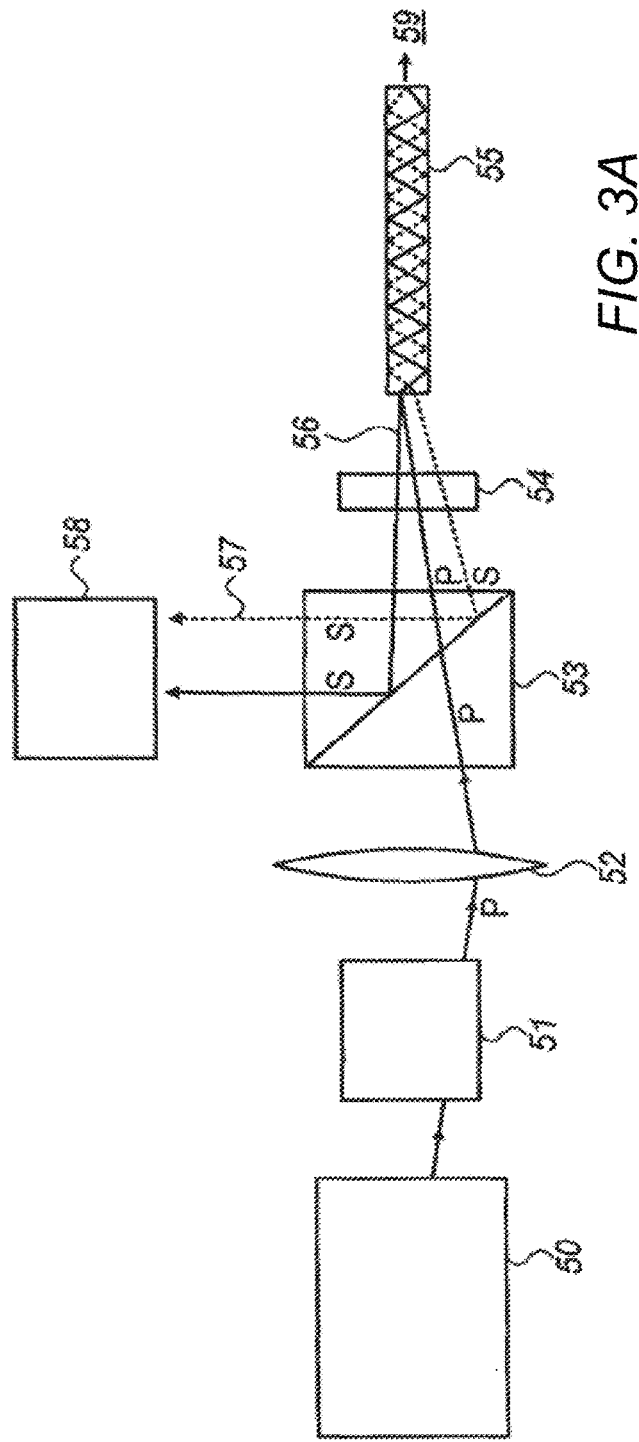
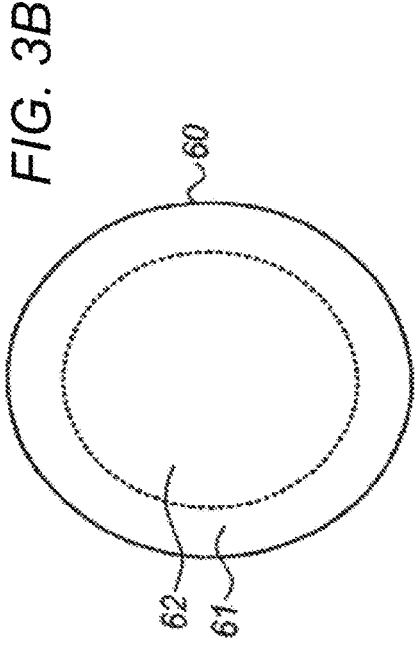
FIG. 3A
FIG. 3B

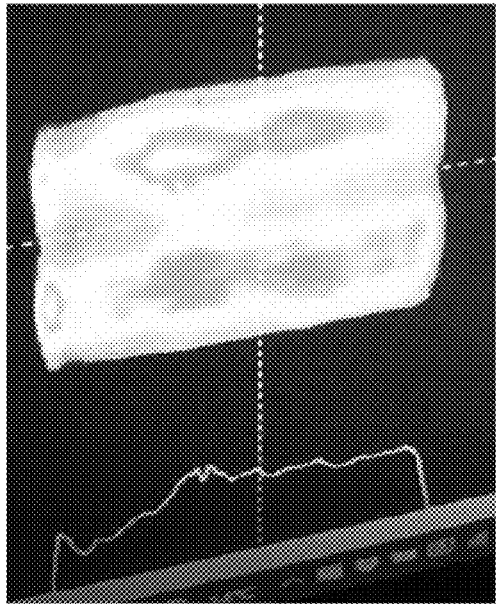 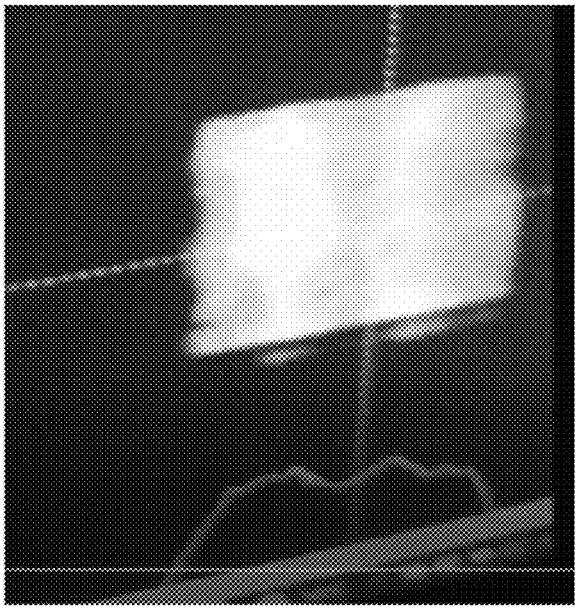
FIG. 18A    FIG. 18B
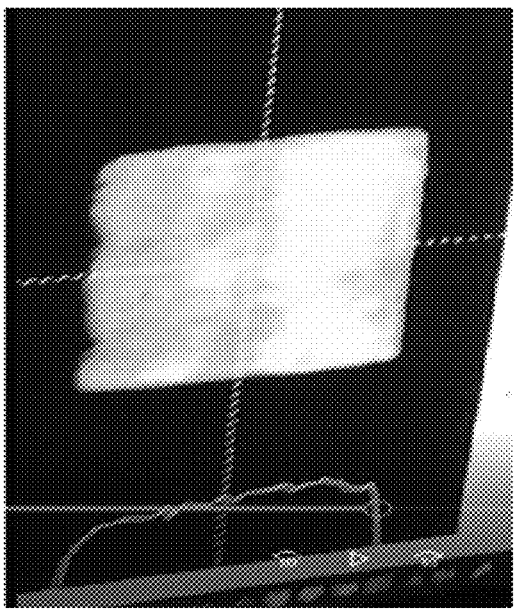 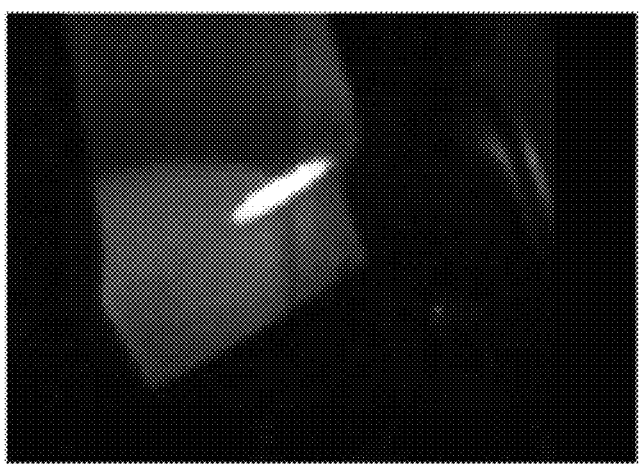
FIG. 18C    FIG. 18D

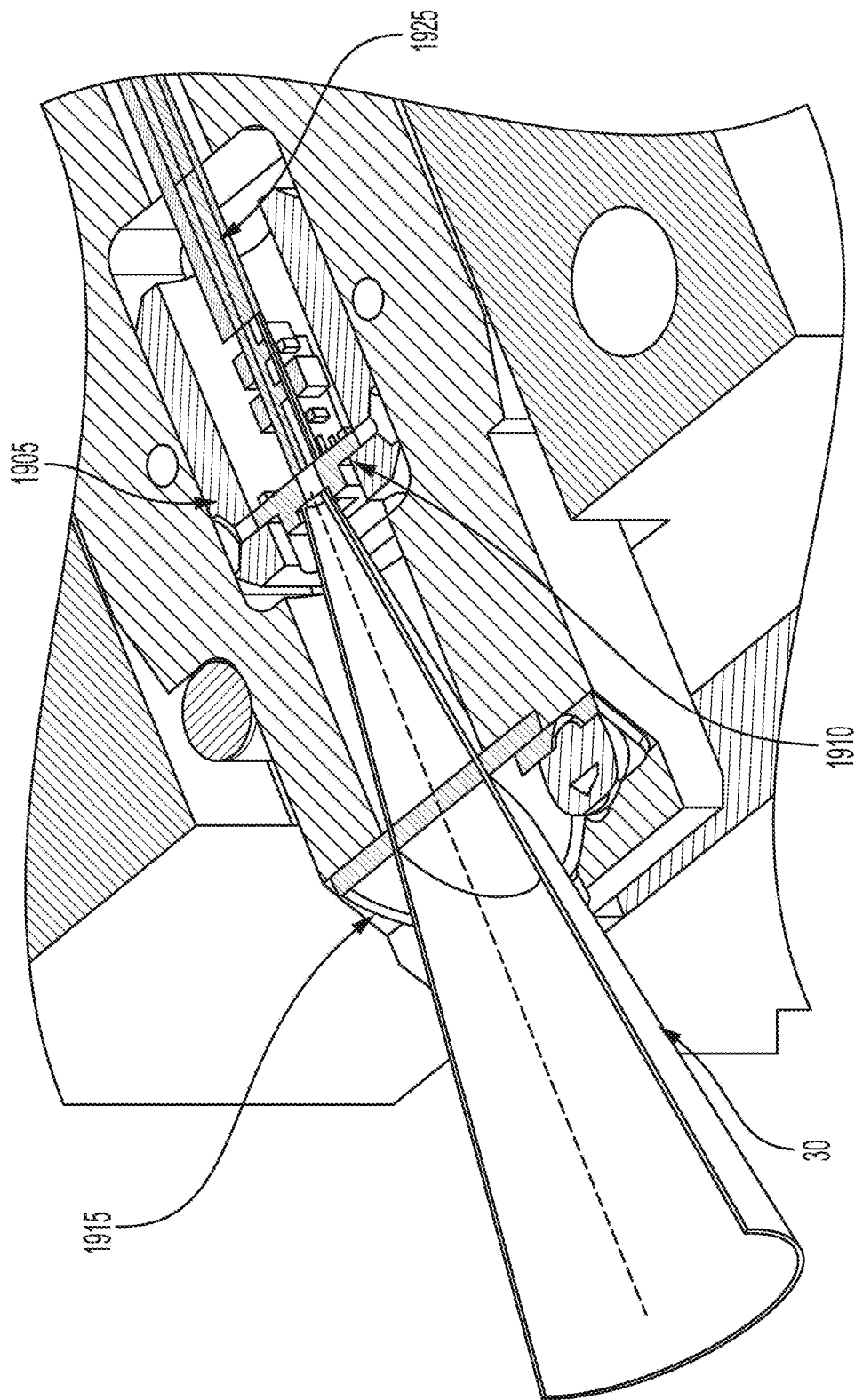

DEVICES AND METHODS FOR TESTING ABLATION SYSTEMS

CROSS-REFERENCE TO RELATED APPLICATIONS

This application claims the benefit of priority to U.S. Provisional Application No. 63/354,081 entitled "Camera and Sensor Jig," filed Jun. 21, 2022, which is incorporated herein by reference in its entirety.

TECHNICAL FIELD

The present disclosure relates generally to methods, systems, and apparatuses related to testing an ablation system. More particularly, the present disclosure relates to methods and systems for assessing a laser beam emitted from an optical box of an ablation system in order to identify issues therewith during manufacturing during quality assurance procedures and/or prior to an ablation procedure. The disclosed techniques may be applied to various types of devices for ablation of a target tissue using an energy source.

BACKGROUND

Delivery of high pulsed laser power through optical fibers is widely used for ablation of tissue or other targets. For such ablation procedures, ultra-violet (UV) light and/or other laser light has many advantages, as it is well absorbed by biological matter and organic compounds. Rather than burning or cutting material, the laser energy is strongly absorbed and results in generation of strong mechanical forces leading to photo-acoustic ablation. Thus, lasers emitting in the ultraviolet have the useful property that they can remove exceptionally fine layers of surface material with almost no heating or change to the remainder of the surrounding material which is left intact.

In order to obtain effective tissue ablation, fluencies above a certain threshold are required, and high peak power pulses, of the order of 50 mJ/mm$^2$ in pulses of down to the 10 nanosecond range are generally desired. The delivery of such fluences can be challenging and may require specialized laser systems comprising a series of optical components configured to generate a modified laser beam (e.g., as disclosed in. U.S. patent application Ser. No. 15/309,193), and such specialized laser systems may require careful calibration and/or maintenance of the optical components. Furthermore, it may be necessary to ensure that the specially configured optical components are properly functioning and aligned prior to performing an ablation procedure. Improper alignment or non-functioning optical components may lead to not modifying a laser beam with sufficient treatment parameters thereby delivering insufficient energy, which may result in incomplete and/or insufficient ablation of the target site. Conversely, improper alignment or non-functioning optical components may lead to excess energy delivery, which may result in an unwanted ablation and/or damage to surrounding structures or tissues beyond the target site.

Determining whether a series of optical components with an optical box are properly aligned (e.g., in a hospital setting or an office-based lab) is currently performed by connecting a testing catheter to the optical box and measuring the energy being emitted. If the emitted energy is within specification, the series of optical components within the optical box is aligned (or the misalignment is negligible) and no adjustments to the optical components are needed. If there is an energy drift of up to approximately 10%, the laser energy can be increased by adjusting the laser output power instead of opening the optical box and re-aligning the system. Generally, it is preferable to avoid opening the optical box in the field due to the complex nature of the optical box and the potential for damage to components therein. If a drift of more than 10% is present, the optical box is typically opened to determine the issue causing the drift and to repair, replace and/or clean one or more components within the optical box.

For example, a testing catheter having a 1.5 mm diameter at its tip and a 100 micron optical fiber array can be used to test the energy drift with an energy density of approximately 50 mJ/mm 2 or 60 mJ/mm$^2$ applied. Where an energy density of 50 mJ/mm$^2$ is applied, an output energy of approximately 25 mJ is within specification and where an energy density of 60 mJ/mm$^2$ is applied, an output energy of approximately 27 mJ is within specification. It is to be understood, however, that various sizes of testing catheters can be used. In some cases, it may be desirable to use a larger testing catheter to allow for a larger beam size that is easier to measure.

However, these methods may be disadvantageous because detected energy drift may be due to degradation of the testing catheter. Where the output energy is measured lower than specification, it may be desirable to verify whether catheter degradation is an issue. As such, a second testing catheter or a clinical catheter is connected to the system/optical box to determine whether the energy is within specification. If the energy of the second testing catheter is within specification, then the issue relative to the first testing catheter is likely due to catheter degradation. If the energy of the second testing catheter is not within specification, then the issue is likely the optical box. Such procedures may be expensive due to the cost associated with testing catheters, especially where multiple testing catheters are required.

Still further, even where issues associated with the testing catheter are ruled out, the energy drift may be associated with a variety of different issues within the system including but not limited to optical box misalignment, laser issues, internal sensor issues, misalignment of connector housing, spot on spot misalignment, damage to a microlens, beam cut on an aperture of an optical element, and dirty optical elements. Although measurement of energy drift may indicate a system failure, it does not provide a clear diagnosis of the failure mode without opening the optical box, which may cause additional issues and/or damage. In many cases, it may not be possible to fix the problem on site in the field. For example, if there is damage on the microlens array (MLA), there will not always be such a replacement module available in the field such that opening the optical box poses an unnecessary risk. On the other hand, if the issue results from connector housing movement, this can be rectified in the field by opening the box, and it would be beneficial to do so. Likewise, if the issue is that optical components are merely dirty, it is easy to clean the optical components. As such, it would be beneficial to identify the particular failure mode so that the optical box may be opened only when there is benefit to doing so in the field.

There is also a need to ensure proper alignment of the system components in the production line at manufacturing, for example, to ensure the microlens array module (MLAM) is correctly aligned in the z-axis. Currently, this is performed by energy measurement during movement along the z-axis. However, energy changes during this movement are less noticeable and more difficult to identify. It would be advantageous to more easily identify z-axis alignment during production and manufacturing of the optical box.

As such, it would be advantageous to have a tool for testing ablation systems and diagnosing the root cause of an energy drift outside of specification or system failure. Such a tool would enable identification of the failure mode in the ablation system, assist in decision making associated with rectification of any failure, and, in some cases, facilitate on site rectification of the failure. Such a tool would also enable testing of the catheter during or after manufacturing thereof for quality assurance purposes. Accordingly, issues present in an ablation system could be identified and/or addressed prior to leaving the manufacturing facility, thereby avoiding issues associated with transporting an ablation system with misaligned components to a clinical site.

SUMMARY

A qualitative beam assessment device is disclosed. The qualitative beam assessment device is configured to interface with an ablation system comprising an optical box and a catheter connector. The qualitative beam assessment device comprises: a housing sized and configured to be received by the catheter connector; a camera coupled to the housing and configured to record an image of a beam emitted by the optical box, wherein the camera is arranged and configured to align with a focal plane of the optical box when the housing is received by the catheter connector; and a communication component in electrical communication with the camera, wherein the communication component is configured to transmit the recorded image from the camera to a processor.

According to some embodiments, the qualitative beam assessment device further comprises an attenuator arranged and configured to attenuate the beam emitted by the optical box before reaching the camera.

According to some embodiments, the housing has a diameter of about 18 mm at an insertion portion configured to be received by the catheter connector.

According to some embodiments, a portion of the camera is optically exposed within the focal plane of the optical box when the housing is received by the catheter connector.

According to some embodiments, the qualitative beam assessment device further comprises an RFID chip configured to communicate with the ablation system, wherein the RFID chip is configured to instruct the ablation system to reduce an energy density of the beam emitted from the optical box.

A quantitative beam assessment device is disclosed. The quantitative beam assessment device is configured to interface with an ablation system comprising an optical box and a catheter connector. The qualitative beam assessment device comprises: a housing sized and configured to be received by the catheter connector; an energy sensor coupled to the housing and configured to measure an energy of a beam emitted by the optical box; a guiding component coupled to the housing and configured to direct the beam emitted by the optical box to the energy sensor, wherein the guiding component is arranged and configured to align with a focal plane of the optical box when the housing is received by the catheter connector; and a communication component in electrical communication with the energy sensor, wherein the communication component is configured to transmit the measurement from the energy sensor to a processor.

According to some embodiments, the energy sensor comprises a thermoelectric cooler.

According to some embodiments, the guiding component is selected from the group consisting of a shutter, a waveguide, and a square core fiber.

According to some embodiments, the housing has a diameter of about 18 mm at an insertion portion configured to be received by the catheter connector.

According to some embodiments, a portion of the energy sensor is optically exposed within the focal plane of the optical box when the housing is received by the catheter connector.

A system for testing an ablation system is disclosed. The ablation system comprises an optical box and a catheter connector. The system comprises: a qualitative beam assessment device comprising a first housing sized and configured to be received by the catheter connector and a camera configured to record one or more signals related to a beam profile of a beam emitted by the optical box, wherein the camera is arranged and configured to align with a focal plane of the optical box when the housing is received by the catheter connector; a quantitative beam assessment device comprising a second housing sized and configured to be received by the catheter connector, an energy sensor coupled to the housing and configured to measure a beam energy of the beam emitted by the optical box, and a guiding component coupled to the housing and configured to direct the beam emitted by the optical box to the energy sensor, wherein the guiding component is arranged and configured to align with the focal plane of the optical box when the housing is received by the catheter connector; a processor configured to electrically communicate with each of the qualitative beam assessment device and the quantitative beam assessment device; and a non-transitory, computer-readable medium storing instructions that, when executed, cause the processor to: receive, from the qualitative beam assessment device, the one or more signals related to the beam profile, determine, based on the one or more signals related to the beam profile, a qualitative condition of the beam, receive, from the quantitative beam assessment device, the one or more signals related to the beam energy, and determine, based on the one or more signals related to the beam energy, a quantitative condition of the beam.

According to some embodiments, the qualitative beam assessment device further comprises an attenuator arranged and configured to attenuate the beam emitted by the optical box before reaching the camera.

According to some embodiments, each of the first housing and the second housing has a diameter of about 18 mm at an insertion portion configured to be received by the catheter connector.

According to some embodiments, the first housing and the second housing are each configured to be selectively received at a first portion of the catheter connector.

According to some embodiments, the system further comprises a display device in electrical communication with the processor. According to additional embodiments, the instructions, when executed, further cause the processor to display at least one of the determined qualitative condition and the determined quantitative condition on the display device.

According to some embodiments, the qualitative condition comprises a failure mode of the ablation system. According to additional embodiments, the failure mode comprises misalignment of the beam. According to further embodiments, the misalignment of the beam is selected from the group consisting of: blocking of an S-polarized beam of the beam from entering an optical element of the optical box, wherein the beam comprises an S-polarized beam and a P-polarized beam; misalignment of a mirror of the optical box; shifting of the S-beam; misalignment in the Z-direction from a focal point of the optical box; and misalignment of the catheter connector. According to additional embodiments, the failure mode is selected from the group consisting of misalignment of the beam, damage to the an optical element, failure of a laser of the ablation system, failure of a sensor of the ablation system, cutting of the beam, misalignment of a P-beam and an S-beam of the beam, a dirty optical element of the optical box, misalignment of the catheter connector in the X-Y plane, misalignment of the catheter connector in the Z-direction, low overall energy, and improper energy distribution.

BRIEF DESCRIPTION OF THE DRAWINGS

The accompanying drawings, which are incorporated in and form a part of the specification, illustrate the embodiments of the invention and together with the written description serve to explain the principles, characteristics, and features of the invention. Various aspects of at least one example are discussed below with reference to the accompanying drawings, which are not intended to be drawn to scale. In the drawings:

FIGS. 3A-3B depict a schematic view of an arrangement for calibrating a catheter in accordance with an embodiment.

FIGS. 18A-18D depict beam profiles where the overlapping P+S beam is shifted by detuning the final mirror of the optical box in the y- and x-directions in accordance with an embodiment.

FIG. 19B depicts a cross-sectional top-down view of the connector housing with the camera jig inserted therein, and showing the mirror/beam separator with respect to the camera in accordance with an embodiment.

DETAILED DESCRIPTION

Figure 1:
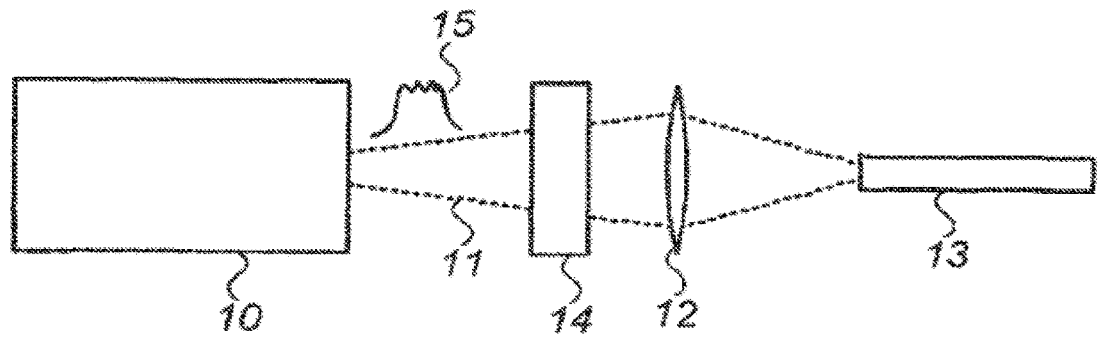
FIG. 1 depicts a schematic view of an exemplary tissue ablation system in accordance with an embodiment.

This disclosure is not limited to the particular systems, devices and methods described, as these may vary. The terminology used in the description is for the purpose of describing the particular versions or embodiments only, and is not intended to limit the scope. Such aspects of the disclosure can be embodied in many different forms; rather, these embodiments are provided so that this disclosure will be thorough and complete, and will fully convey its scope to those skilled in the art.

As used in this document, the singular forms "a," "an," and "the" include plural references unless the context clearly dictates otherwise. With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity.

As will be understood by one skilled in the art, for any and all purposes, such as in terms of providing a written description, all ranges disclosed herein are intended as encompassing each intervening value between the upper and lower limit of that range and any other stated or intervening value in that stated range. All ranges disclosed herein also encompass any and all possible subranges and combinations of subranges thereof. Any listed range can be easily recognized as sufficiently describing and enabling the same range being broken down into at least equal halves, thirds, quarters, fifths, tenths, et cetera. As a non-limiting example, each range discussed herein can be readily broken down into a lower third, middle third and upper third, et cetera. As will also be understood by one skilled in the art all language such as "up to," "at least," and the like include the number recited and refer to ranges that can be subsequently broken down into subranges as discussed above. Finally, as will be understood by one skilled in the art, a range includes each individual member. Thus, for example, a group having 1-3 cells refers to groups having 1, 2, or 3 cells as well as the range of values greater than or equal to 1 cell and less than or equal to 3 cells. Similarly, a group having 1-5 cells refers to groups having 1, 2, 3, 4, or 5 cells, as well as the range of values greater than or equal to 1 cell and less than or equal to 5 cells, and so forth.

In addition, even if a specific number is explicitly recited, those skilled in the art will recognize that such recitation should be interpreted to mean at least the recited number (for example, the bare recitation of "two recitations," without other modifiers, means at least two recitations, or two or more recitations). Furthermore, in those instances where a convention analogous to "at least one of A, B, and C, et cetera" is used, in general such a construction is intended in the sense one having skill in the art would understand the convention (for example, "a system having at least one of A, B, and C" would include but not be limited to systems that have A alone, B alone, C alone, A and B together, A and C together, B and C together, and/or A, B, and C together, et cetera). In those instances where a convention analogous to "at least one of A, B, or C, et cetera" is used, in general such a construction is intended in the sense one having skill in the art would understand the convention (for example, "a system having at least one of A, B, or C" would include but not be limited to systems that have A alone, B alone, C alone, A and B together, A and C together, B and C together, and/or A, B, and C together, et cetera). It will be further understood by those within the art that virtually any disjunctive word and/or phrase presenting two or more alternative terms, whether in the description, sample embodiments, or drawings, should be understood to contemplate the possibilities of including one of the terms, either of the terms, or both terms. For example, the phrase "A or B" will be understood to include the possibilities of "A" or "B" or "A and B."

In addition, where features of the disclosure are described in terms of Markush groups, those skilled in the art will recognize that the disclosure is also thereby described in terms of any individual member or subgroup of members of the Markush group.

By hereby reserving the right to proviso out or exclude any individual members of any such group, including any sub-ranges or combinations of sub-ranges within the group, that can be claimed according to a range or in any similar manner, less than the full measure of this disclosure can be claimed for any reason. Further, by hereby reserving the right to proviso out or exclude any individual substituents, structures, or groups thereof, or any members of a claimed group, less than the full measure of this disclosure can be claimed for any reason.

The term "about," as used herein, refers to variations in a numerical quantity that can occur, for example, through measuring or handling procedures in the real world; through inadvertent error in these procedures; through differences in the manufacture, source, or purity of compositions or reagents; and the like. Typically, the term "about" as used herein means greater or lesser than the value or range of values stated by $1/10$ of the stated values, e.g., ±10%. The term "about" also refers to variations that would be recognized by one skilled in the art as being equivalent so long as such variations do not encompass known values practiced by the prior art. Each value or range of values preceded by the term "about" is also intended to encompass the embodiment of the stated absolute value or range of values. Whether or not modified by the term "about," quantitative values recited in the present disclosure include equivalents to the recited values, e.g., variations in the numerical quantity of such values that can occur, but would be recognized to be equivalents by a person skilled in the art. Where the context of the disclosure indicates otherwise, or is inconsistent with such an interpretation, the above-stated interpretation may be modified as would be readily apparent to a person skilled in the art. For example, in a list of numerical values such as "about 49, about 50, about 55, "about 50" means a range extending to less than half the interval(s) between the preceding and subsequent values, e.g., more than 49.5 to less than 52.5. Furthermore, the phrases "less than about" a value or "greater than about" a value should be understood in view of the definition of the term "about" provided herein.

It will be understood by those within the art that, in general, terms used herein are generally intended as "open" terms (for example, the term "including" should be interpreted as "including but not limited to," the term "having" should be interpreted as "having at least," the term "includes" should be interpreted as "includes but is not limited to," et cetera). Further, the transitional term "comprising," which is synonymous with "including," "containing," or "characterized by," is inclusive or open-ended and does not exclude additional, unrecited elements or method steps. While various compositions, methods, and devices are described in terms of "comprising" various components or steps (interpreted as meaning "including, but not limited to"), the compositions, methods, and devices can also "consist essentially of" or "consist of" the various components and steps, and such terminology should be interpreted as defining essentially closed-member groups. By contrast, the transitional phrase "consisting of" excludes any element, step, or ingredient not specified in the claim. The transitional phrase "consisting essentially of" limits the scope of a claim to the specified materials or steps "and those that do not materially affect the basic and novel characteristic(s)" of the claimed invention.

The terms "patient" and "subject" are interchangeable and refer to any living organism which contains neural tissue. As such, the terms "patient" and "subject" may include, but are not limited to, any non-human mammal, primate or human. A subject can be a mammal such as a primate, for example, a human. The term "subject" includes domesticated animals (e.g., cats, dogs, etc.); livestock (e.g., cattle, horses, swine, sheep, goats, etc.), and laboratory animals (e.g., mice, rabbits, rats, gerbils, guinea pigs, possums, etc.). A patient or subject may be an adult, child or infant.

The term "tissue" refers to any aggregation of similarly specialized cells which are united in the performance of a particular function.

The term "disorder" is used in this disclosure to mean, and is used interchangeably with, the terms "disease," "condition," or "illness," unless otherwise indicated.

The term "real-time" is used to refer to calculations or operations performed on-the-fly as events occur or input is received by the operable system. However, the use of the term "real-time" is not intended to preclude operations that cause some latency between input and response, so long as the latency is an unintended consequence induced by the performance characteristics of the machine.

The terms "$M^2$ parameter" and "$M^2$" are used herein to characterize the beam mode quality of a laser output beam. The $M^2$ parameter is one parameter used for characterizing the beam mode quality, e.g., to characterize the beam properties for achievement of very high pulse energy densities for such pulses in the nanosecond range. However, it is to be understood that other parameters or metrics may be used to characterize beam quality. The mode quality of a laser output beam can be characterized by the beam size and beam divergence, wherein beam quality increases as the divergence decreases for a beam of given size and wavelength. The $M^2$ parameter is related to the ratio of the output beam size and the beam divergence according to the following relationship:

$$M^2 = \frac{D\theta\pi}{4\lambda}$$

where D is the beam diameter, λ is the wavelength of the laser beam, and θ is the full angle beam divergence in radians. A diffraction-limited beam would have an $M^2$ parameter of 1, while practical, high-efficiency, commercial lasers for use in surgical or precision industrial applications generally have an $M^2$ parameter in the low single digit range. The $M^2$ parameter can also be defined for a beam at any point along its optical path, by inserting a focusing lens at that point and measuring the size of the focal spot obtained. Intuitively, if the focal spot is tighter, the mode quality of the beam at that point is better, and the $M^2$ parameter is lower. The $M^2$ parameter in that case is given by the following relationship:

$$M^2 = \frac{Dd\pi}{4f\lambda}$$

where D is the beam diameter at the point of insertion of the lens, f is the focal length of the lens, d is the size of the focal spot obtained, and λ is the wavelength of the laser beam. It is to be understood throughout this disclosure that the $M^2$ parameter is calculated according to the appropriate formula, depending on whether the measurement relates to the laser output beam or to a beam downstream in the optical path.

The terms "optical box" and/or "laser system" are interchangeably used herein to refer to a housing containing optical elements and/or lasers of the ablation system. The terms "optical box" and/or "laser system" may refer to the housing as well as the components housed therein. For example, an optical box may include a laser, a coupling lens, a microlens array module (MLAM), additional mirrors, a half wave plate, and/or a beam splitter (see, e.g., FIG. 2). The housing forming the optical box may also include a catheter connector for connecting to a catheter and other mechanical components or structures. Additional details and description of optical boxes and/or laser systems are disclosed in U.S. patent application Ser. No. 14/001,633, now issued as U.S. Pat. No. 9,730,756, U.S. patent application Ser. No. 15/309,193, and U.S. patent application Ser. No. 16/592,725, now issued as U.S. Pat. No. 10,772,683, each of which is incorporated herein by reference in its entirety.

Unless defined otherwise, all technical and scientific terms used herein have the same meanings as commonly understood by one of ordinary skill in the art. Nothing in this disclosure is to be construed as an admission that the embodiments described in this disclosure are not entitled to antedate such disclosure by virtue of prior invention.

Throughout this disclosure, various patents, patent applications and publications are referenced. The disclosures of these patents, patent applications and publications are incorporated into this disclosure by reference in their entireties in order to more fully describe the state of the art as known to those skilled therein as of the date of this disclosure. This disclosure will govern in the instance that there is any inconsistency between the patents, patent applications and publications cited and this disclosure.

In the present disclosure various systems, devices, and methods related to testing an ablation system. Each of the systems, devices, and methods disclosed herein provides one or more advantages over conventional systems, devices, and methods. As discussed herein, it would be advantageous to have a tool for testing ablation systems and diagnosing failure thereof. Such a tool would enable identification of the failure mode in the ablation system and, in some cases, on site rectification of the failure.

Ablation Systems

Exemplary ablation systems that utilize the calibration apparatuses and methods disclosed herein are first described in greater detail. In an exemplary catheter system, a third harmonic Nd:YAG laser outputting at 355 nm is coupled to a hybrid catheter, which incorporates a bundle of optical fibers receiving laser illumination, and at least one blunt-ended tubular structure whose distal edge is located on an essentially single surface with the output facets of the optical fibers to interact with atheromatous tissue within a blood vessel. Different configurations may be used for lead extraction (LE) procedures and for debulking or opening blood vessels where substantial deposits of atheromatous material is found such as in Peripheral Artery Disease (PAD). In the LE case, a thin annular bundle of fibers is required, with cylindrical walls bounding it on the inner and outer sides of the annulus. The cylindrical walls constitute the blunt-ended tubular structure. On the other hand, in PAD, for removal of deposits across the whole cross-section of a blood vessel, the bundle of fibers essentially covers the whole of the cross section of the catheter, usually with a thin opening in the center of the bundle for a guide wire. Even in the case of PAD, the cylindrical walls of the bundle region constitute the blunt ended tubular structure. Throughout this disclosure, these blunt ended tubular structures are termed "blunt mechanical blades."

Using the LE case as an example, the catheter operates, once within the blood vessel and in contact with the intravascular deposit, by using laser pulses to ablate a thin layer of the tissue, typically only a few tens of microns deep, making a thin, shallow slit to enable the continued penetration of the blunt mechanical blade in response to the pressure applied distally on the catheter. The blade or blades are therefore constructed to be too blunt to initiate dissection, but with enough of an edge to create the slit to enable deeper catheter penetration into the tissue. The borders of the tissue being ablated, which possess a transient zone, are mechanically weakened due to the trauma, which facilitates dissection by the blunt blade. The width of the blades, and the ratio of the total area of the cores of the fibers within the fiber optical bundle, from which the ablation energy is emitted, relative to the total cross-sectional area of the tip of the catheter, not including the empty central area, are important parameters which also characterize the catheters of the present disclosure.

The force applied distally on the catheter is an additional parameter for which the level is adjusted to ensure that the catheter advances through the atheromatous tissue at a rate commensurate with the rate of laser ablation and mechanical peeling of the hybrid catheter action. As the diameter of the catheter increases, a larger force needs to be applied.

In some embodiments, the laser pulse is split into at least two pulses with a delay of about 15 nanoseconds (ns) or less between the pulses in order to protect the distal facets of the fibers without significant impact on ablation efficiency.

In some embodiments, the pulsed laser may advantageously be a Nd:YAG solid state laser having a wavelength of 355 nm, a pulse width of about 15 nanoseconds (ns) or less, and a pulse repetition rate of at least about 10 Hz. The fluence of the laser may be at least about 50 $mJ/mm^2$ or approximately 50-60 $mJ/mm^2$. However, in other embodiments, the fluence delivered through the optical fiber may be about 30 $mJ/mm^2$, about 40 $mJ/mm^2$, about 50 $mJ/mm^2$, about 60 $mJ/mm^2$, about 70 $mJ/mm^2$, about 80 $mJ/mm^2$, about 90 $mJ/mm^2$, about 100 $mJ/mm^2$, about 200 $mJ/mm^2$ or about 300 mJ/mm$^2$, or individual values or ranges therebetween. The laser may be delivered through the optical fiber for about one minute or more.

The tissue ablation system is now further described with respect to the optical components therein. FIG. 1 illustrates a schematic view of an exemplary tissue ablation system in accordance with an embodiment. The tissue ablation system comprises a solid state laser source a coupling lens 12 (also referred to as a 'Fourier lens' 12), an optical fiber bundle 13, and a coherence manipulation unit 14.

The solid state laser source 10 is configured to emit light in the ultraviolet (UV) spectrum, i.e., light having a wavelength from about 100 nanometers (nm) to about 400 nm. The solid state laser source 10 may have a multi-mode output, as exemplified in FIG. 1 by the beam profile representation 15 adjacent to the output beam 11. This representation is only for illustrative purposes to show the multi-mode output as being very distant from a Gaussian beam, and is not intended to be limiting. The output beam 11 may have an $M^2$ parameter of at least about 30, and more advantageously at least about 70, though lasers having a beam output with an $M^2$ parameter of over about 100 can provide even better performance. For optimum performance, the laser may emit short pulse widths, e.g., less than or equal to about 10 nanoseconds (ns), and the laser may supply pulses that provide an energy density of at least about 50 mJ/mm$^2$ through the fiber. For stability and compactness, a solid state laser is used, e.g., a Nd:YAG laser, operating at its third harmonic, i.e., about 355 nm.

Although the solid state laser source 10 may emit a well-mixed multimode beam, the laser beam may be input to the coherence manipulation unit 14 (alternatively referred to herein as a beam homogenizing unit 14) in order to mix the multiple modes of the output beam 11 even further, such that the fiber has an even higher damage threshold than would be obtained with the multimode output from the solid state laser source 10 alone. The coherence manipulation unit 14 may be a homogenizing plate, a diffractive optical element, a holographic element, a micro-lens array (MLA), a homogenizer optical fiber, and/or combinations thereof. In the case of a homogenizer optical fiber, the fiber may be bent to ensure additional mode mixing during propagation of the pulses down the fiber. The coupling lens 12 couples the laser beam to the optical fiber bundle 13. The optical fiber bundle contains a large number of individual fibers, each having a core size of less than about 200 microns, and is thus substantially larger than the diameter of the individual fibers. Although only one coupling lens 12 is shown in FIG. 1, it is to be understood that the system could incorporate two coupling lenses, e.g., a first coupling lens 12 to couple the raw laser beam 11 into a homogenizer fiber and a second coupling lens 12 to couple the output of the treated beam into the optical fiber bundle 13 of the catheter.

Figure 2:
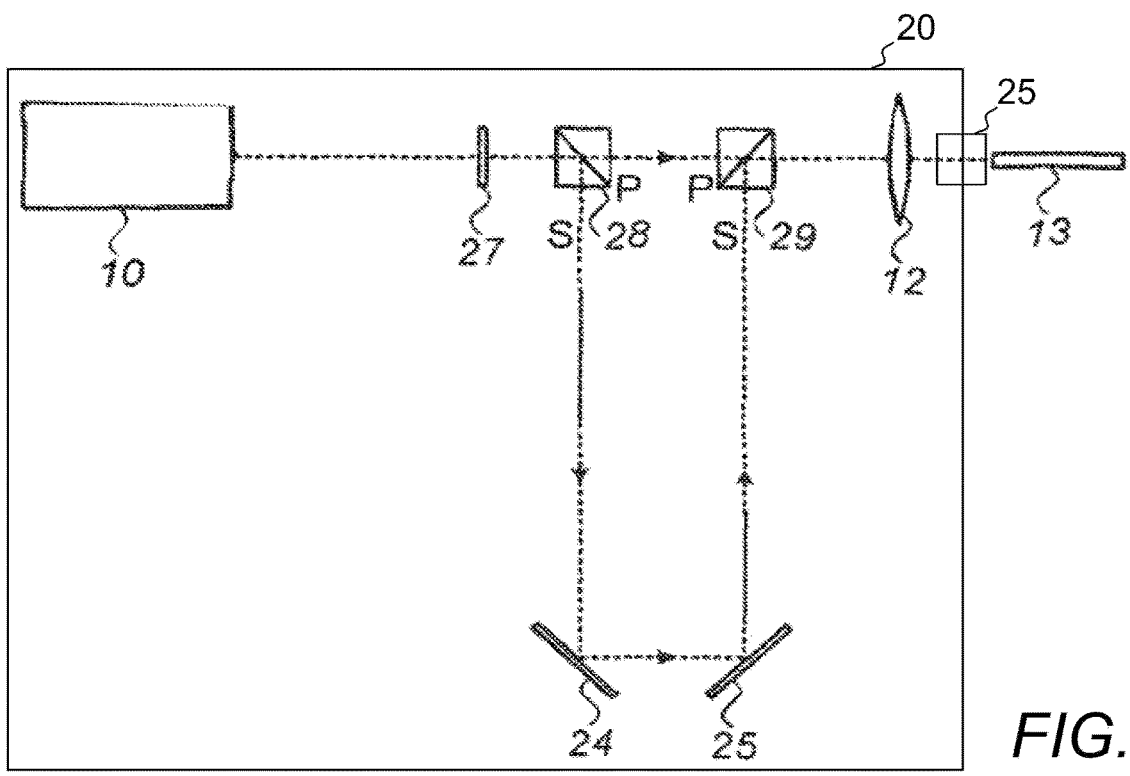
FIG. 2 depicts a schematic view of a further exemplary implementation of the system shown in FIG. 1 in accordance with an embodiment.

FIG. 2 illustrates a schematic view of a further exemplary implementation of the system shown in FIG. 1 in accordance with an embodiment. The system as shown in FIG. 2 implements polarization splitting of the laser beam. Typically, the output facets, i.e., the region where the fibers are in contact with the tissue being ablated, are subject to particularly harsh conditions. Accordingly, the system described in FIG. 1 may have a likelihood of facet damage that is greater at the output facets than at the input facets of the fibers. In order to reduce the danger of damage to the output facet, the system of FIG. 2 implements polarization splitting in order to enable transmission of the pulse train down the fiber in the form of temporally separated double pulses. While this implementation is most beneficial to protect the output facets from damage, it is to be understood that it is also useful for protecting the input facet and the fiber bulk.

The beam from the highly multimode laser 10 is transmitted through a half wave plate 27 and then to a polarization beam splitter 28 in order to split the laser beam into two component parts: an S-polarized component and a P-polarized component. As shown in FIG. 2, the S-polarized component is deflected by 90° while the P-polarized component passes through the cubic beam splitter without deflection. The S-polarized is conveyed on an optical path longer than that of the P-polarized component, and after reflection through 180°, accomplished by means of two full reflector mirrors 24A/24B, the S- and the P-polarized component beams are recombined by means of a second polarization beam splitter 29. The combined beam is then transmitted by the coupling lens 12 into the fibers 13 of the catheter. By adjusting the optical path difference along which the P- and S-polarized components travel, it is possible to control the temporal delay between the two beams such that the input is made up of double pulses, separated by the selected time delay. The use of such a double pulse laser beam reduces the likelihood of fiber damage at the entrance facet of the optical fiber as well as the problematic output facet of the optical fiber that is in contact mode with the ablated material. The time delay may be selected such that the double pulses are not separated by more than the relaxation time of the vascular material being treated, such that ablating efficiency is not lost. For 10 ns pulses, a time delay between pulses of the order of 10 ns is regarded as being acceptable, e.g., about 10 ns, about 15 ns, about 20 ns, or individual values or ranges therebetween. The success of this double pulse mode depends also on the knowledge that the ablation efficiency is not a linear function of peak power of the laser pulse, such that division of the power into two pulses does not degrade the ablation effect by the same factor of two. Additionally, a lens (not shown in FIG. 2) could be disposed in the longer optical paths in order to image the beam waist in such a manner that the waists of the two beams traversing the two different optical paths are both located at the fiber input facet. This is necessary in order to compensate for the extra beam divergence which the beam in the longer optical path undergoes. As an alternative to the configuration shown in FIG. 2, it is possible to use thin film polarizers (TFP) to split and combine the two beams.

Furthermore, the laser beam may split into more than two channels, to even further reduce the potential damage level of the fibers. Additionally, different wavelengths emitted by a laser, such as the second and third harmonics, or the fundamental and third harmonic of the Nd:YAG laser, can be split and combined again. It is also possible to use multiple lasers with a synchronized delay between the pulses.

It should be noted that as shown in FIG. 2, many of the components such as the laser 10, the coupling lens 12, the mirrors 24A/24B, the half wave plate 27, and/or the beam splitter 28 may be collectively referred to as an optical box 20. The optical box 20 may be configured to connect to a catheter (depicted as optical fiber bundle 13) via a catheter connector 25 (also referred to as a 'connector housing' herein).

Reference is now made to FIGS. 3A-3B, which illustrate a schematic view of an arrangement for calibrating a catheter in accordance with an embodiment. Calibration is necessary prior to the operation in order to verify the fluence and the repetition rate of the laser energy that is emitted from the catheters. In the prior art, methods of calibration of catheters have been described in which the catheter is coupled to the laser system, while the distal tip is held by a housing in front of a detector, and the transmitted energy is measured by the detector while the laser is operated. Because the catheters are sterilized before use, this method can involve the risk of moving the distal tip of the catheter out of the sterilized area in the operation room.

The system shown in FIG. 3A enables the internal calibration of the catheter, while it is in use as well as detection of a failure of the system while it is operating. The incident beam from the laser 50 is directed through a beam polarizer 51, which outputs the beam as P-polarized, as marked in FIG. 3A. After traversing the coupling lens 52, the P-polarized beam is input to a polarizing beam splitter 53 from which it emerges undeflected. The P-polarized beam is input through a quarter wave plate 54, which converts its polarization to circular. This circularly polarized beam enters the fiber 55, passing therethrough by total internal reflection (TIR) such that the majority of the energy is emitted from the output facet at the distal end of the fiber for use in the ablation procedure 59. However, a small percentage of the energy is reflected back towards the entrance of the fiber due to Fresnel reflection from the output facet. Additionally, any Fresnel reflection 56 from the front facet is also reflected back. This small, reflected fraction of the input beam now passes back through the quarter wave plate 54, where it is converted from circular into S-polarization, such that when it enters the polarizing beam splitter 53, it is deflected along a path 57 approximately normal to its entrance axis towards the detector 58. Because the percentage reflection from the front and rear facets is known, the detector is able to determine the energy emitted from the fiber output to the ablation application based on a measurement of the reflected energy. The measurement of the detector output is thus a real-time monitor of the laser energy being used in the ablation procedure.

If the entrance facet is coated with an anti-reflective coating, the power measured by the detector 58 is due only to reflection from the output facet, such that differentiation can be made between reflections from these two facets. Alternatively, a spatial filter may be disposed between the front facet and the polarizing beam splitter in order to filter out the reflection from the input facet, which has a smaller divergence angle than the reflection from the output facet because the numerical aperture of the output reflection is significantly larger. The spatial filter may conveniently be a thin film polarizer (TFP) as illustrated in FIG. 3B. The TFP 60 is coated at its peripheral edges 61, such that those edges diverge the reflected beam from the output facet to the detector 58, while the central region 62 of the TFP 60 is uncoated. As such, the smaller divergence reflection from the input facet passes through the central uncoated window and does not reach the detector 58.

In an alternative embodiment, a cap may be placed over the distal tip of the catheter with the inside of the cap coated with reflective coating in order to enhance the signal that is reflected from the distal facets of the fibers. In one example, the cap may be coated with a fluorescent material that changes the wavelength of the output reflected beam such that an optical filter may be used to separate the output reflected beam from the entrance facet reflection. In some embodiments, the cap may be configured to be sterilized together with the catheter. In another example, the cap may also be covered with material, e.g., polyamide, which provides a vocal indication when energy above specified level strikes the cap. In another embodiment, the cup may be covered with material that changes its color when exposed to the radiation of the laser.

In additional embodiments, the entrance facet is not coated such that the detector measures the energy reflected from the input and output facets together.

It should be understood that the above-described calibration procedure can be performed while the fiber is rolled up inside its packaging, thereby keeping the bend radius of the fiber known and constant so that the percent of energy reflected back from the output facet does not change.

In some embodiments, the system can be internally calibrated without connecting the catheter. A lid may be moved aside when the catheter is connected and closed when the catheter is moved out. This lid is mirror coated at the side that is pointing to the laser, and the energy reflected from this mirror coating is folded by the polarized beam splitter and can be measured in the detector.

The described method of calibrating catheters also enables real-time monitoring of the ablation process by measuring the reflected energy in the system detector during the procedure and informing the user about energy degradation due to fiber damage.

Additional details and description of tissue ablation systems and calibration methods therefor are disclosed in U.S. patent application Ser. No. 14/001,633, now issued as U.S. Pat. No. 9,730,756, U.S. patent application Ser. No. 15/309,193, and U.S. patent application Ser. No. 16/592,725, now issued as U.S. Pat. No. 10,772,683, each of which is incorporated herein by reference in its entirety.

Beam Assessment Devices for Testing Ablation Systems

As discussed herein, ablation systems may be routinely tested and/or monitored to ensure proper functioning of the optical box 20, the catheter 13, and other components (see FIG. 2) to enable effective and accurate energy delivery to a target site (e.g., undesirable material and/or other tissue). Typically, ablation procedures or treatment plans for patients may be complex and may require specific quantities of energy to be delivered to the target site. Insufficient energy may result in incomplete and/or insufficient ablation of the target site. Conversely, excess energy may result in ablation and/or damage to surrounding structures or tissues beyond the target site. Conventional methods of testing ablation systems include measuring the energy output through testing catheters to detect energy drift relative to specification. However, these methods may be disadvantageous because detected energy drift may be due to degradation of the testing catheter; additional testing catheters may be required to test the efficiency of the testing catheters in order to rule out catheter degradation. Furthermore, testing catheters may be expensive and may increase costs associated with an ablation procedure.

Still further, even where issues associated with the testing catheter are ruled out, the energy drift may be associated with a variety of different issues within the system including but not limited to optical box misalignment, laser issues, internal sensor issues, misalignment of connector housing, spot on spot misalignment, damage to a microlens, beam cut on an aperture of an optical element, and dirty optical elements. Although measurement of energy drift may indicate a system failure, it does not provide a clear diagnosis of the failure mode without opening the optical box, which may cause additional issues and/or damage.

As such, it would be advantageous to have a tool for testing ablation systems and diagnosing failure thereof. Such a tool would enable identification of the failure mode in the ablation system and, in some cases, on-site rectification of the failure.

Figure 4A:
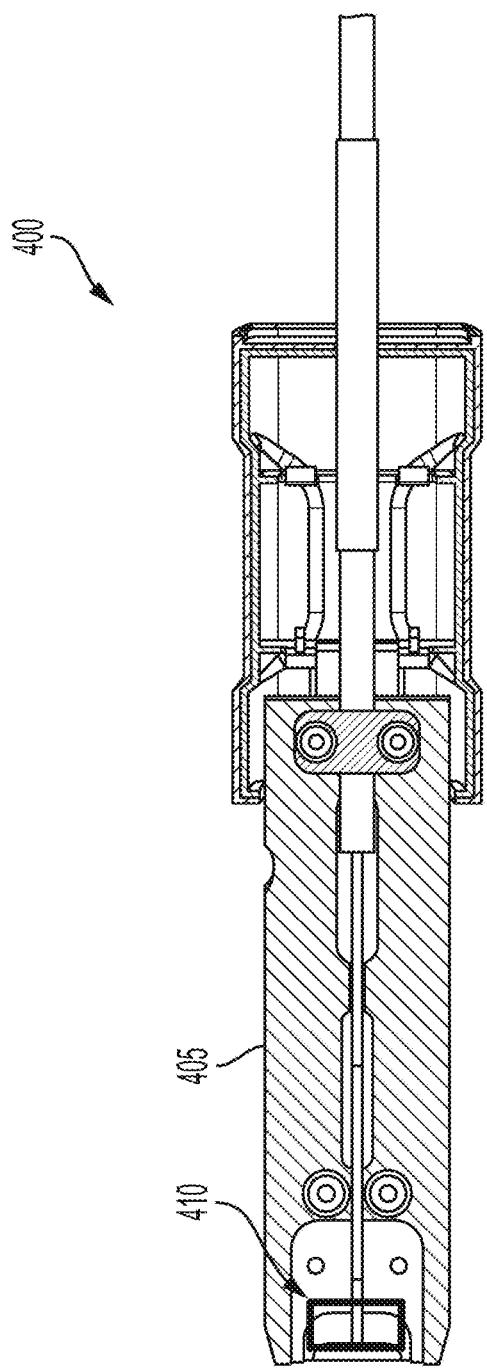
FIG. 4A depicts a first beam assessment device for testing an ablation system in accordance with an embodiment.
Figure 4B:
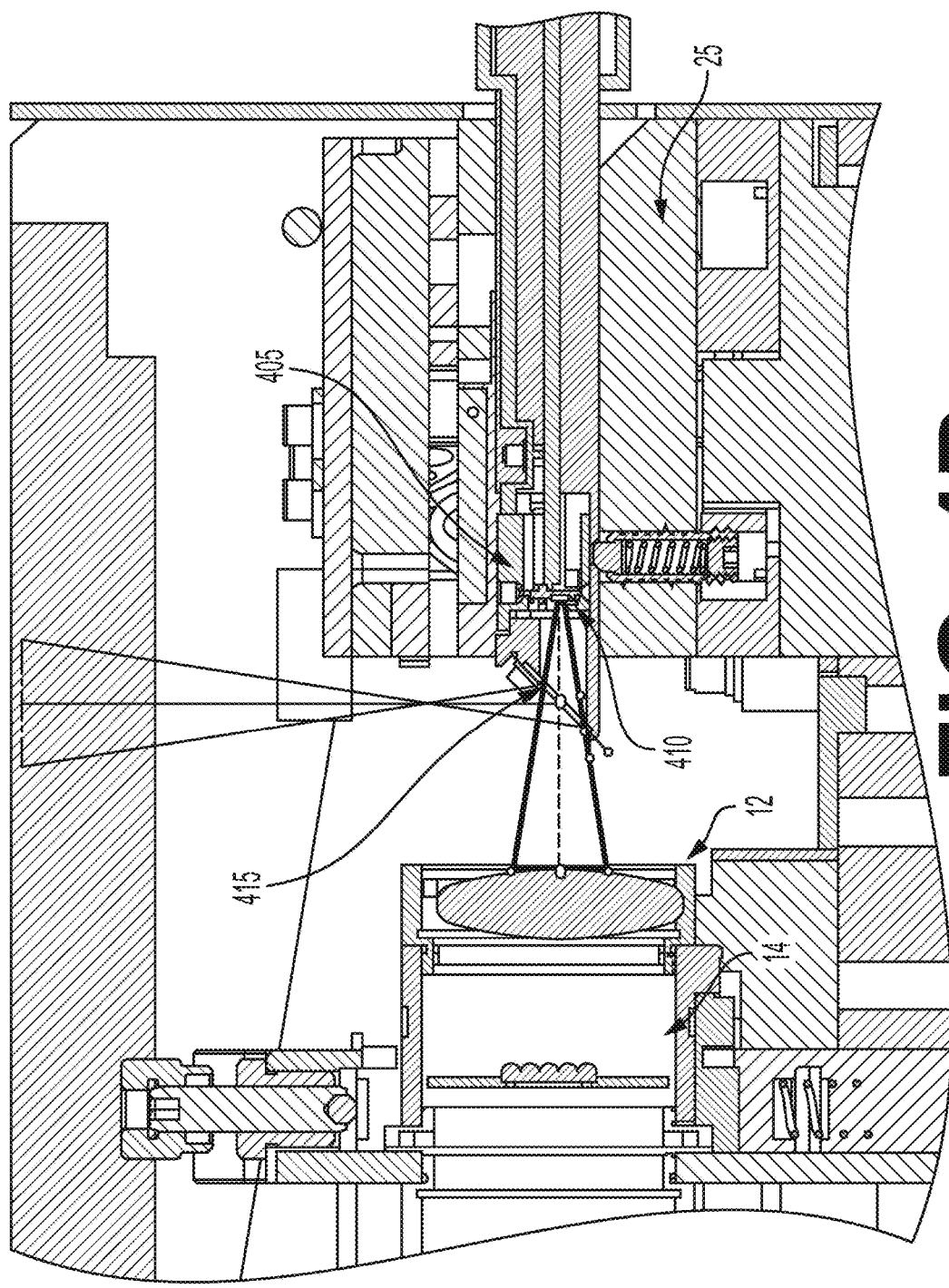
FIG. 4B depicts the insertion portion of the camera housing of FIG. 4A received within a catheter connector of the optical box of the ablation system.

Turning now to FIGS. 4A-4B, a first beam assessment device for testing an ablation system is depicted in accordance with an embodiment. The beam assessment device 400 may be a qualitative beam assessment device configured to assess a shape of a beam emitted by the ablation system. The beam assessment device 400 (which may be referred to as a 'camera jig' herein) comprises a housing such as a camera housing (hereinafter 'camera housing 405'), a visual recording device such as a camera (hereinafter 'camera 410'), and an attenuator 415. In some embodiments, the beam assessment device 400 comprises additional electronic and/or mechanical components for operating the camera 410 and/or recording a signal detected by the camera 410. As further described herein, the beam assessment device 400 may be configured to interface with an optical box 20 of an ablation system at the connector housing 25, i.e., the connection point where a catheter 13 is typically applied to the optical box 20 for delivering the laser energy to the target site (see FIG. 2).

The camera housing 405 is sized and configured to be received by a catheter connector 25 of an ablation system as further described herein. For example, FIG. 4B depicts the insertion portion of the camera housing 405 received within a catheter connector 25 of the optical box 20. As shown, the catheter connector 25 may be an opening, a channel, or a port of the ablation system (e.g., on the optical box 20) that is sized and configured to receive a catheter for use in an ablation procedure by delivering energy from the optical box to the target site as described herein. Accordingly, the catheter connector 25 may be sized according to a size of a catheter 13 to be used with the ablation system. Likewise, in order to mate with the catheter connector 25, the camera housing 405 may have an insertion portion (e.g., the left end as shown in FIG. 4A) that is sized according to the size of the catheter 13 to be used with the ablation system, thereby being sized and configured to be received by the catheter connector 25. As such, the camera housing 405 may have a width or diameter substantially similar to the width or diameter of the catheter 13. In some embodiments, the camera housing 405 has a width or diameter of about 18 mm. However, the width or diameter of the camera housing 405 may vary. For example, the width or diameter of the camera housing may be about 10 mm, about 15 mm, about 20 mm, about 25 mm, about 30 mm, about 35 mm, about 40 mm, about 45 mm, about 50 mm, greater than about 50 mm, or individual values or ranges therebetween any of these values. It should be understood that ablation catheters may vary in size and configuration, and likewise the camera housing 405 may be sized and configured to match any ablation catheter in order to mate with a catheter connector 25 therefor. Furthermore, it should be understood that the while the insertion end of the camera housing 405 is sized and configured as described, additional portions of the beam assessment device 400 and/or the camera housing 405 may have a different size, shape and/or configuration (e.g., as shown in FIG. 4A).

The camera 410 may be disposed on or within the camera housing 405. As shown in FIGS. 4A-4B, the camera 410 may be disposed on or within the insertion portion of the camera housing 405. Furthermore, the camera 410 may be arranged and configured such that, when the camera housing 405 is received by the catheter connector 25, the camera 410 is aligned with a focal plane of a Fourier lens 12 of the optical box 20, i.e., in the same alignment that the optical fiber bundle 13 is typically positioned when received by the catheter connector 25 (see FIG. 2). As shown, at least a portion of the camera 410 may be optically exposed at the insertion portion of the camera housing 405 or otherwise configured to receive a beam from the Fourier lens 12. Exemplary commercially available cameras 410 include the XD Series cameras distributed by Misumi, e.g., model XD-B44106R, model XD-844106R-65, and model XD-B41106RL-65.

In a particular exemplary embodiment, the camera 410 has a diagonal dimension of about 4.8 mm or about 6 mm. However, other diagonal dimensions may also be utilized herein as would be apparent to a person having an ordinary level of skill in the art. Further, the camera 410 may be configured for black and white imaging or color imaging. A sensor of the camera 410 may have a size of at least about 1.5 mm×1.5 mm and a pixel size of less than about 6 μm. In embodiments herein, the sensor size may be greater than or equal to the size of the beam to be measured. For example, where the beam has a diameter of about 1 mm, the sensor should be at least about 1 mm×1 mm and may even be up to about 5 mm×5 mm.

The attenuator 415 may be disposed on or within the camera housing 405 and may be arranged and configured to reduce the intensity of energy reaching the camera 410 from the Fourier lens 12 of the optical box 20. For example, the attenuator 415 may be arranged between the camera 410 and the Fourier lens 12 when the camera housing 405 is received by the catheter connector 25. Accordingly, the energy from the Fourier lens 12 may be reduced by the attenuator 415 before passing to the camera 410 in order to prevent damage to the camera 410. In some embodiments, the attenuator 415 comprises a filter. In some embodiments, the attenuator 415 comprises a deflector, e.g., a beam splitter. In some embodiments, the attenuator 415 comprises a mirror with a coating configured to reduce the energy of the beam. For example, the mirror may be coated on a single side or on both sides to further attenuate the energy of the beam. However, additional types of attenuators 415 may be utilized herein as would be apparent to a person having an ordinary level of skill in the art.

In additional embodiments, the attenuator 415 may be provided separately from the beam assessment device 400 such that it may inserted between the Fourier lens 12 and the camera 410. For example, a plurality of attenuators 415 may be provided, and an attenuator 415 may be selected therefrom for use in order to provide the desired level of attenuation, i.e., to sufficiently reduce the energy to a level that will not damage the camera 410 while still being sufficient for evaluation of the beam profile. In such embodiments, each attenuator 415 of the plurality of attenuators 415 may be configured to provide a different level of attenuation.

In additional embodiments, the attenuator 415 may be omitted from the beam assessment device 400 entirely. For example, the camera 410 may be configured to withstand the energy emitted from the Fourier lens 12 and/or the ablation system may be configured to adjust the energy emitted from the optical box to an appropriate level that will not damage the camera 410 while still being sufficient for evaluation of the beam profile.

In some embodiments, the beam assessment device 400 further comprises an RFID chip (not shown). Typically, ablation catheters include an RFID chip at a location such that, upon connection of the catheter 13 to the catheter connector 25, the ablation system is able to read the RFID chip to obtain information about the catheter 13. Based on the specifications of the catheter 13, the ablation system adjusts the oscillator/amplifier settings to control the laser output. In a similar manner, the RFID chip on the beam assessment device 400 may be arranged such that, upon connection of the beam assessment device 400 to the catheter connector 25, the ablation system is able to read the RFID chip. The RFID chip may be programmed to instruct the ablation system to reduce the energy of the laser. It is contemplated herein that the RFID chip would be used in conjunction with the attenuator 415 to, in combination, reduce the energy to a level that will not damage the camera 410 while still being sufficient for evaluation of the beam profile. However, it is also contemplated that the RFID chip may be sufficient alone without the use of an attenuator 415 to reduce the energy to an appropriate level.

The beam assessment device 400 may include additional components to facilitate operation of the camera 410 and/or communication with remote devices, e.g., receiving input commands and/or transmitting recorded signals from the camera 410. For example, the beam assessment device 400 may further comprise additional controllers, interfaces, and/or electrical components to enable operation of the camera 410, wired or wireless transmission of data, and the like. In some embodiments, the camera 410 includes an imaging chip or FXD. In some embodiments, the beam assessment device 400 includes a cable and/or connector (e.g., USB connector) for electrical communication with a computing device, e.g., for transmitting recorded images and/or video. In some embodiments, the beam assessment device 400 includes a wireless transmission unit for wireless communicating with a computing device, e.g., for transmitting recorded images and/or video.

Figure 5A:
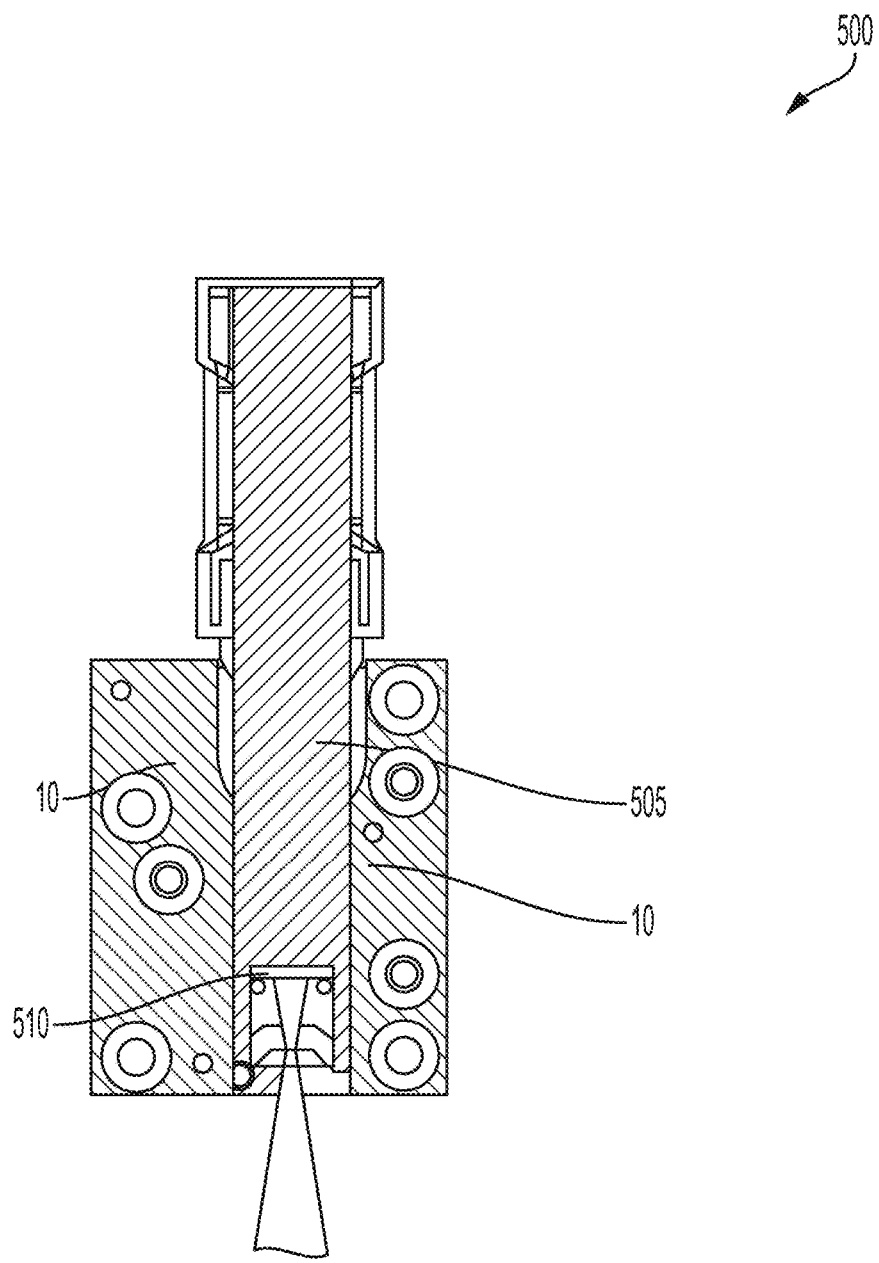
FIG. 5A depicts a second beam assessment device for testing an ablation system in accordance with an embodiment.

Turning now to FIG. 5A, a second beam assessment device for testing an ablation system is depicted in accordance with an embodiment. While the beam assessment device 400 provides qualitative assessment of the beam shape and/or profile, the beam assessment device 500 of FIG. 5A may be a quantitative beam assessment device configured to assess the quantity of energy emitted by the ablation system. The beam assessment device 500 (which may be referred to as a 'sensor jig' herein) comprises a sensor housing 505, a thermoelectric cooler (TEC) 510, and a shutter 515. In some embodiments, the shutter 515 may be replaced by a waveguide 515 or a square core fiber 515 as further described herein. In some embodiments, the beam assessment device 500 comprises additional electronic and/or mechanical components for operating the TEC 510 and/or recording a signal detected by the TEC 510. As further described herein, the beam assessment device 500 may be configured to be received within a catheter connector 25 of the ablation system.

The sensor housing 505 is sized and configured to be received by a catheter connector 25 of an ablation system as further described herein. In order to mate with the catheter connector 25, the sensor housing 505 may have an insertion portion (e.g., the lower end as shown in FIG. 5A) that is sized according to the size of the catheter 13 to be used with the ablation system, thereby being sized and configured to be received by the catheter connector 25. For example, FIG. depicts the insertion portion of the sensor housing 505 received within a catheter connector 25 of the optical box 20. Furthermore, it should be understood that the beam assessment device 400 may be received within the catheter connector 25 in a substantially similar manner as the beam assessment device 500.

The sensor housing 505 may have a width or diameter substantially similar to the diameter of the catheter 13 for use with the ablation system to deliver energy from the optical box to the target site as described herein. In some embodiments, the sensor housing 505 has a diameter of about 18 mm. However, the sensor housing 505 may have various other diameters, such as, for example and without limitation, about 10 mm, about 15 mm, about 20 mm, about 25 mm, about mm, about 35 mm, about 40 mm, about 45 mm, about 50 mm, greater than about 50 mm, or individual values or ranges therebetween any of these values. It should be understood that ablation catheters may vary in size and configuration and that the sensor housing 505 may be sized and configured to match any ablation catheter in order to mate with a catheter connector 25 therefor. Furthermore, it should be understood that while the insertion end of the sensor housing 505 is sized and configured as described, additional portions of the beam assessment device 500 and/or the sensor housing 505 may have a different size, shape and/or configuration (e.g., as shown in FIG. 1t should be understood that the sensor housing 505 is substantially similar to the camera housing 405 of the first beam assessment device 400 and may comprise any of the features and/or functions as described with respect to the camera housing 405.

The TEC 510 may be disposed on or within the sensor housing 505. As shown in FIG. 5A, the TEC 510 may be disposed on or within the insertion portion of the sensor housing 505. Furthermore, the TEC 510 may be arranged and configured to receive energy from the Fourier lens 12 when the sensor housing 505 is received by the catheter connector 25. In some embodiments, the TEC 510 may be replaced with another equivalent type of sensor as would be known and understood to a person having an ordinary level of skill in the art. In additional embodiments where a waveguide 515 or square core fiber 515 is utilized in place of the shutter 515 as described herein, the TEC 510 may be disposed on a backside of the sensor housing 505, i.e., away from the insertion portion of the sensor housing 505. Accordingly, a larger TEC 510 may be utilized in the quantitative beam assessment device 500 and may not be limited by the size of the catheter connector 25 and/or insertion portion of the sensor housing 505.

The shutter 515 may be disposed on or within the sensor housing 505 and may be arranged and configured to deliver energy from the Fourier lens 12 of the optical box 20 to the TEC 510. For example, the shutter 515 may be arranged between the TEC 510 and the Fourier lens 12 when the sensor housing 505 is received by the catheter connector 25. Furthermore, the shutter 515 may be arranged and configured such that, when the sensor housing 505 is received by the catheter connector 25, the shutter 515 is aligned within a focal plane of a Fourier lens 12 of the optical box 20, i.e., in the same alignment that the optical fiber bundle 13 is typically positioned when received by the catheter connector 25 (see FIG. 2). Accordingly, the energy from the Fourier lens 12 may be received by the shutter 515 and directed by the shutter 515 to the TEC 510. The shutter 515 may have an aperture size substantially the same as the size of the beam at the focal plane. Accordingly, misalignment of the beam would result in some energy being blocked by the shutter 515 (i.e., not passing through the aperture) such that the detected energy will be lower than specified to enable a determination of misalignment. Conversely, if the aperture size were larger than the beam, it may be possible that all energy continues to pass through the aperture and misalignment may not be readily detected.

In some embodiments, the shutter 515 may be replaced by a waveguide 515 or a square core fiber 515. For example, a square core fiber such as the Optran WF fiber produced by CeramOptec GmbH of Bonn, Germany may be utilized herein. The technical specifications of the Optran WF fiber are incorporated herein by reference in their entirety. In a specific example, the Optran WF fiber (1000×1000/1600/1750/200 SN) is utilized with a pure fused silica core (1000×1000 µm±2%), a doped silica cladding (1600 µm±2%), a first jacket with a diameter of 1750 µm±5%, a second jacket with a diameter of 2000 µm±5%, and an aperture of 0.22 µm±0.02. However, it should be understood that various fiber specifications may be utilized herein as would be known to a person having an ordinary level of skill in the art. Similar to the shutter 515, the waveguide or square core fiber 515 may be arranged and configured to deliver energy from the Fourier lens 12 of the ablation system to the TEC 510. For example, the waveguide or square core fiber 515 may be arranged between the TEC 510 and the Fourier lens 12 when the sensor housing 505 is received by the catheter connector 25. Furthermore, the waveguide or square core fiber 515 may be arranged and configured to be aligned within a focal plane of the Fourier lens 12 when the sensor housing 505 is received by the catheter connector 25. Accordingly, the energy from the Fourier lens 12 may be received by the waveguide or square core fiber 515 and directed by the waveguide or square core fiber 515 to the TEC 510. It should be understood that additional types of components may be utilized herein to direct energy from the Fourier lens 12 to the TEC 510 as would be apparent to a person having an ordinary level of skill in the art.

The quantitative beam assessment device 500 may include additional components to facilitate operation of the TEC 510 and/or communication with remote devices, e.g., receiving input commands and/or transmitting recorded signals from the TEC 510. For example, the beam assessment device 500 may further comprise additional controllers, interfaces, and/or electrical components to enable operation of the TEC 510, wired or wireless transmission of data, and the like. In some embodiments, the quantitative beam assessment device 500 includes a cable and/or connector (e.g., USB connector) for electrical communication with a computing device, e.g., for transmitting recorded signals. In some embodiments, the quantitative beam assessment device 500 includes a wireless transmission unit for wireless communication with a computing device, e.g., for transmitting recorded signals.

Figure 5B:
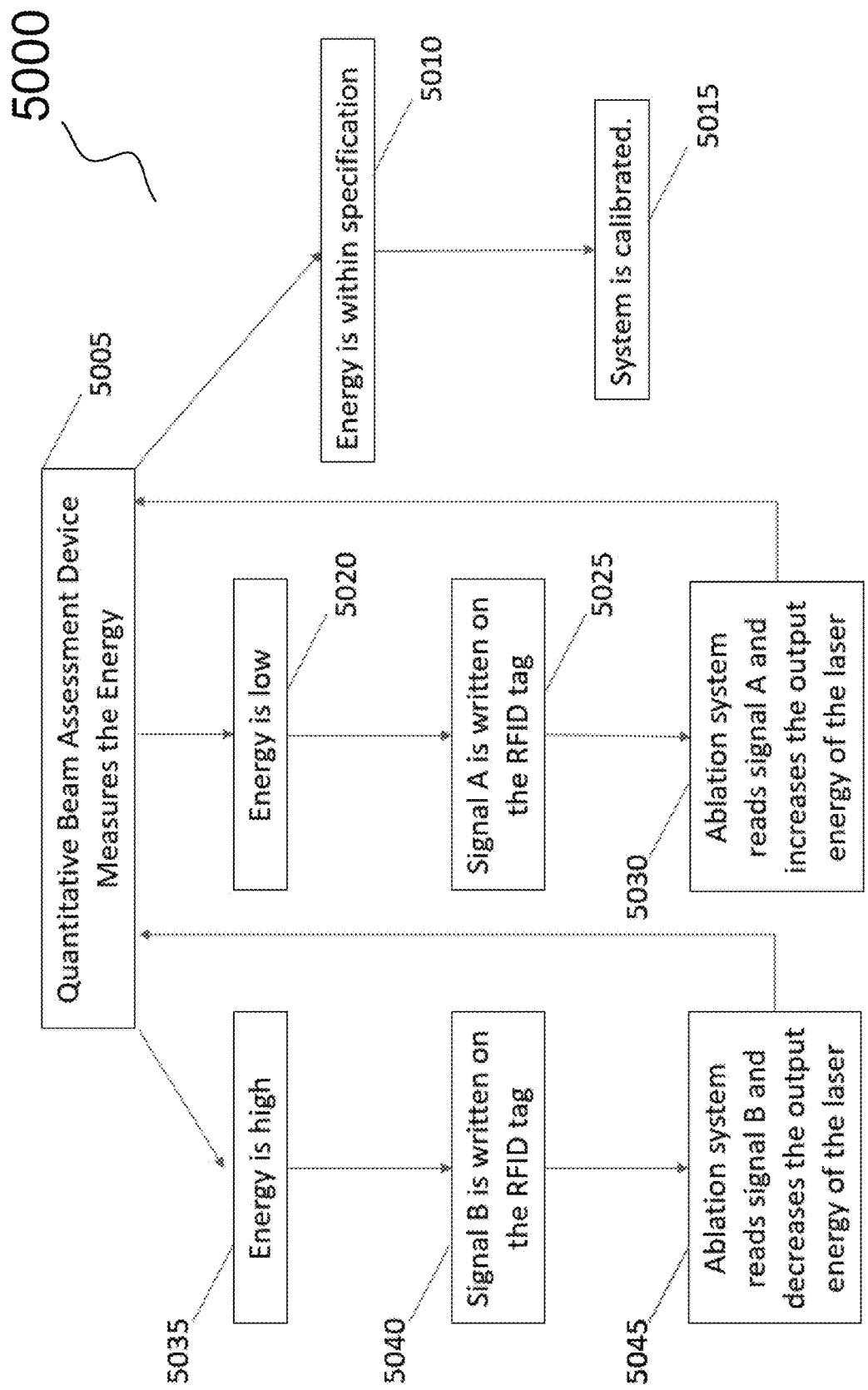
FIG. 5B depicts an exemplary flow diagram of a method of calibrating an ablation system using a quantitative beam assessment device in accordance with an embodiment.

In some embodiments, the quantitative beam assessment device 500 further comprises an RFID tag for calibrating the ablation system. Advantageously, the quantitative beam assessment device 500 may be used to calibrate the ablation system without the need to open the ablation system for connecting thereto. In order to calibrate the ablation system, the energy output of the ablation system is measured by the quantitative beam assessment device 500 as described herein and a signal is written to the RFID tag to indicate the energy level (e.g., a quantitative indication of energy and/or a relative indication with respect to the specification). FIG. 5B depicts an exemplary flow diagram of a method of calibrating an ablation system using the quantitative beam assessment device 500 in accordance with an embodiment. As shown, the method 5000 comprises measuring 5005 the energy level of the ablation system using the quantitative beam assessment device 500. When the detected energy level is within specification 5010, the calibration process is completed 5015. When the detected energy is below specification 5020 (i.e., too low), a control unit of the quantitative beam assessment device 510 and/or an external control unit communicating therewith (e.g., control unit 620 as further described herein) writes 5025 a first signal (e.g., signal A) on the RFID tag. Upon reading of the first signal by the ablation system (e.g., the laser), the ablation system increases 5030 the energy level output by the laser. The process then returns to step 5005. When the detected energy level is above specification 5035 (i.e., too high), the control unit of the quantitative beam assessment device 510 and/or an external control unit communicating therewith writes 5040 a second signal (i.e., signal B) on the RFID tag. Upon reading of the second signal by the ablation system (e.g., the laser), the ablation system decreases 5045 the energy level output by the laser. The process then returns to step 5005. This process may continue until the desired energy is achieved and the energy is determined to be within specification 5010 such that the calibration process is completed 5015. Additional details related to calibration that may be implemented as part of the method 5000 are disclosed in U.S. patent application Ser. No. 17/469,839 entitled "Dynamic Laser Stabilization and Calibration System," filed on Sep. 8, 2021, which is incorporated herein by reference in its entirety.

In some embodiments, the first and second signals may be qualitative (i.e., indicating too low or too high) and the ablation system may increase or decrease the energy level by a set amount upon reading the first or second signal, respectively, such that multiple iterations may be required to increase or decrease the energy level to within specification. In some embodiments, the first and second signals may be quantitative (i.e., indicating a quantitative measurement of the energy) and the ablation system may increase or decrease the energy level based on the indicated energy level to bring the energy level closer to specification.

The devices, systems, and methods described herein are not intended to be limited in terms of the particular embodiments described, which are intended only as illustrations of various features. Many modifications and variations to the devices, systems, and methods can be made without departing from their spirit and scope, as will be apparent to those skilled in the art.

While the instant invention is described relative to a laser ablation system, it is to be understood that embodiments disclosed herein may be equally configured for use with other types of systems having different optical and/or ablation sources with mirror modifications as would be apparent to a person having an ordinary level of skill in the art.

System for Testing an Optical Box

Figure 6:
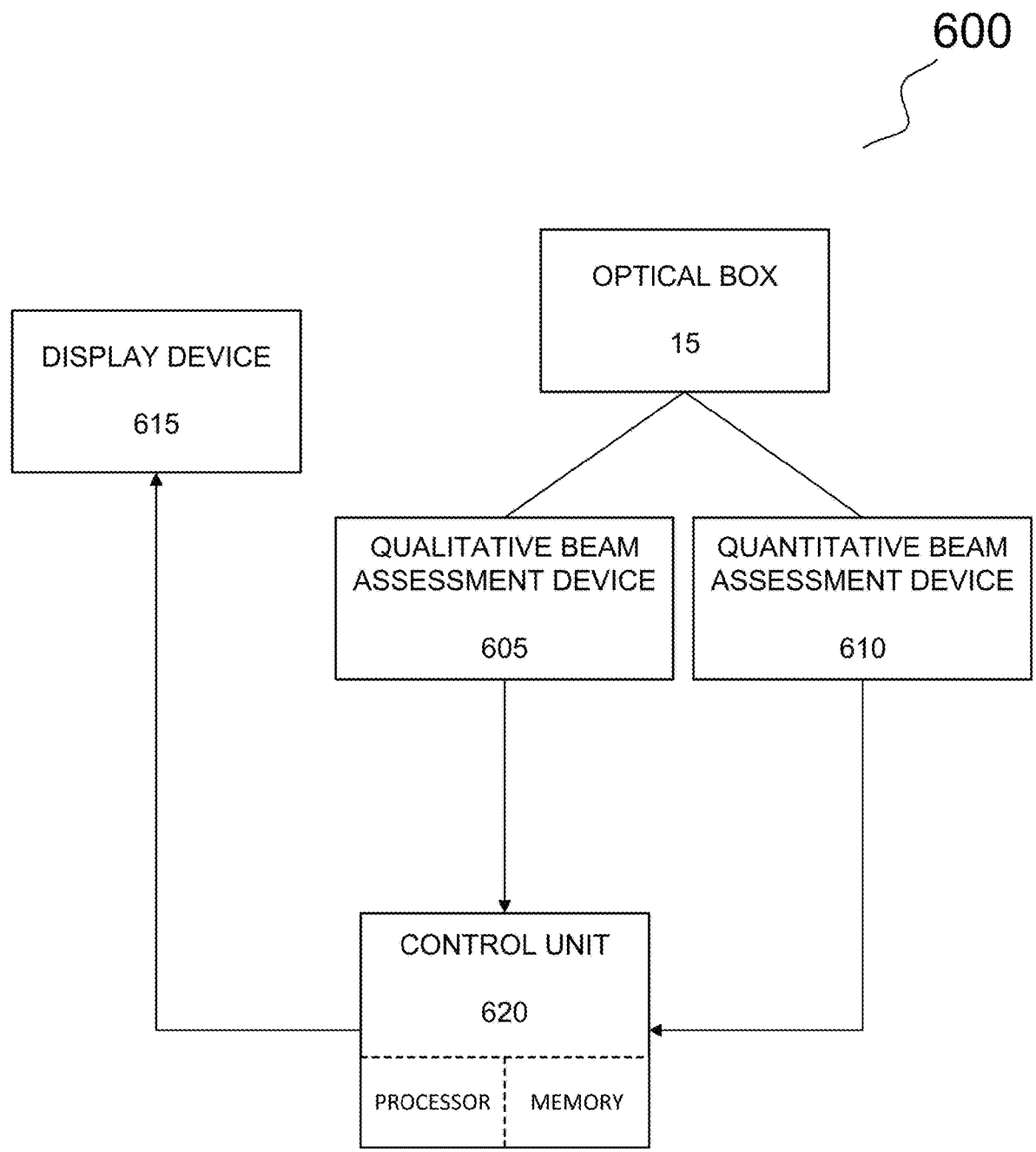
FIG. 6 depicts a block diagram of a system for testing an optical box of an ablation system in accordance with an embodiment.

Turning now to FIG. 6, a block diagram of a system for testing an optical box of an ablation system is depicted in accordance with an embodiment. The system 600 comprises a qualitative beam assessment device 605, a quantitative beam assessment device 610, a display device 615, and a control unit 620 comprising a processor and a memory. The qualitative beam assessment device 605, the quantitative beam assessment device 610, and the display device 615 are each in electrical communication with the control unit 620. As further described herein, the system 600 may be configured to interface with an optical box 20 of an ablation system by the qualitative beam assessment device 605 and/or the quantitative beam assessment device 610 being received by the catheter connector 25 of the optical box 20 at different times.

The qualitative beam assessment device 605 may be configured to assess a shape or profile of a beam emitted by the optical box 20. The qualitative beam assessment device 605 (which may be referred to as a 'camera jig' herein) comprises a camera housing, a camera, and optionally an attenuator. In some embodiments, the qualitative beam assessment device 605 comprises additional electronic and/or mechanical components for operating the camera and/or recording a signal detected by the camera. The camera housing of the qualitative beam assessment device 605 is sized and configured to be received by the catheter connector 25 of the optical box 20. It should be understood that the qualitative beam assessment device 605 may be the first beam assessment device 400 as described herein with respect to FIGS. 4A-4B and may comprise any of the components, features and/or functions as described with respect to the first beam assessment device 400.

The quantitative beam assessment device 610 may be configured to assess the quantity of energy emitted by the optical box 20. The quantitative beam assessment device 610 (which may be referred to as a 'sensor jig' herein) comprises a sensor housing, a thermoelectric cooler (TEC), and a shutter. In some embodiments, the shutter may be replaced by a waveguide or a square core fiber. In some embodiments, the quantitative beam assessment device 610 comprises additional electronic and/or mechanical components for operating the TEC and/or recording a signal detected by the TEC. As further described herein, the sensor housing of the quantitative beam assessment device 610 may be configured to be received by the catheter connector 25 of the optical box 20 in substantially the same manner and/or location as the qualitative beam assessment device 605. For example, the qualitative beam assessment device 605 may be received by the catheter connector 25 and subsequently removed and replaced by the quantitative beam assessment device 610 during testing. In another example, the quantitative beam assessment device 610 may be received by the catheter connector 25 and subsequently removed and replaced by the qualitative beam assessment device 605 during testing. It should be understood that the quantitative beam assessment device 610 may be the second beam assessment device 500 as described herein with respect to FIG. 5A and may comprise any of the components, features and/or functions as described with respect to the second beam assessment device 500.

The display device 615 may be a visual display configured to render visual information, which may include any graphical or textual information related to testing the optical box 20 as described herein. For example, the display device 615 may present display recorded signals from the qualitative beam assessment device 605 (e.g., captured images) and/or the quantitative beam assessment device 610 (e.g., measured energy). In another example, the display device 615 may present graphical or textual depictions of other information related to different steps of the testing process, e.g., an indication of a particular issue or diagnosis for the optical box. In some embodiments, the display device 615 may present a diagnosis of a failure mode and/or an associated repair for the failure mode. In some embodiments, the display device 615 is a touchscreen or a touch-sensitive display. In some embodiments, the display device 615 is a wireless display remotely located from other components of the system 600. In some embodiments, the display device 615 is a display associated with a computing device of the ablation system, e.g., a device for planning and executing an ablation procedure and/or displaying information related to the ablation procedure. In additional embodiments, the display device 615 may be a display associated with a separate computing device dedicated for testing the optical box 20.

The control unit 620 may be in electrical communication with the qualitative beam assessment device 605, the quantitative beam assessment device 610, the display device 615, and/or additional components of the system 600 in order to enable a user to test the optical box 20 and/or obtain results of the testing. In some embodiments, the control unit 620 includes a processor and a memory such as a non-transitory, computer-readable medium storing instructions for testing the optical box 20. In some embodiments, the control unit 620 may be a computing device associated with the ablation system. Accordingly, testing of the optical box 20 may be performed using the same computing device used to plan and/or execute the ablation procedure. In additional embodiments, the control unit 620 may be a separate computing device dedicated for testing the optical box 20.

In some embodiments, the system 600 further comprises at least one input device. The at least one input device may comprise any number and type of input devices configured to receive and/or process input from a user. For example, the input device may include a mouse, a trackpad, a keyboard, a touchscreen, a microphone, a foot pedal, one or more knobs, one or more sliders, one or more switches, one or more user interaction components, and the like. However, any type of input device as would be known to a person having an ordinary level of skill in the art may be utilized in combination with the systems herein. The input device may be configured to provide input to the control unit 620 to initiate or control testing of the optical box 20, to control or modify the information displayed on the display 615, and/or perform other actions related to operation of the system 600.

Figure 7:
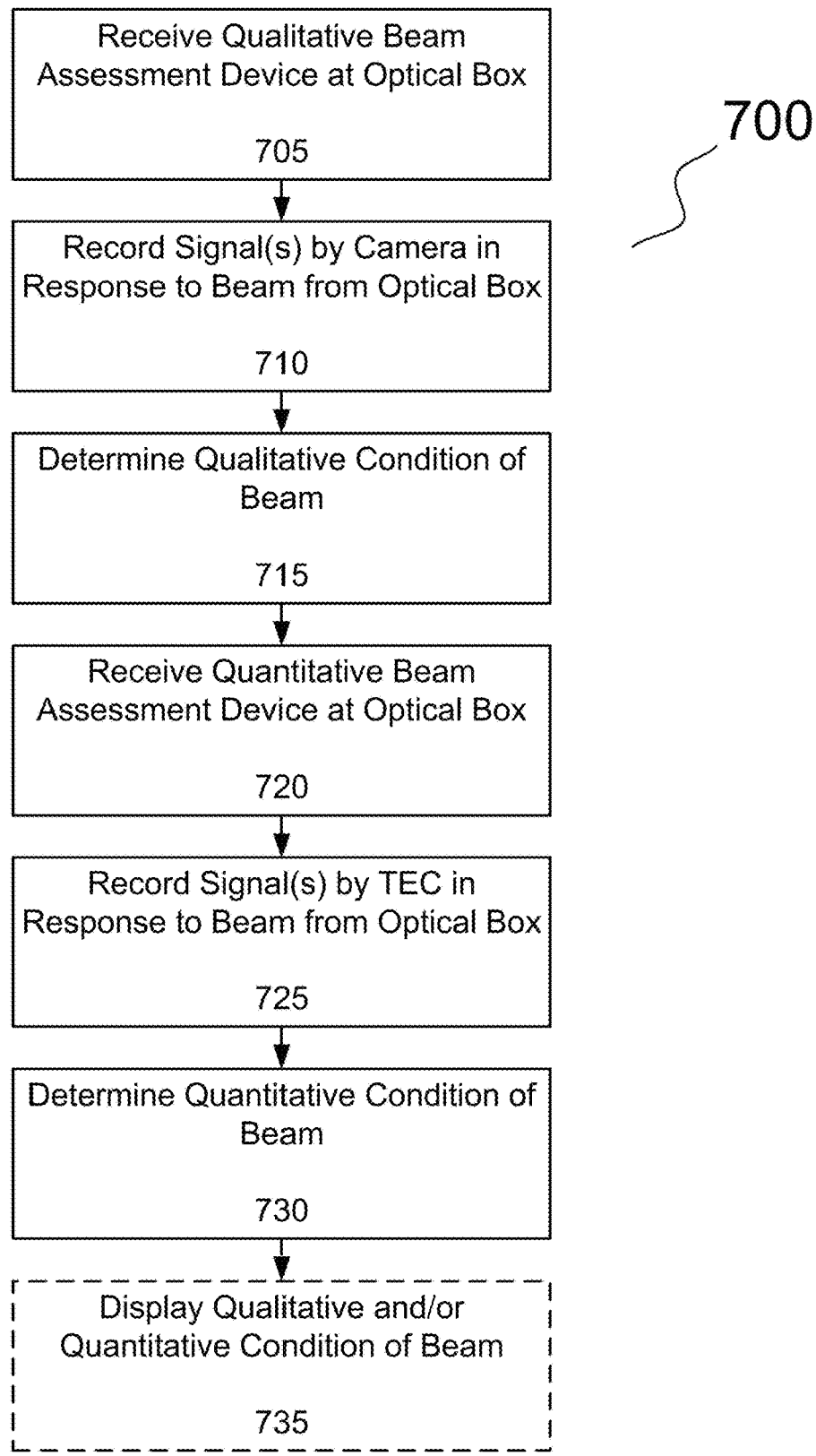
FIG. 7 depicts a flow diagram of an illustrative method for testing an optical box in accordance with an embodiment.

Turning now to FIG. 7, a flow diagram of an illustrative method 700 for testing an optical box 20 by the system 600 is depicted in accordance with an embodiment. For example, the method 700 may be partially carried out by the processor of the control unit 620 upon execution of the instructions stored on the memory. The method 700 comprises receiving 705 the qualitative beam assessment device 605 at the catheter connector 25, recording 710 one or more signals related to a beam profile by the camera of the beam assessment device 605 in response to a beam from the optical box 20, determining 715 a qualitative condition of the beam profile (i.e., detecting energy drift and/or failure mode associated therewith) based on the one or more recorded signals related to the beam profile, receiving 720 the quantitative beam assessment device 610 at the catheter connector 25, recording 725 one or more signals related to beam energy by the TEC of the beam assessment device 610 in response to a beam from the optical box 20, and determining 730 a quantitative condition of the beam (i.e., detecting energy level) based on the one or more recorded signals related to beam energy. In some embodiments, the method 700 further comprises displaying 735 the determined qualitative condition and/or the determined quantitative condition (e.g., including one or more failure modes associated with the conditions) on the display 615.

In some embodiments, recording 710 one or more signals by the camera of the qualitative beam assessment device 605 comprises capturing a still image. In some embodiments, recording 710 one or more signals by the camera of the qualitative beam assessment device 605 comprises capturing a plurality of still images. In some embodiments, recording 710 one or more signals by the camera of the qualitative beam assessment device 605 comprises capturing a video clip. In some embodiments, recording 710 one or more signals by the camera of the qualitative beam assessment device 605 comprises capturing a plurality of video clips.

In some embodiments, the control unit 620 may determine 715 the qualitative condition of the beam based on the beam profile. For example, the control unit 620 may be configured to process the recorded signals from the camera to determine the qualitative condition of the beam based on the beam profile. In some embodiments, determining 715 a qualitative condition of the beam comprises determining whether the beam of the optical box is properly aligned and ready to use. As such, in some embodiments, the determination 715 comprises an indication that the optical box is ready to use. In some embodiments, the determination 715 comprises an indication of energy drift and/or a specific failure mode causing the energy drift.

In some embodiments, determining 715 a qualitative condition of the beam comprises determining whether the beam of the optical box is properly aligned and ready to use. As such, in some embodiments, the determination 715 comprises an indication of alignment. In some embodiments, the determination 715 comprises an indication of misalignment. Additionally, in cases of misalignment, the control unit 620 may advantageously identify a particular issue causing the misalignment.

Figure 8A:
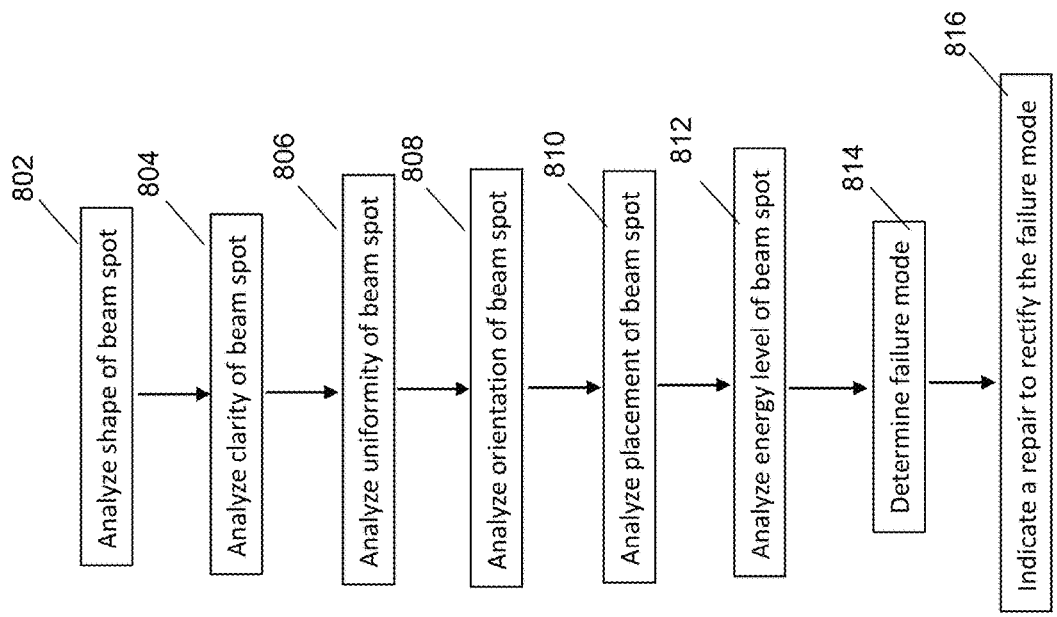
FIG. 8A depicts a flow diagram of an illustrative method for determining a failure mode and identifying a repair to rectify the failure mode.

As shown in FIG. 8A, the control unit 620 can analyze the shape of the beam spot 802. In one example, the control unit 620 can analyze whether the beam is rectangular in shape or non-rectangular in shape such as, for example, circular in shape. However, the beam spot can be any shape without departing from aspects of the disclosure discussed herein. The beam spot shape can be dependent on the type and/or arrangement of fiber optics used. In addition, the control unit 620 can analyze the clarity of the beam spot 804 such as whether the beam spot is clear or unclear or whether the beam spot is very dim or does not appear at all. The control unit 620 can also analyze the uniformity of the beam spot 806 such as whether one side of the beam spot being brighter than another and/or whether a portion of the beam spot is spreading in one direction such that the beam spot is sharper or brighter in one direction relative to another. Further, the control unit 620 can analyze the orientation of the beam spot 808 such as whether the beam spot is oriented in the center of the screen of the display 615 or shifted off-center. The control unit 620 can also analyze the placement of the beam spot 810 such as the angle of the beam spot on the screen. Even further, the control unit 620 can analyze an energy level of the beam spot 812. The analysis of the energy level can also be used to verify orientation of the beam spot exiting the system and whether the beam overlaps the fibers.

As disclosed elsewhere herein, analysis of the shape, clarity, uniformity, orientation, placement and energy level of the beam spot may include analysis of the signals captured by the qualitative beam assessment device, the quantitative beam assessment device or both.

Additionally, the control unit 620 can determine a failure mode of the system based on the analysis of the beam spot 814. For example, the control unit 620 can determine a failure mode based on at least one of the shape, clarity, uniformity, orientation, placement and energy level of the beam spot. Examples of failures modes include: misalignment of the beam; blocking of an S-beam of the beam from entering an optical element of the optical box; misalignment of a mirror of the optical box; shifting of the S-beam; misalignment of the beam in the Z-direction from a focal point of the optical box; damage to the MLA; failure of a laser of the ablation system; failure of a sensor of the ablation system; cutting of the beam; misalignment of a P-beam and an S-beam of the beam; a dirty optical element of the optical box; misalignment of the catheter connector in the X-Y plane; misalignment of the catheter connector in the Z-direction; low overall energy; and/or improper energy distribution.

Once the failure mode has been determined, the control unit 620 can indicate a repair for rectifying the failure mode 816 including whether to open the optical box 20 and which, if any, of the optical components therein should be aligned, cleaned, replaced, fixed and/or modified. Examples of repairs include: alignment of the S beam; unblocking of the S-beam to enter optical element of the optical box; alignment of the mirror; alignment of the beam to the focal point of the optical box; repairing the damage or replacing the MLA; correcting the failure of or replacing the laser of the ablation system; correcting the failure of or replacing the sensor of the ablation system; aligning the P-beam and S-beam; cleaning an optical element of the optical box (e.g., cleaning a lens such as the coupling lens or Fourier lens 12); replacing an optical element of the optical box; repairing an optical element of the optical box; aligning the catheter connector in the X-Y plane; aligning the catheter connector in the Z-direction; increasing the overall energy; aligning the S-beam and/or unblocking the S-beam to enable entry to the optical element of the optical box, aligning the mirror, and/or correcting the energy distribution. The specific type of failure mode may dictate whether the optical box 20 must be opened to complete the repair. For example, in the case of a dirty or occluded optical element, the repair may or may not require opening of the optical box 20 depending on which optical element is dirty or occluded. In the case of the coupling lens or Fourier lens 12 or another terminal lens of the assembly, cleaning may be performed by inserting a cleaning tool through the catheter connector 25 and cleaning the lens without the need to open the optical box. However, in the case of optical elements deeper within the assembly, cleaning may require opening of the optical box 20. The specific type of failure mode may also dictate where the repair can be made, i.e., whether the repair can be performed in the field (e.g., at a hospital or office-based lab) or whether the ablation system and/or optical box must be sent to a manufacturing or repair facility.

Figure 8B:
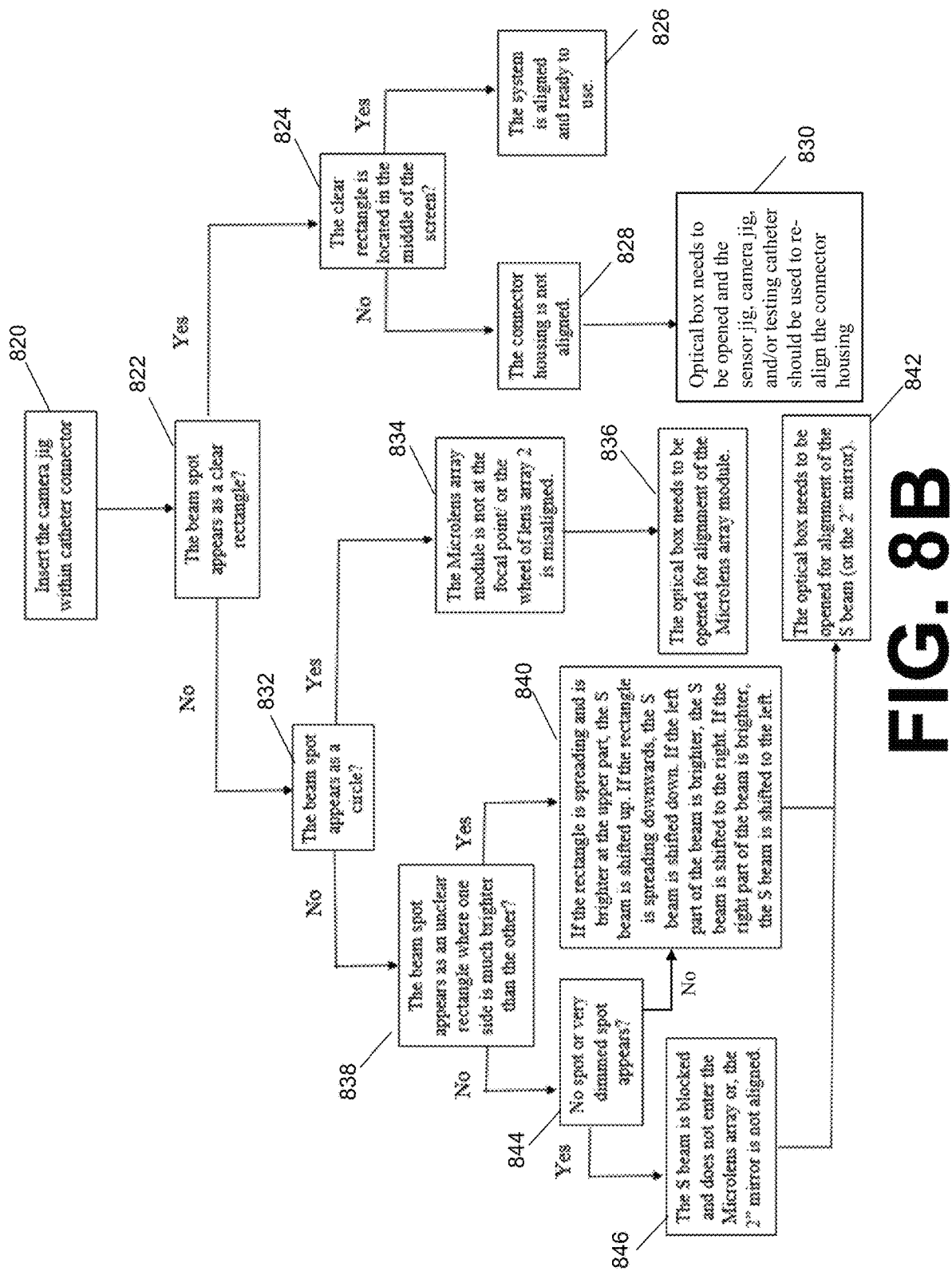
FIG. 8B depicts an exemplary logic diagram for assessing images or videos from the camera to determine the qualitative condition of the beam and/or a cause of misalignment.

In one example as shown in FIG. 8B, the camera jig can be inserted within the catheter connector at 820 and the control unit 620 can analyze the beam spot shape and clarity such as, for example, whether the beam spot appears as a clear rectangle at 822. If the beam spot appears as a clear rectangle, the control unit 620 can next analyze whether the clear rectangle is located in the middle of the screen at 824. If yes, the control unit 620 can indicate that the system is aligned and ready to be used at 826. If not, the control unit 620 can determine that the connector housing is not aligned at 828. As a result, the control unit 620 can indicate a repair including opening the optical box and using the sensor jig, camera jig or testing catheter to align the connector housing 830.

If the control unit 620 determines that the beam spot is not a clear rectangle at 822, the control unit 620 can analyze whether the beam spot appears as a circle at 832. If it is determined that the beam spot appears as a circle, the control unit 620 can further determine the microlens array module is not the focal point or the wheel of the second lens array is misaligned at 834. As a result, the control unit 620 can indicate a repair including that the optical box should be opened for alignment of the microlens array module at 836.

Returning to 832, if the control unit 620 determines that the beam spot does not appear as a circle, the control unit 620 can analyze whether the beam spot spears as an unclear rectangle where one side is much brighter than another at 838. If yes, the control unit 620 can continue with analysis at 840. For example, if the rectangle is spreading and is brighter at the upper part, the control unit 620 can determine that the S beam is shifted up; if the rectangle is spreading downwards, the control unit 620 can determine that the S beam is shifted down; if the left part of the beam is brighter, the control unit 620 can determine that the beam is sifted to the right; if the right part of the beam is brighter, the control unit 620 can determine that the S beam is shifted to the left.

At 842, the control unit 620 can indicate a repair including that the optical box should be opened for alignment of the S beam.

Returning to 838, if the control unit 620 determines that the beam spot does not appear as an unclear rectangle where one side is much brighter than the other, the control unit 620 can further analyze whether there is no spot or a very dim spot at 844. If the control unit 620 determines that the beam spot is unclear where one side is brighter, than the control unit 620 can further determine that the S beam is blocked and does not enter the microlens array, or the final mirror of the optical box 20 (e.g., a 2 inch mirror before coupling lens 12 and after the second polarization beam splitter 29 as shown in FIG. 2) is not aligned at 848. As a result, the control unit 620 can indicate that the optical box should be opened for alignment of the final mirror.

FIG. 8B depicts an exemplary logic diagram for assessing images or videos from the camera to determine the qualitative condition of the beam and/or a cause of misalignment. As shown, the causes of misalignment may include: blocking of the S-beam from entering the microlens array (MLA) 14 (see FIGS. 1 and 4B); misalignment of the final mirror of the optical box (i.e., a final mirror before coupling lens 12 and after the second polarization beam splitter 29 in FIG. 2); shifting of the S-beam upwards/downwards/left/right (see FIG. 3A); misalignment of the MLA from the focal point (see FIGS. 1-2 and 4B); misalignment of the wheel of a lens array; and misalignment of the connector housing 25 (see FIG. 2).

As also shown in FIG. 8B, the control unit 620 may additionally indicate a repair for rectifying the misalignment. In some embodiments, the repair may be indicated on the display 615 to a user. Advantageously, indication of the cause of misalignment and/or the repair may alleviate the need to open the optical box 20 unless a particular issue therein has been identified for repair. Accordingly, the components of the optical box 20 and the arrangement thereof are not placed at risk by opening the optical box 20 unless it is necessary.

In some embodiments, determining 715 a qualitative condition of the beam comprises detecting additional failure modes. Additional types of issues may be identified including but not limited to MLAM damage, laser issues, internal sensor issues, beam cut on an aperture of an optical element, beam cut along the optical path, misalignment of the P- and S-beams, dirty bi-convex or other dirty optical elements, connector housing movement in the X-Y plane, connector housing movement in the Z-direction, low overall energy, improper energy distribution, and the like. It should be understood that any of the various issues with the qualitative condition of the beam as described herein may be identified using image processing algorithms.

In some embodiments, image processing algorithms are employed to determine 715 the qualitative condition of the beam based on the beam profile. Notably, the image processing algorithms may be configured to detect particular issues or causes for poor condition of the beam. In some embodiments, images of the beam profile collected by the camera of the beam assessment device 605 may be digitally processed and/or manipulated in order to identify misalignment and/or causes of misalignment as described with respect to FIG. 8. In some embodiments, images of the beam profile collected by the camera of the qualitative beam assessment device 605 may be digitally processed and/or manipulated in order to identify whether the MLAM is damaged. In some embodiments, images of the beam profile collected by the camera of the qualitative beam assessment device 605 may be digitally processed and/or manipulated in order to identify whether an optical element is dirty, spotted, and/or otherwise occluded. For example, a dirty or otherwise occluded optical element (e.g., a lens) may cause the collected images to contain dimmed or dark spots due to the beam being blocked in particular regions by dirt, dust, stains, debris, and/or other occluding material on the optical element. Accordingly, the collected images may be processed by image processing techniques as would be known to a person having an ordinary level of skill in the art to identify dimmed or dark spots based on the intensity of the beam at various portions of images and determine whether an optical element is dirty or occluded. In some instances, dirty or occluded optical elements may present features in the collected images that are uniquely identifiable from other types of issues, e.g., misalignments and/or other blocking of the beam, that may be identified by image processing. In some instances, the features in the collected images may also be indicative of the particular optical element that is dirty or occluded (e.g., a final lens of the assembly such as the coupling lens or Fourier lens 12, i.e., a bi-convex lens), which may provide information about the manner of repair. For example, in the case of a dirty or occluded optical element, the repair may or may not require opening of the optical box 20 depending on which optical element is dirty or occluded. In the case of the coupling lens or Fourier lens 12 or another terminal lens of the assembly, cleaning may be performed by inserting a cleaning tool through the catheter connector 25 and cleaning the lens without the need to open the optical box. However, in the case of optical elements deeper within the assembly, cleaning may require opening of the optical box 20. It should be understood that any of the various issues with the qualitative condition of the beam as described herein may be identified using image processing algorithms.

In some embodiments, a machine learning algorithm may be utilized to determine 715 the qualitative condition of the beam and/or causes thereof. In some embodiments, the machine learning algorithm may further determine and/or indicate a solution to improve the qualitative condition of the beam, e.g., by repairing the determined cause. For example, the machine learning algorithm may indicate that a component of the system 600 should be adjusted or moved in a particular direction for a particular distance, a particular angle, or the like. For example, a machine learning algorithm may be trained using a set of training data. In some embodiments, the set of training data comprises images of beams with various conditions and including various types and degrees of misalignment. The training data may be used to train the machine learning algorithm to identify proper alignment, identify misalignment, and identify a cause of misalignment based on an image or video of the beam. Accordingly, the machine learning algorithm may become more proficient in identifying the cause of misalignment over time. Thus, a trained machine learning algorithm may identify the qualitative condition and/or the cause thereof, thereby allowing the control unit 620 to determine 715 the qualitative condition based on the recorded signals from the camera without human input. It should be understood that any of the various issues with the qualitative condition of the beam as described herein may be identified using trained machine learning algorithms.

In some embodiments, the control unit 620 utilizes a plurality of machine learning algorithms for identifying the qualitative condition and/or the cause of misalignment. For example, the control unit 620 may utilize a machine learning algorithm to determine whether the beam is properly aligned. Upon determining misalignment, the control unit 620 may utilize a separate machine learning algorithm for each known cause of misalignment to assess whether the cause is present in the instant case. Accordingly, as machine learning algorithms are improved and/or as additional types of issues associated with the qualitative condition of the beam are identified or further understood, the control unit 620 may be updated to improve qualitative assessment of the beam.

In some embodiments, the machine learning algorithm(s) may be re-trained over time and thus improved. For example, a machine learning algorithm may be trained using a first set of training data, which may be "seed data." The seed data may be of at least a critical volume to enable the machine learning algorithm to satisfactorily determine 715 the qualitative condition of the beam in live cases. Following the performance of the method 700, the recorded signals from the camera and the outcome data associated therewith may be used to further train the machine learning algorithm(s). For example, where a particular type of misalignment is identified and confirmed by a user, the machine learning algorithm may obtain an indication of these outcomes and may be trained over time to provide similar predictions or proposals in similar scenarios, thereby improving identification. Likewise, if a determination by the control unit 620 is rejected by a user, the machine learning algorithm may obtain an indication of these outcomes and may be trained over time to provide different and/or better determinations in similar scenarios, thereby improving identification. Accordingly, live cases may be used to form a second set of training data, which may be "refinement data" that is used on a continual basis to re-train the machine learning algorithms.

In some embodiments, the control unit 620 and/or the machine learning algorithms employed by the system 600 are configured to detect additional issues with the optical box 20, additional types of misalignment of the optical box 20, and/or additional information associated with the optical box 20. For example, the control unit 620 and/or the machine learning algorithms may be configured to predict a degree of misalignment of a component, e.g., a degree or distance by which the S-beam is misaligned.

While various methods of determining 715 the qualitative condition of the beam by the control unit 620 are described herein, it should be understood that the qualitative condition may also be determined 715 with human input. For example, a user may view images and/or videos recorded by the qualitative beam assessment device 605 (e.g., on a display device 615 as described herein) and compare it to sample images of known issues, i.e., a lookup table. Based on the comparison, the user may determine whether the optical box is properly aligned, and if not, the particular failure mode exhibited by the beam. In some embodiments, the lookup table may comprise a series of images taken with the qualitative beam assessment device 605 under different failure modes. The images in the lookup table may be labeled according to the failure mode and may provide details or directions for identifying particular failure modes as well as particular repairs or steps for fixing the identified failure mode. In some embodiments, the user may input the determined 715 qualitative condition to the control unit 620. In additional embodiments, the user may not input the determined 715 qualitative condition to the control unit 620; rather, the user may use the determined information to determine a necessary repair without the assistance of the control unit 620 (e.g., by reference to the lookup table).

In some embodiments, recording 725 one or more signals by the TEC of the quantitative beam assessment device 610 comprises recording an energy measurement. In some embodiments, recording 725 one or more signals by TEC of the quantitative beam assessment device 610 comprises recording a plurality of energy measurements.

In some embodiments, the control unit 620 may determine 730 the quantitative condition of the beam. For example, the control unit 620 may be configured to process the recorded signals from the TEC to determine the energy level of the beam. In some embodiments, determining 730 the quantitative condition of the beam comprises determining whether the energy level of the beam of the optical box 20 is within specification (e.g., within about 10% of a target level) and thus ready to use. As such, in some embodiments, the determination 730 comprises an indication of proper energy levels. For example, for a given clinical use energy level, the beam may be determined to be within specification if the energy level reaching the TEC is within a specified range, which may be reduced from the clinical use setting. In some embodiments, the determination 730 comprises an indication of improper energy levels (i.e., too low or too high) such that the laser setting may require adjustment in order to produce proper energy levels within specification. For example, for a given clinical use energy level, improperly high and/or slightly low energy levels (e.g., about 10-15% below the specification range) reaching the TEC may indicate that the settings of the laser require adjustment. In additional embodiments, the determination 730 comprises an indication of substantially low energy levels such that the optical box may require opening and re-aligning in order to produce proper energy levels within specification. For example, for a given clinical use energy level, substantially low energy levels (e.g., greater than about 10-15% below the specification range) reaching the TEC may indicate that the optical box should be opened and re-aligned. Table 1 summarizes the energy level ranges that are indicative of each determination 730 for a given clinical use energy level as described herein.

TABLE 1

| | | |
|---|---|---|
| Clinical Use Energy Level | 50 mJ/mm$^2$ | 60 mJ/mm$^2$ |
| Detected Energy within Specification | 24.2-26.8 mJ/mm$^2$ | 26.1-28.9 mJ/mm$^2$ |
| Detected Energy Requiring Adjustment of Laser Setting | 21-24.2 mJ/mm$^2$ or >26.8 mJ/mm$^2$ | 23-26.1 mJ/mm$^2$ or >28.9 mJ/mm$^2$ |
| Detected Energy Requiring Opening and Aligning Optical Box | <21 mJ/mm$^2$ | <23 mJ/mm$^2$ |

It should be understood that the energy level is measured by the quantitative beam assessment device 610 at the same location that the optical fibers of a catheter would interface with the ablation system (i.e., at the catheter connector 25). Accordingly, a determination that the energy level is sufficient confirms (1) sufficient energy transmission from the beam, and also (2) that the beam is sufficiently aligned with the aperture and/or optical fibers. As such, while the qualitative beam assessment device 605 may be used to detect failure modes including alignment, the quantitative beam assessment device may also provide confirmation of alignment.

In some instances, the control unit 620 may determine whether components of the optical box 20 are within specification and/or an acceptable deviation from specification as discussed above.

In some embodiments, the control unit 620 can be further configured to issue an alert and/or notification of the optical box 20 passing the testing, identified failure modes for the optical box 20, and/or identified required actions. For example, the control unit 620 may issue an alert and or notification that components are outside of specification, are damaged, need to be replaced or repaired, and/or need to be cleaned. In some embodiments, the control unit 620 may display the alert and/or notification on the display 615. In some embodiments, the control unit 620 may display additional information related to the optical box 20 and/or failure modes including but not limited to determined measurements (e.g., misalignment distance and/or energy level) and raw images from the camera.

The devices, systems, and methods as described herein are not intended to be limited in terms of the particular embodiments described, which are intended only as illustrations of various features. Many modifications and variations to the devices, systems, and methods can be made without departing from their spirit and scope, as will be apparent to those skilled in the art.

While the method 700 is described as an exemplary testing process, it should be understood that steps of the method 700 may be omitted and/or may be performed separate from one another. For example, the qualitative beam assessment device and associated steps of the method 700 may be used and performed separately from the quantitative beam assessment device and associated steps of the method 700.

In some embodiments, the qualitative beam assessment device 605 may additionally provide information related to beam energy (i.e., quantitative). For example, the images recorded by the camera along with raw data from the camera may be used to calculate an energy level of the beam. To calculate the energy level, it may be necessary to know a loss on the attenuator of the qualitative beam assessment device 605, thereby enabling calculation of the energy level of the beam based on the calculated energy reaching the camera. In such embodiments, the quantitative beam assessment device 610 may be omitted from the system 600 and the steps associated with the quantitative beam assessment device 610 may be omitted from the method 700. Instead, the control unit 615 may calculate the energy level using image processing algorithms and/or machine learning algorithms to determine 730 a quantitative condition of the beam.

In additional embodiments, an energy distribution across the beam profile can be analyzed by performing image processing. In embodiments where the camera collects images, the color distribution of the beam profile within the images may be indicative of the intensity of the beam at each point, thereby indicating intactness and/or damage of the MLAM 14 and/or other components of the optical box 20.

It should be understood that the energy level of the beam from the optical box 20 may be reduced with respect to the clinical use range, (e.g., about 50 $mJ/mm^2$ to about 60 $mJ/mm^2$) for performing testing according to the method 700 as disclosed herein. Accordingly, the testing may be performed using a beam of about 1 $mJ/mm^2$, about 5 $mJ/mm^2$, about 10 $mJ/mm^2$, about 20 $mJ/mm^2$, about 25 $mJ/mm^2$, greater than about 25 $mJ/mm^2$, or individual values or ranges therebetween. This may be advantageous because the lower energies reduce the risk of damage to the qualitative beam assessment device 605 without altering the beam profile in a material fashion. Nonetheless, in some embodiments, energy levels in the clinical use range (e.g., about $mJ/mm^2$ to about 50 $mJ/mm^2$) may be utilized for testing with appropriate modifications to the method 700 as would be apparent to a person having an ordinary level of skill in the art. For example, the qualitative beam assessment device 605 may comprise an additional attenuator configured to reduce the energy level of the beam reaching the camera, thereby reducing the risk of damage to the camera.

It should be understood that while the systems and methods herein are generally described for use with a hybrid catheter, the systems and methods could also be utilized with any catheter that includes optical fibers for delivering laser energy.

While the systems and methods herein are generally described for use in testing an ablation system especially in the field (e.g., at a hospital or in an office-based lab setting), it should be understood that the systems and methods may be adapted for use in a manufacturing and/or off-site repair setting.

In some embodiments, the systems and methods herein may be utilized in a quality assurance procedure during or after manufacturing of an optical box. For example, the system 600 and/or the method 700 may be used in a similar manner as performed in the field, i.e., using the qualitative beam assessment device and/or quantitative beam assessment device to identify a root cause of energy drift and/or required repairs to rectify the identified issue.

In another example, the systems and methods herein may be utilized during initial manufacturing and/or repair of an optical box for aligning the MLAM and/or other optical components. Conventional methods require removal of the catheter connector and insertion of a CCD camera to align the MLAM until a proper beam shape is obtained. Thereafter, the catheter connector is re-attached to the optical box and a testing catheter is utilized therewith to sense the energy level obtained therethrough. The catheter connector may be adjusted until maximal energy is obtained therethrough. However, the system 600 and/or the method 700 may be adapted in order to simplify this procedure. For example, the qualitative beam assessment device may be used to align the MLAM by inserting the qualitative beam assessment device into the catheter connector (without the need to remove the catheter connector), and the signals obtained by the qualitative beam assessment device may be used to align the MLAM and the catheter connector as described herein. Accordingly, the assembly and/or repair process for the optical box may be simplified by using the systems and methods herein.

In another example, the systems and methods herein may be utilized during initial manufacturing and/or repair of an optical box for aligning the MLAM in the z-direction. Conventional methods are not effective for aligning the MLAM in the z-direction because energy levels are not particularly sensitive to the alignment in the z-direction such that it is difficult to detect misalignment using a testing catheter. However, the system 600 and/or the method 700 may adapted in order to align the MLAM in the z-direction. For example, the qualitative beam assessment device provides more accurate information related to the alignment in the z-direction based on the collected images and may thus more accurately diagnose alignment issues in the z-direction. Accordingly, the assembly and/or repair process for the optical box may be improved by using the systems and methods herein.

Data Processing Systems for Implementing Embodiments Herein

Figure 9:
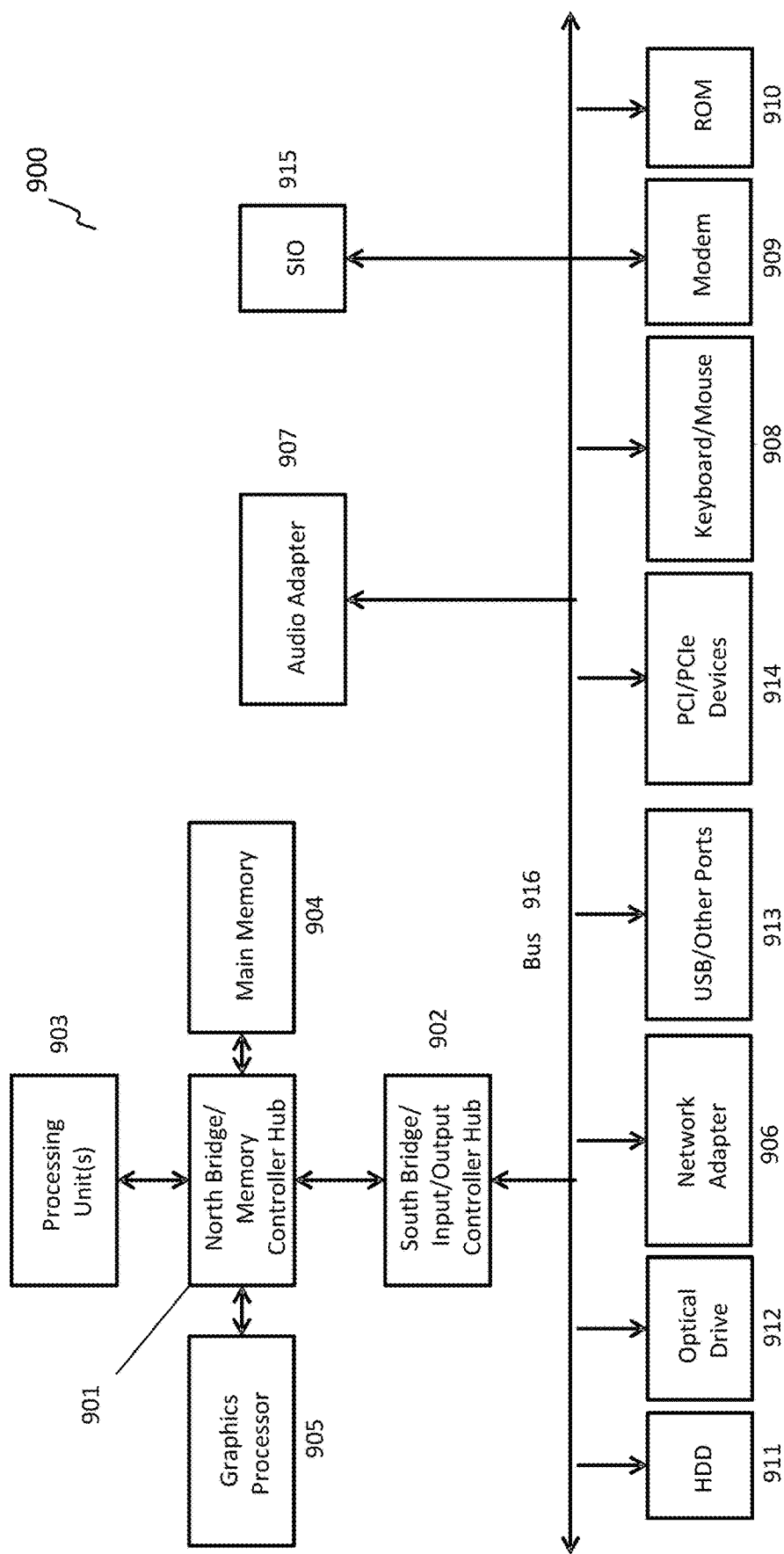
FIG. 9 illustrates a block diagram of an exemplary data processing system in which embodiments are implemented.

FIG. 9 illustrates a block diagram of an exemplary data processing system 900 in which embodiments are implemented. The data processing system 900 is an example of a computer, such as a server or client, in which computer usable code or instructions implementing the process for illustrative embodiments of the present invention are located. In some embodiments, the data processing system 900 may be a server computing device. For example, data processing system 900 can be implemented in a server or another similar computing device that is part of and/or operably connected to a system 600 as described above. The data processing system 900 can be configured to, for example, transmit and receive information related to a beam from the optical box 20 with the system 600.

In the depicted example, data processing system 900 can employ a hub architecture including a north bridge and memory controller hub (NB/MCH) 901 and south bridge and input/output (I/O) controller hub (SB/ICH) 902. Processing unit 903, main memory 904, and graphics processor 905 can be connected to the NB/MCH 901. Graphics processor 905 can be connected to the NB/MCH 901 through, for example, an accelerated graphics port (AGP).

In the depicted example, a network adapter 906 connects to the SB/ICH 902. An audio adapter 907, keyboard and mouse adapter 908, modem 909, read only memory (ROM) 910, hard disk drive (HDD) 911, optical drive (e.g., CD or DVD) 912, universal serial bus (USB) ports and other communication ports 913, and PCI/PCIe devices 914 may connect to the SB/ICH 902 through bus system 916. PCI/PCIe devices 914 may include Ethernet adapters, add-in cards, and PC cards for notebook computers. ROM 910 may be, for example, a flash basic input/output system (BIOS). The HDD 911 and optical drive 912 can use an integrated drive electronics (IDE) or serial advanced technology attachment (SATA) interface. A super I/O (SIO) device 915 can be connected to the SB/ICH 902.

An operating system can run on the processing unit 903. The operating system can coordinate and provide control of various components within the data processing system 900. As a client, the operating system can be a commercially available operating system. An object-oriented programming system, such as the Java™ programming system, may run in conjunction with the operating system and provide calls to the operating system from the object-oriented programs or applications executing on the data processing system 900. As a server, the data processing system 900 can be an IBM® eServer™ System® running the Advanced Interactive Executive operating system or the Linux operating system. The data processing system 900 can be a symmetric multiprocessor (SMP) system that can include a plurality of processors in the processing unit 903. Alternatively, a single processor system may be employed.

Instructions for the operating system, the object-oriented programming system, and applications or programs are located on storage devices, such as the HDD 911, and are loaded into the main memory 904 for execution by the processing unit 903. The processes for embodiments described herein can be performed by the processing unit 903 using computer usable program code, which can be located in a memory such as, for example, main memory 904, ROM 910, or in one or more peripheral devices.

A bus system 916 can be comprised of one or more busses. The bus system 916 can be implemented using any type of communication fabric or architecture that can provide for a transfer of data between different components or devices attached to the fabric or architecture. A communication unit such as the modem 909 or the network adapter 906 can include one or more devices that can be used to transmit and receive data.

Those of ordinary skill in the art will appreciate that the hardware depicted in FIG. 9 may vary depending on the implementation. Other internal hardware or peripheral devices, such as flash memory, equivalent non-volatile memory, or optical disk drives may be used in addition to or in place of the hardware depicted. Moreover, the data processing system 900 can take the form of any of a number of different data processing systems, including but not limited to, client computing devices, server computing devices, tablet computers, laptop computers, telephone or other communication devices, personal digital assistants, and the like. Essentially, data processing system 900 can be any known or later developed data processing system without architectural limitation.

Although the present invention has been described in considerable detail with reference to certain preferred embodiments thereof, other versions are possible. Therefore, the spirit and scope of the appended claims should not be limited to the description and the preferred versions contained within this specification. Various aspects of the present invention will be illustrated with reference to the following non-limiting examples:

EXAMPLES

Example 1: Testing Misalignment of Optical Box

Methods. Images of the beam profile from the optical box 20 were collected by a camera such as the camera applied at the catheter connector 25 under various different alignment conditions to identify distinct features of each alignment condition.

Figure 10:
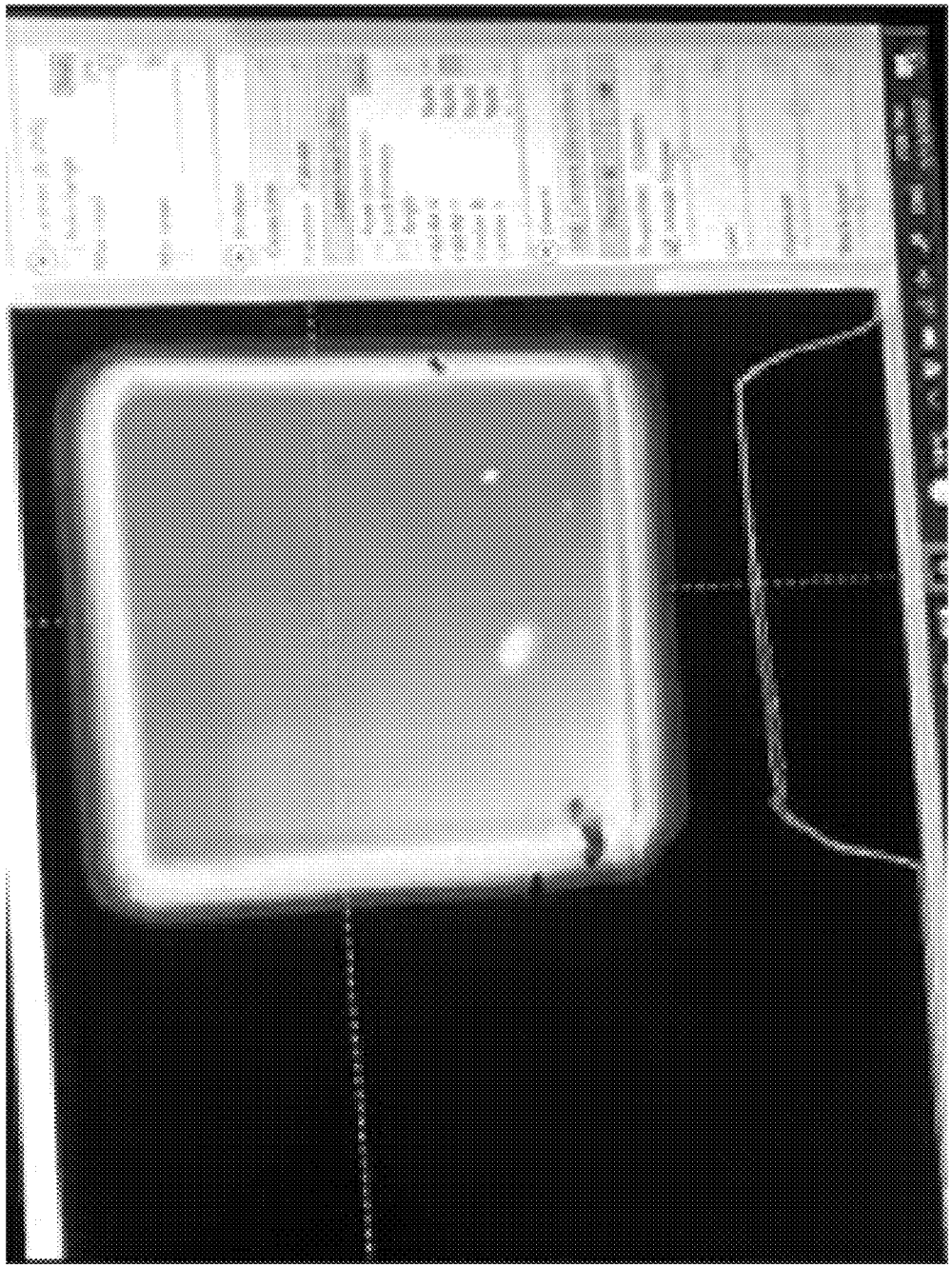
FIG. 10 depicts a reference beam profile of a beam within specification in accordance with an embodiment.

Results. FIG. 10 depicts a reference beam profile of a beam within specification. The profile and size of the beam are shown when the S and P spots at the entrance to the MLAM totally overlap.

Figure 11A:
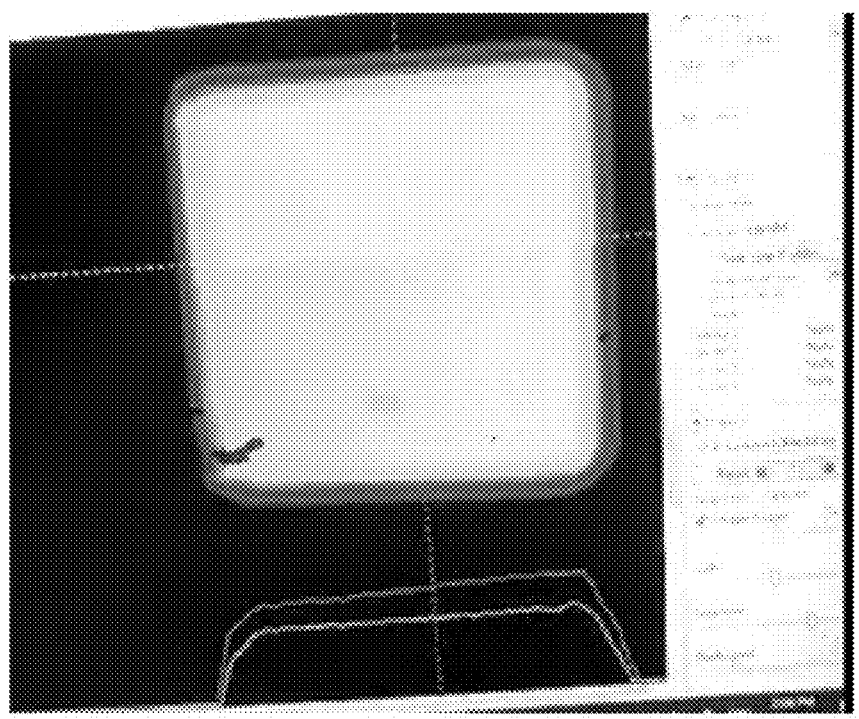
FIGS. 11A-11B depict beam profiles where the S spot deviates from the P spot by detuning a mirror in the y-direction in accordance with an embodiment.
Figure 11B:
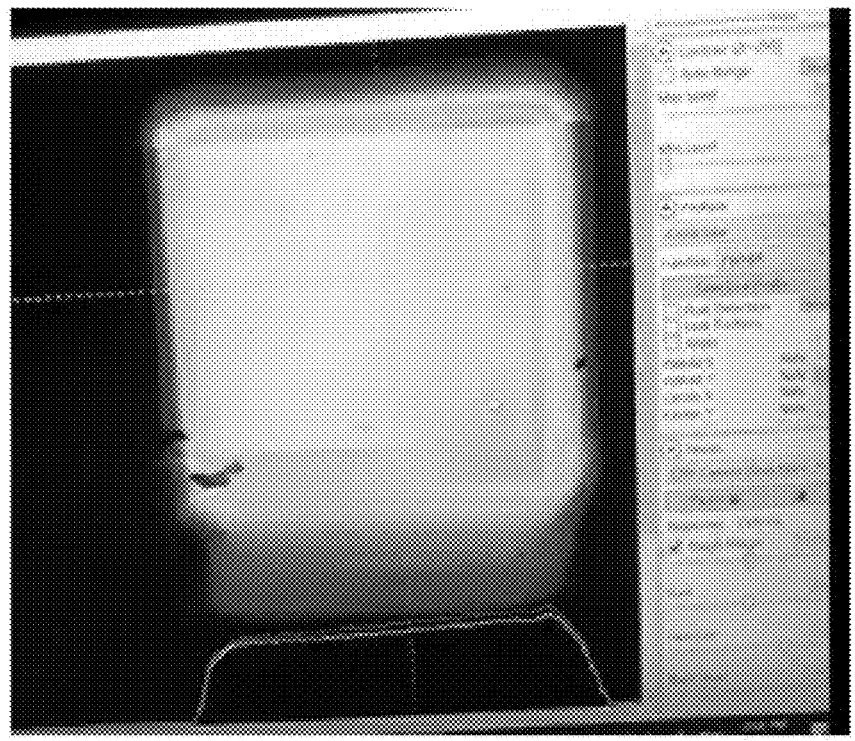

FIGS. 11A-11B depict beam profiles where the S spot deviates from the P spot by detuning of a mirror in the y-direction. FIG. 11A shows the profile and size of the beam when the S spot is shifted down. FIG. 11B shows the profile and size of the beam when the S spot is shifted up.

Figure 12A:
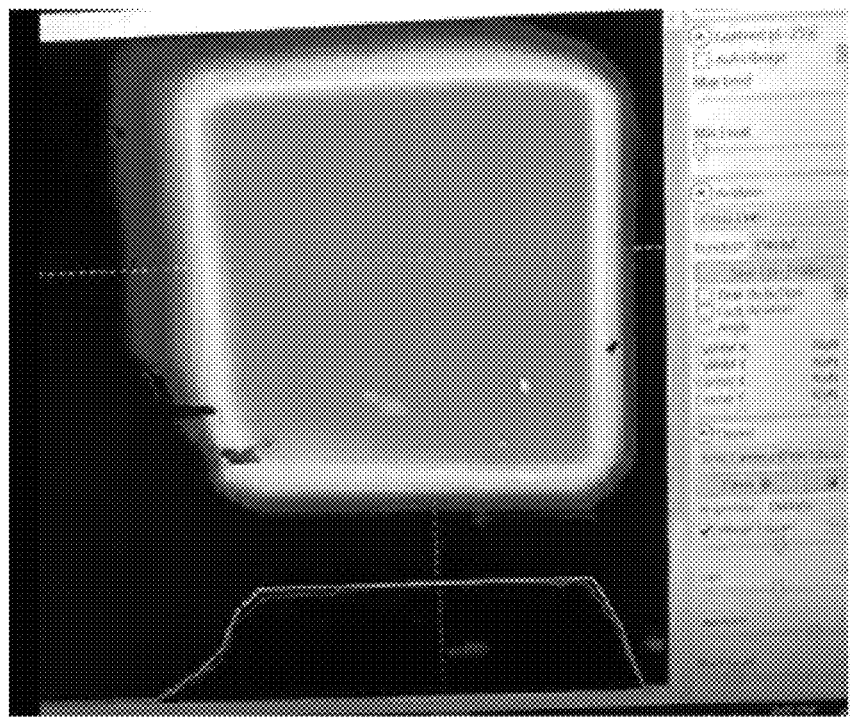
FIGS. 12A-12B depict beam profiles where the S spot deviates from the P spot by detuning a mirror in the x-direction in accordance with an embodiment.
Figure 12B:
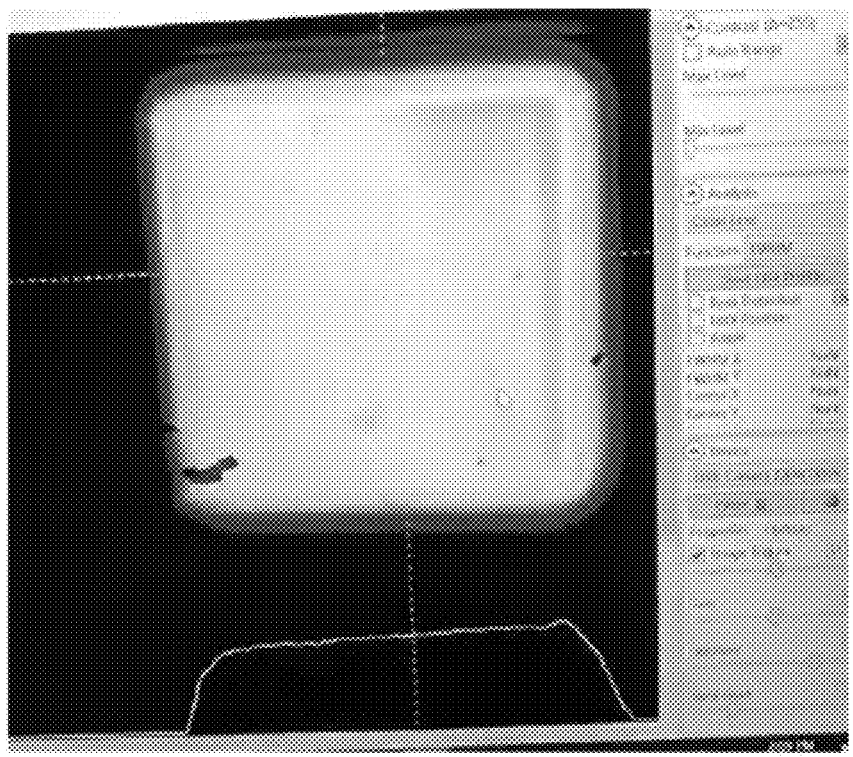

FIGS. 12A-12B depict beam profiles where the S spot deviates from the P spot by detuning of a mirror in the x-direction. FIG. 12A shows the profile and size of the beam when the S spot is shifted to the right. FIG. 12B shows the profile and size of the beam when the S spot is shifted to the left.

Figure 13A:
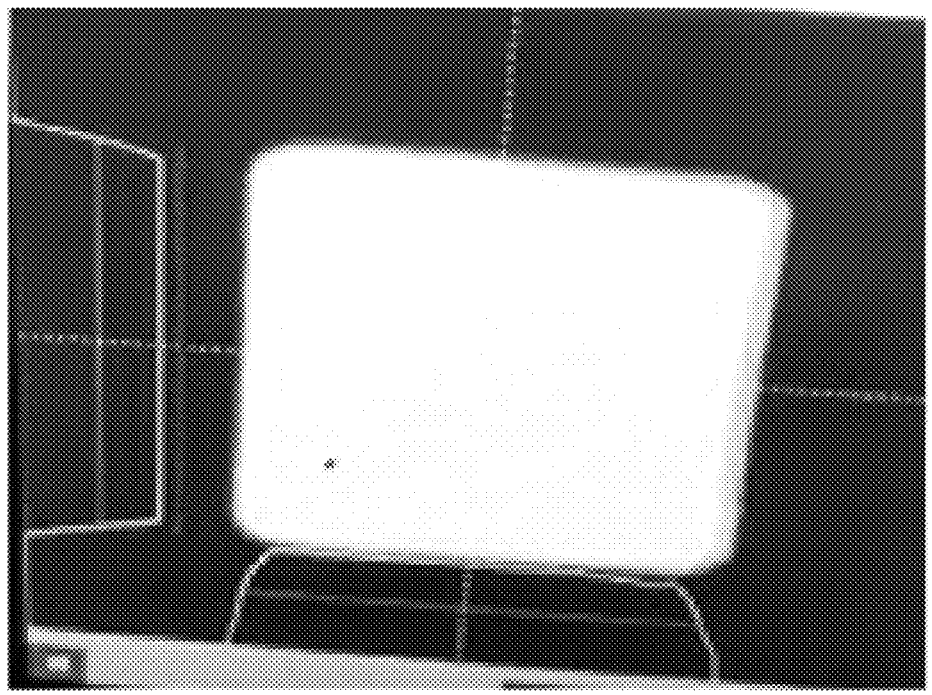
FIGS. 13A-13C depict beam profiles with and without local disturbance in accordance with an embodiment.
Figure 13B:
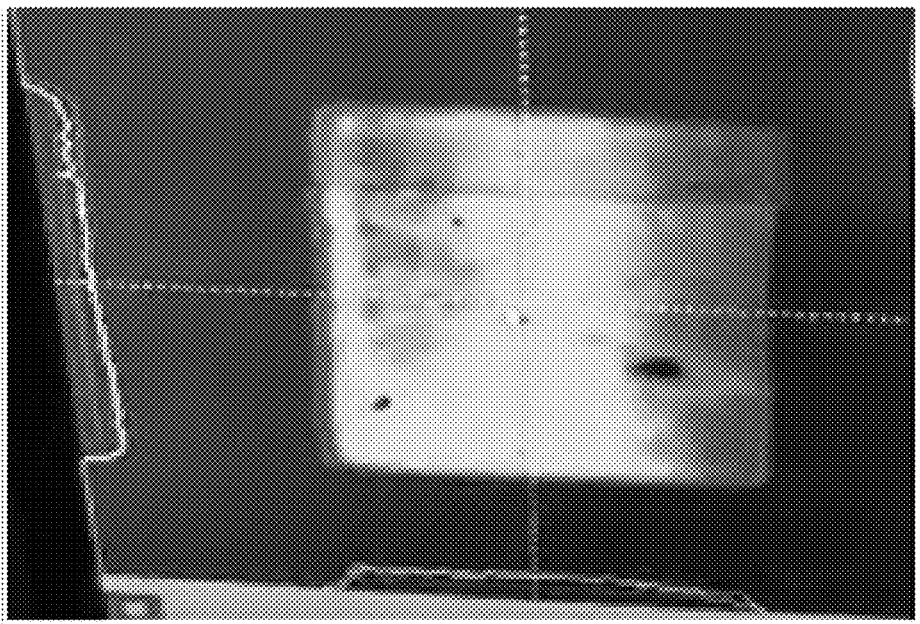
Figure 13C:
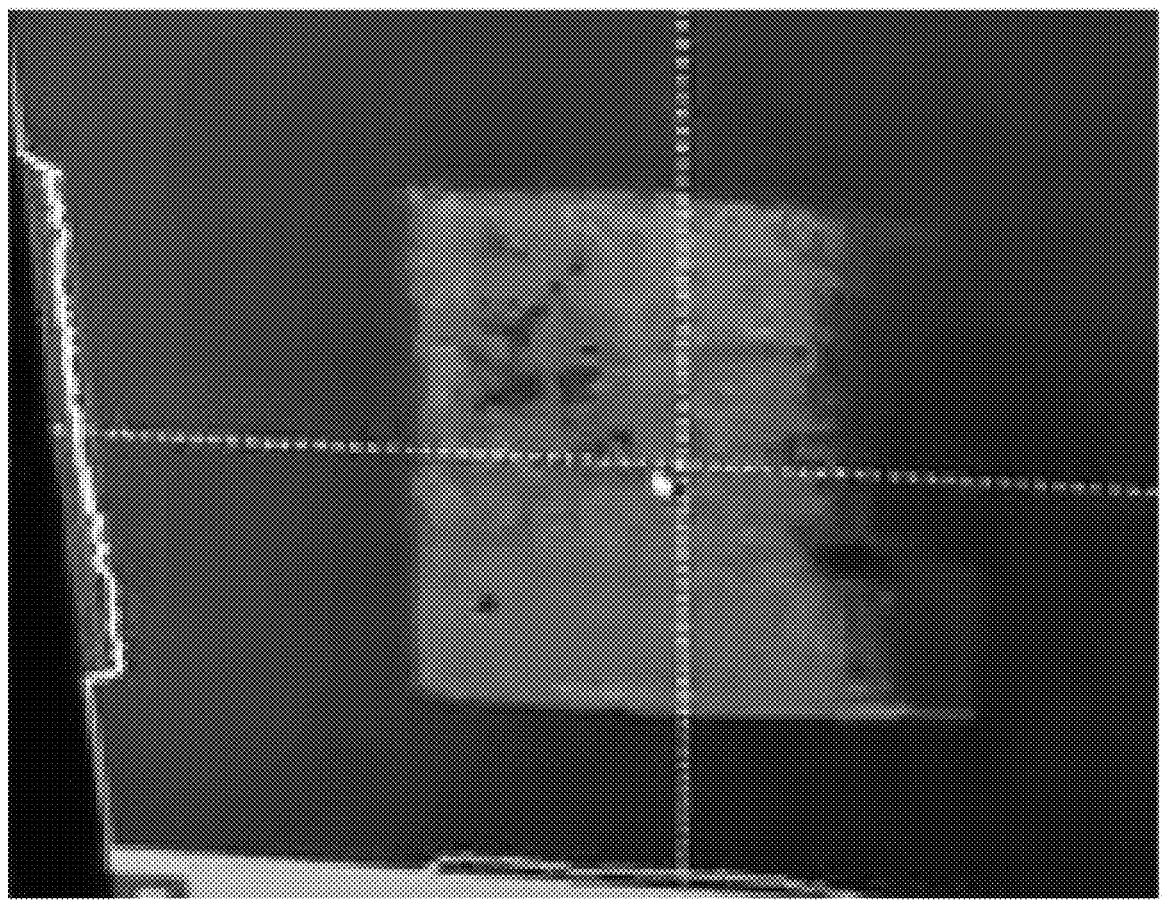

FIGS. 13A-13C depict beam profiles with and without local disturbance. FIG. 13A shows the profile of the beam when the image is not disturbed. FIG. 13B shows the profile of the beam when the image is partially disturbed. FIG. 13C shows the profile of the beam when the beam is partially blocked due to disturbance. As shown, when blocking the S spot, no image appears on the screen.

Figure 14A:
FIGS. 14A-14C depict beam profiles comparing an S spot deviation from the P spot by detuning a mirror in the y- or x-direction in accordance with an embodiment.
Figure 14B:
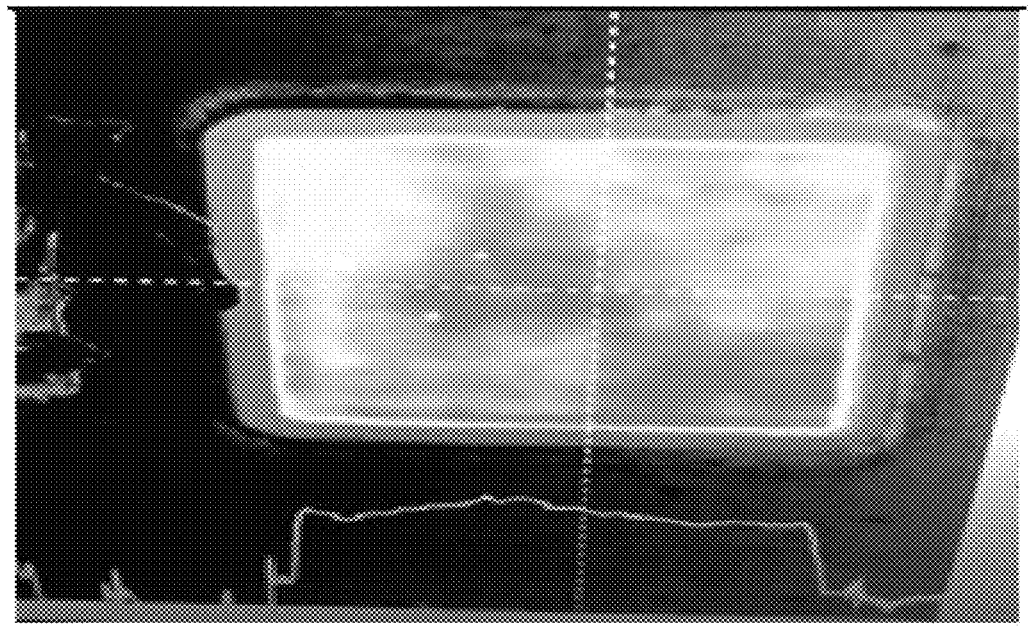
Figure 14C:
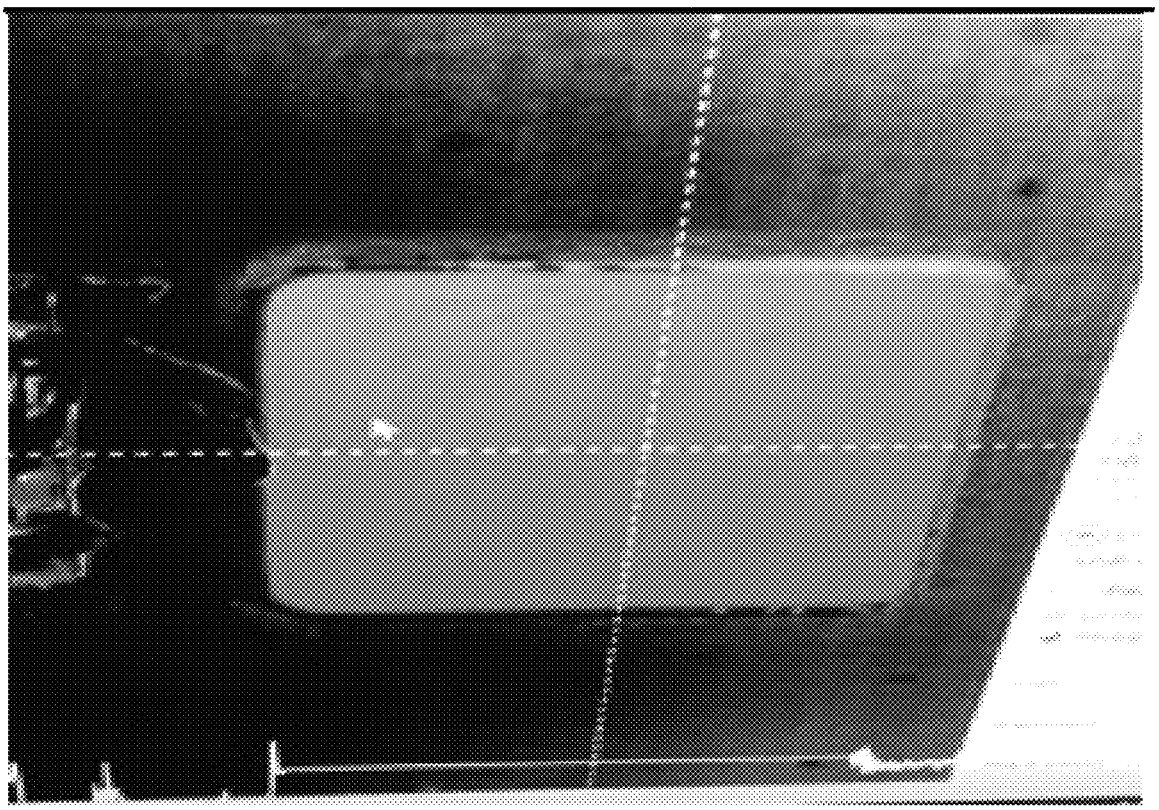

FIGS. 14A-14C depict beam profiles comparing S spot deviation from the P spot by detuning of a mirror in the y- or x-directions. FIG. 14A depicts the S and P spots at the entrance to the MLAM when they totally overlap. FIG. 14B depicts the beam profile when the S and P spots totally overlap. FIG. 14C depicts the beam profile when the S beam is blocked. As shown, no image appears when the S beam is blocked.

Figure 15A:
FIGS. 15A-15C depict beam profiles comparing an S spot deviation from the P spot by detuning a mirror in the y- or x-direction in accordance with an embodiment.
Figure 15B:
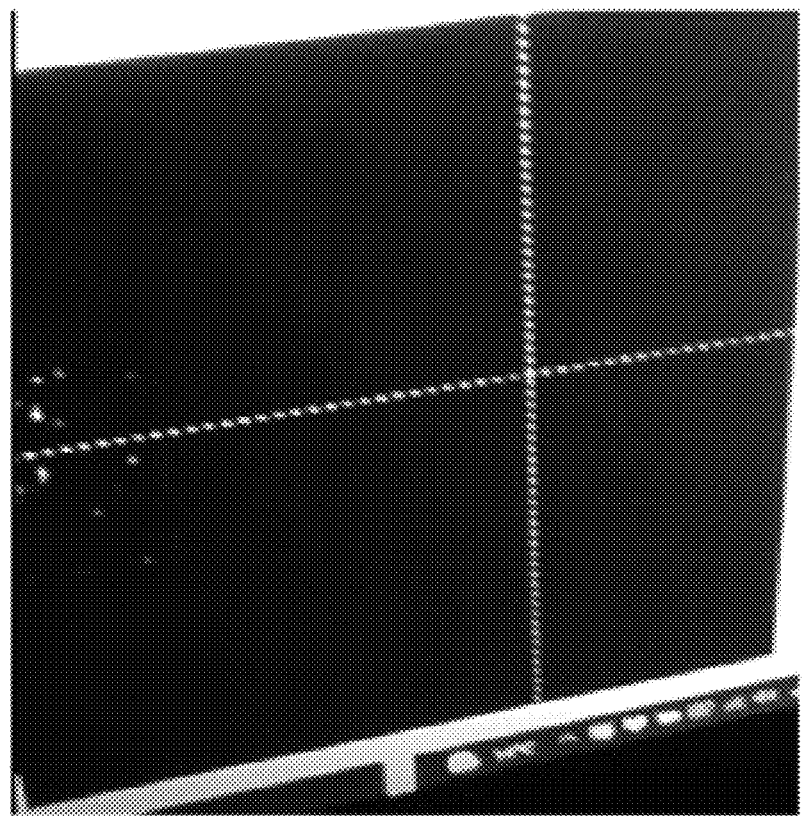
Figure 15C:
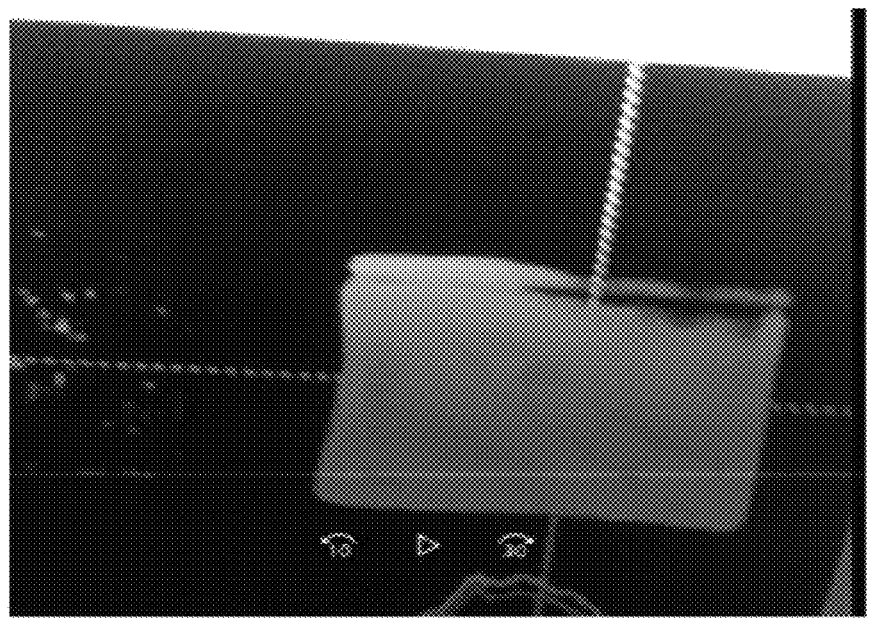

FIGS. 15A-15C depict beam profiles comparing S spot deviation from the P spot by detuning of a mirror in the y- or x-directions. FIG. 15A-15C depict different conditions of deviation of the S and P spots. As shown in FIG. 15B, no image appears when the S spot significantly deviates from the P spot. Further, as shown in FIG. 15C, when the S spot is a bit closer to the P spot at the entrance to the MLAM, a partial beam profile appears (e.g., about half).

Figure 16B:
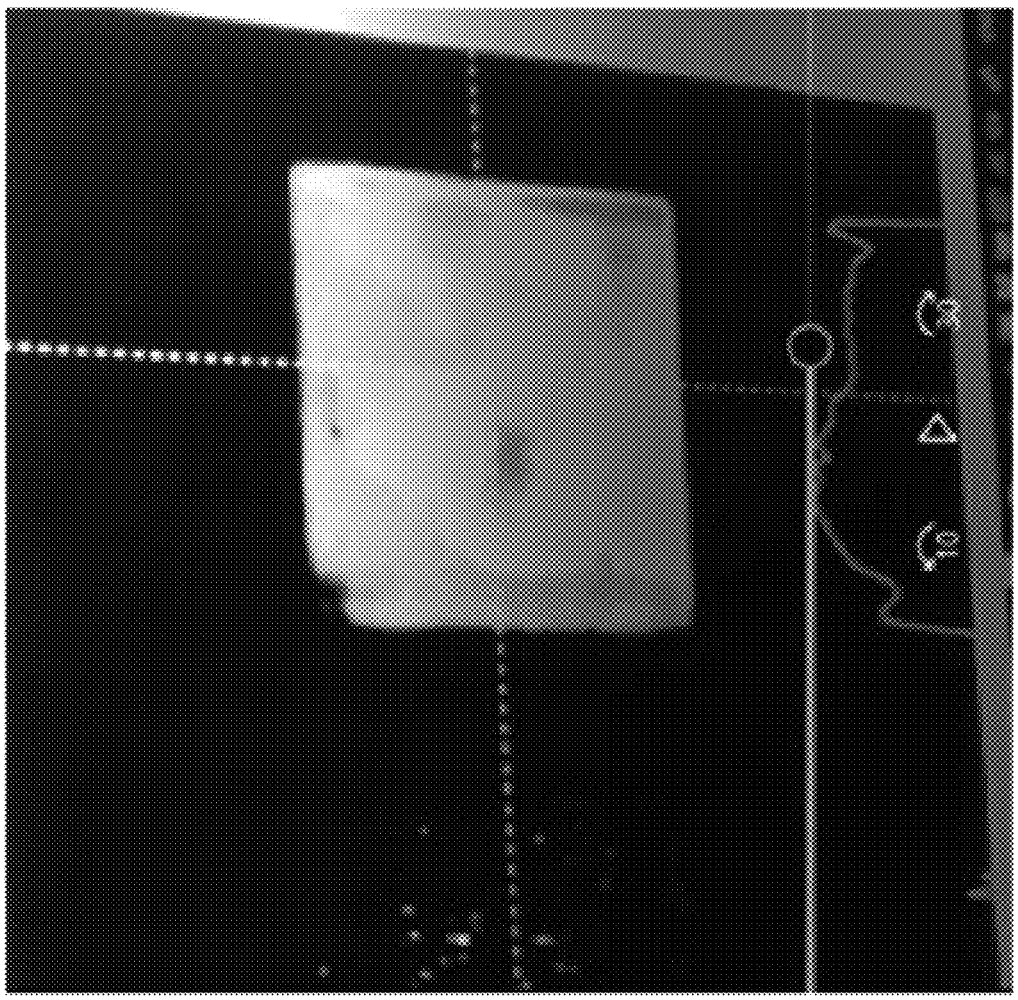
FIGS. 16A-16B depict beam profiles comparing an S spot shifted from the P spot in accordance with an embodiment.
Figure 16A:
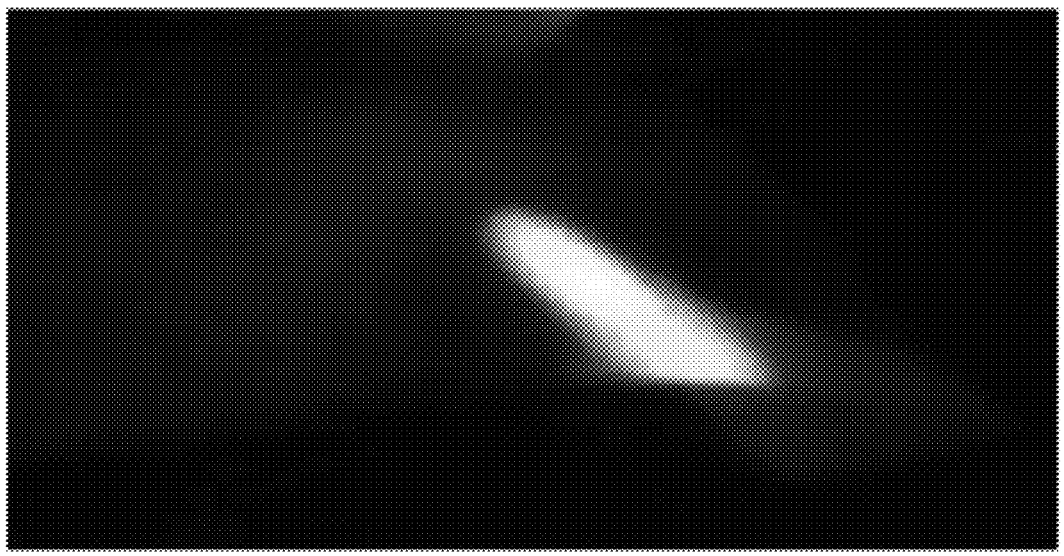

FIGS. 16A-16B depict beam profiles comparing S spot shifted from the P spot. FIG. 16A depicts the S spot has shifted to the right. FIG. 16B depicts the beam profile under the shifted condition, wherein the image appears less sharp.

Figure 17A:
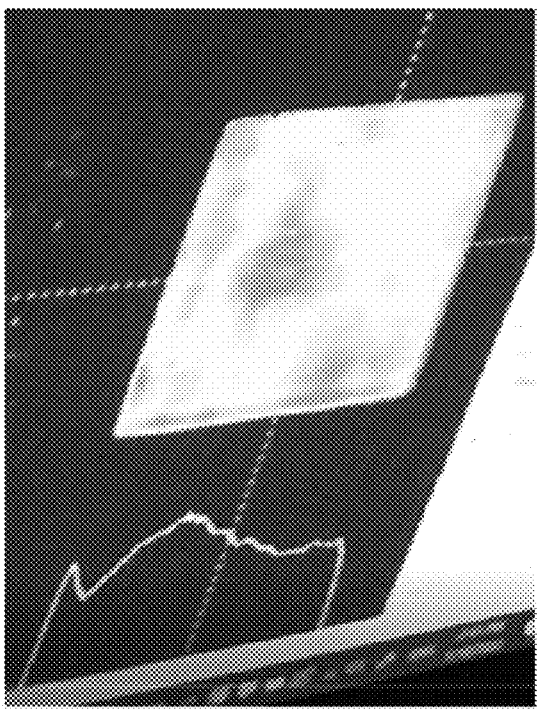
FIGS. 17A-17D depict beam profiles where the connector (along with the camera) is shifted from the focal plane in accordance with an embodiment.
Figure 17B:
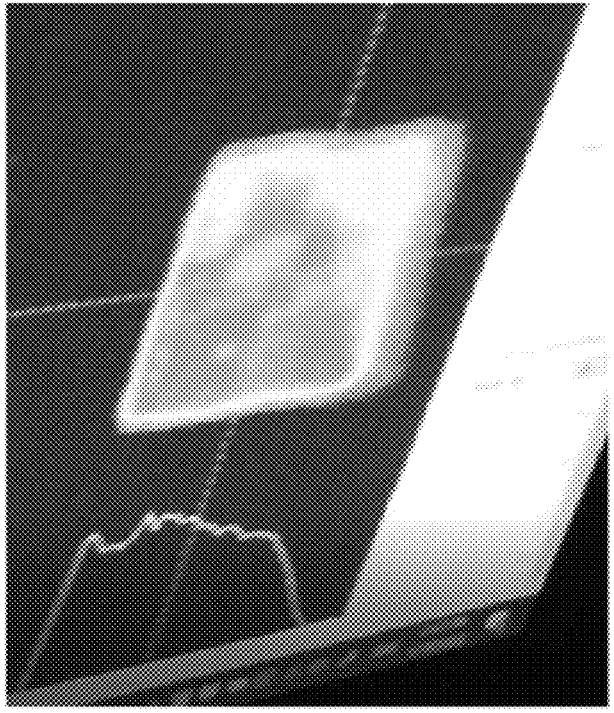
Figure 17C:
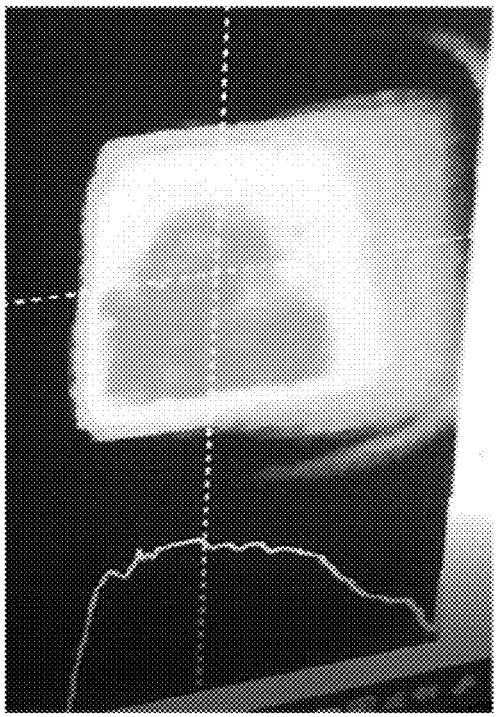
Figure 17D:
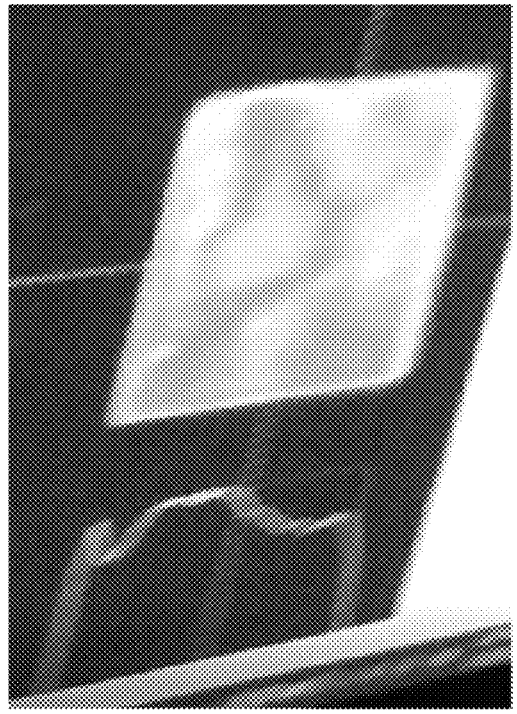

FIGS. 17A-17D depict beam profiles where the connector housing (along with the camera) is shifted from the focal plane. FIG. 17A depicts the beam profile when the connector is aligned at the focal plane. FIG. 17B depicts the beam profile when the connector has a moderate shift from the focal plane. FIG. 17C depicts the beam profile when the connector has a severe shift from the focal plane. FIG. 17D depicts the beam profile when the connector is back in the focal plane.

FIGS. 18A-18D depict beam profiles where the overlapping P+S beam is shifted by detuning a final mirror of the optical box (also referred to as a 2" mirror herein) in the y- and x-directions. The final mirror of the optical box may, for example, be located between the second polarization beam splitter 29 and the coupling lens 12 of the optical box 20 as shown in FIG. 2. Although the final mirror is not depicted in FIG. 2, it should be understood that the final mirror may be arranged as the last mirror through which the beam passes prior to reaching the coupling lens 12. For example, the final mirror may be the last mirror of the beam pass. FIG. 18A depicts the beam profile when the final mirror is shifted in the y-direction. As shown, the beam profile is divided in two parts in the y-direction. FIG. 18B depicts the beam profile when the final mirror is shifted in the x-direction. As shown, the beam profile is divided in two parts in the x-direction. FIG. 18C depicts the beam profile when the final mirror is shifted in the x-direction until partial clipping occurs. FIG. 18D depicts the beam profile when the 2" mirror is in the unshifted state.

Discussion. As shown in FIGS. 10-18, the camera jig responded to shifts of the S spot, the final mirror, shifts of the focal plane, and drop of the output energy as a result of partial beam clipping (i.e., where the full beam does not go through the aperture). When the S spot is shifted even partially out of the optical aperture, the intensity of the beam profile decreased dramatically until no appearance of the image resulted. Increasing shifts of the P+S overlapping beam by the final mirror results in hot spots in the beam profile, followed with extreme peaks and valleys, and ultimately no appearance of the image. Shifting the MLAM or the connector housing in the z-direction (focal plane shift) results in a less sharp (blurry) and wider (or narrower) image. The camera jig can indicate if the connector housing has been shifted, such that when the connector housing is aligned, the spot image will appear in the middle of the screen. When it is shifted in the x- and/or y-directions, the image will appear to the side of the screen.

The method can include at least observing a beam profile via the camera jig positioned in the plane of the optical fibers, e.g., positioned within the connector housing, and determining a failure mode within the optical box based on the observed beam profile. In some examples, if a near perfect square is observed, then there is no issue. If two slightly separated squares are observed, the S beam has likely moved. If the intensity of the beam is reduced, the beam is likely cut. Accordingly, in this experiment it is shown that the camera jig is capable of detecting shifts of the S beam, shifts of the final mirror, misalignments of the MLAM (e.g., angular misalignment, spatial shifts, and focal plane shifts), misalignments of the connector housing, and reduction of the laser beam intensity due to local disturbance of the beam.

In some instances, the camera jig can use firmware to provide raw data, which can be used with image processing to detect defects in the lens array or other issues with optics.

Example 2: Energy Reduction from Optical Box to Camera

Figure 19A:
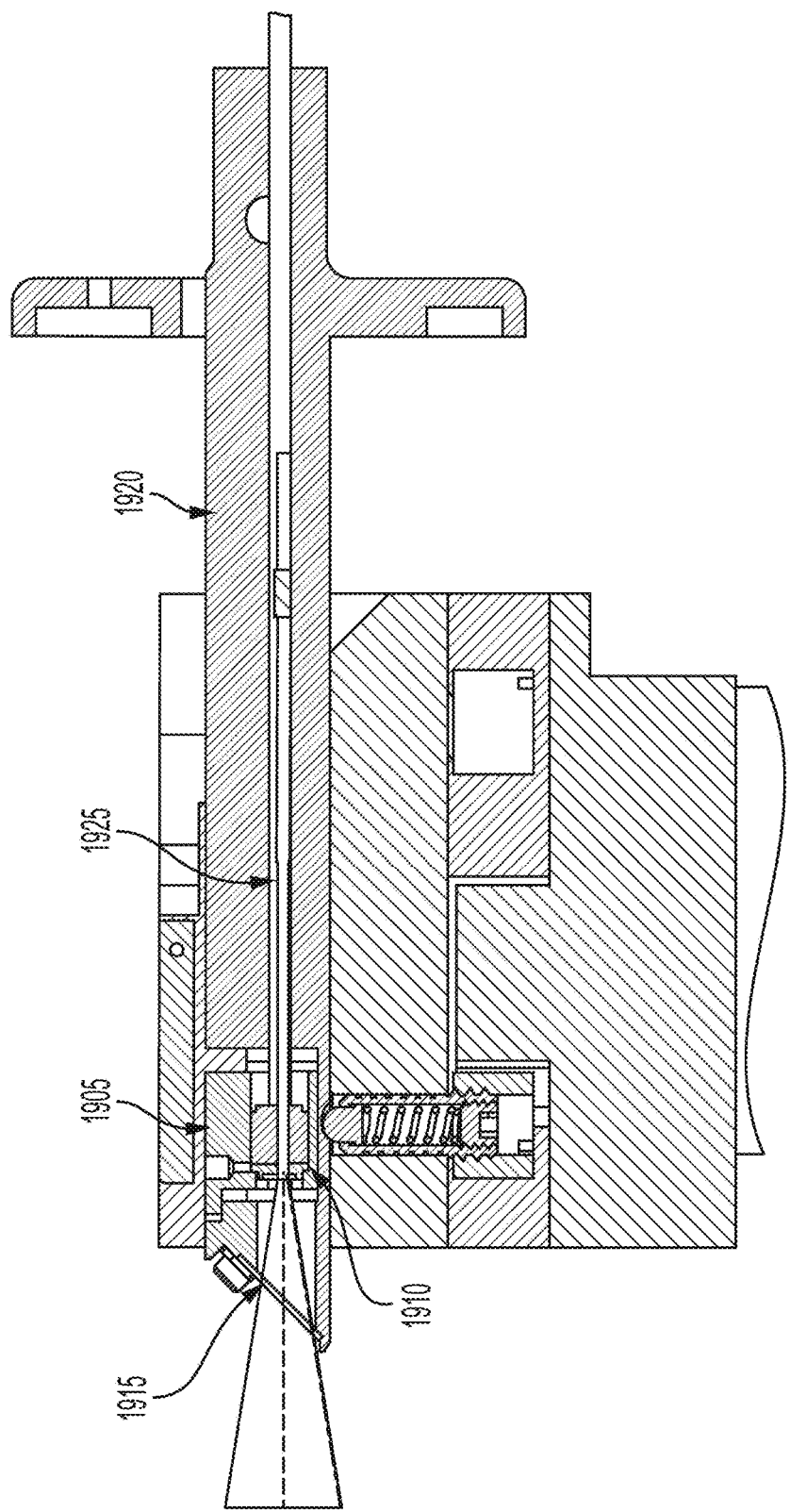
FIG. 19A depicts a cross-sectional side view of the connector housing with the camera jig inserted therein, and showing the mirror/beam separator with respect to the camera in accordance with an embodiment.

Methods. The energy reduction of the beam from the optical box to the camera was tested under different conditions (i.e., mirrors and/or splitters) to determine a configuration that is safe for the camera. FIG. 19A depicts a cross-sectional side view of the connector housing 25 with the camera jig inserted therein receiving a beam 30, and showing the mirror/beam separator with respect to the camera. As shown, the camera jig may include a camera housing 1905, a camera 1910, a mirror/beam separator 1915, a handle 1920, and a fiber optic cable 1925. FIG. 19B depicts a cross-sectional top-down view of the connector housing with the camera jig inserted therein, and showing the mirror/beam separator with respect to the camera.

Results. The energy density on the beam splitter was calculated. The energy density is low (<1 J/cm$^2$); therefore, a standard mirror can be used. The angle of the mirror may be approximately 30 degrees around the x-axis in order to allow a larger beam size on the optical box cover.

An additional angle of 45 degrees may be applied around the z-axis to allow equal transmittance of the S and P beams. In addition, a neutral density and/or absorption-based filter may be included in the beam path after the splitter to avoid saturation of the camera.

In one embodiment, the mirror diameter is about 10 mm and the thickness is about mm. In some embodiments, the mirror can be composed of fused silica. Additionally, in some embodiments, the mirror can have a coating on one or both sides configured to reduce the amount of energy to the camera so the camera will not be saturated.

A mini USB camera, integrated in the current catheter connector, was successfully tested. The beam shape analysis can also be performed in low OSC/AMP levels, so an option is to reduce the laser energy level (can also be done by RFID tag). Examples of cameras that can be used include FXD, XD Series cameras (e.g., Model Nos. XD-B44106R, XD844106R-XD-B41106RL-65) distributed by Misumi.

In the above detailed description, reference is made to the accompanying drawings, which form a part hereof. In the drawings, similar symbols typically identify similar components, unless context dictates otherwise. The illustrative embodiments described in the present disclosure are not meant to be limiting. Other embodiments may be used, and other changes may be made, without departing from the spirit or scope of the subject matter presented herein. It will be readily understood that various features of the present disclosure, as generally described herein, and illustrated in the Figures, can be arranged, substituted, combined, separated, and designed in a wide variety of different configurations, all of which are explicitly contemplated herein.

The present disclosure is not to be limited in terms of the particular embodiments described in this application, which are intended as illustrations of various features. Instead, this application is intended to cover any variations, uses, or adaptations of the present teachings and use its general principles. Further, this application is intended to cover such departures from the present disclosure as come within known or customary practice in the art to which these teachings pertain. Many modifications and variations can be made to the particular embodiments described without departing from the spirit and scope of the present disclosure as will be apparent to those skilled in the art. Functionally equivalent methods and apparatuses within the scope of the disclosure, in addition to those enumerated herein, will be apparent to those skilled in the art from the foregoing descriptions. It is to be understood that this disclosure is not limited to particular methods, reagents, compounds, compositions or biological systems, which can, of course, vary. It is also to be understood that the terminology used herein is for the purpose of describing particular embodiments only, and is not intended to be limiting.

Various of the above-disclosed and other features and functions, or alternatives thereof, may be combined into many other different systems or applications. Various presently unforeseen or unanticipated alternatives, modifications, variations or improvements therein may be subsequently made by those skilled in the art, each of which is also intended to be encompassed by the disclosed embodiments.

What is claimed is:

1. A qualitative beam assessment device configured to interface with an ablation system comprising an optical box and a catheter connector, the qualitative beam assessment device comprising:
    a housing sized and configured to be received by the catheter connector;
    a camera coupled to the housing and configured to record an image of a beam emitted by the optical box, wherein the camera is arranged and configured to align with a focal plane of the optical box when the housing is received by the catheter connector; and
    a communication component in electrical communication with the camera, wherein the communication component is configured to transmit the recorded image from the camera to a processor.

2. The qualitative beam assessment device of claim 1, further comprising an attenuator arranged and configured to attenuate the beam emitted by the optical box before reaching the camera.

3. The qualitative beam assessment device of claim 1, wherein the housing has a diameter of about 18 mm at an insertion portion configured to be received by the catheter connector.

4. The qualitative beam assessment device of claim 1, wherein a portion of the camera is optically exposed within the focal plane of the optical box when the housing is received by the catheter connector.

5. The qualitative beam assessment device of claim 1, further comprising an RFID chip configured to communicate with the ablation system, wherein the RFID chip is configured to instruct the ablation system to reduce an energy density of the beam emitted from the optical box.

6. A quantitative beam assessment device configured to interface with an ablation system comprising an optical box and a catheter connector, the qualitative beam assessment device comprising:
    a housing sized and configured to be received by the catheter connector;
    an energy sensor coupled to the housing and configured to measure an energy of a beam emitted by the optical box;
    a guiding component coupled to the housing and configured to direct the beam emitted by the optical box to the energy sensor, wherein the guiding component is arranged and configured to align with a focal plane of the optical box when the housing is received by the catheter connector; and
    a communication component in electrical communication with the energy sensor, wherein the communication component is configured to transmit the measurement from the energy sensor to a processor.

7. The quantitative beam assessment device of claim 6, wherein the energy sensor comprises a thermoelectric cooler.

8. The quantitative beam assessment device of claim 6, wherein the guiding component is selected from the group consisting of a shutter, a waveguide, and a square core fiber.

9. The quantitative beam assessment device of claim 6, wherein the housing has a diameter of about 18 mm at an insertion portion configured to be received by the catheter connector.

10. The quantitative beam assessment device of claim 6, wherein a portion of the energy sensor is optically exposed within the focal plane of the optical box when the housing is received by the catheter connector.

11. A system for testing an ablation system comprising an optical box and a catheter connector, the system comprising:
    a qualitative beam assessment device comprising a first housing sized and configured to be received by the catheter connector and a camera configured to record one or more signals related to a beam profile of a beam emitted by the optical box, wherein the camera is arranged and configured to align with a focal plane of the optical box when the housing is received by the catheter connector;
    a quantitative beam assessment device comprising a second housing sized and configured to be received by the catheter connector, an energy sensor coupled to the housing and configured to measure a beam energy of the beam emitted by the optical box, and a guiding component coupled to the housing and configured to direct the beam emitted by the optical box to the energy sensor, wherein the guiding component is arranged and configured to align with the focal plane of the optical box when the housing is received by the catheter connector;
    a processor configured to electrically communicate with each of the qualitative beam assessment device and the quantitative beam assessment device; and
    a non-transitory, computer-readable medium storing instructions that, when executed, cause the processor to:
        receive, from the qualitative beam assessment device, the one or more signals related to the beam profile,
        determine, based on the one or more signals related to the beam profile, a qualitative condition of the beam,
        receive, from the quantitative beam assessment device, the one or more signals related to the beam energy, and
        determine, based on the one or more signals related to the beam energy, a quantitative condition of the beam.

12. The system of claim 11, wherein the qualitative beam assessment device further comprises an attenuator arranged and configured to attenuate the beam emitted by the optical box before reaching the camera.

13. The system of claim 11, wherein each of the first housing and the second housing has a diameter of about 18 mm at an insertion portion configured to be received by the catheter connector.

14. The system of claim 11, wherein the first housing and the second housing are each configured to be selectively received at a first portion of the catheter connector.

15. The system of claim 11, further comprising a display device in electrical communication with the processor.

16. The system of claim 15, wherein the instructions, when executed, further cause the processor to display at least one of the determined qualitative condition and the determined quantitative condition on the display device.

17. The system of claim 11, wherein the qualitative condition comprises a failure mode of the ablation system.

18. The system of claim 17, wherein the failure mode comprises misalignment of the beam.

19. The system of claim 18, wherein the misalignment of the beam is selected from the group consisting of:
    blocking of an S-polarized beam of the beam from entering an optical element of the optical box, wherein the beam comprises an S-polarized beam and a P-polarized beam;
    misalignment of a mirror of the optical box;
    shifting of the S-beam;
    misalignment in the Z-direction from a focal point of the optical box; and
    misalignment of the catheter connector.

20. The system of claim 17, wherein the failure mode is selected from the group consisting of misalignment of the beam, damage to the an optical element, failure of a laser of the ablation system, failure of a sensor of the ablation system, cutting of the beam, misalignment of a P-beam and an S-beam of the beam, a dirty optical element of the optical box, misalignment of the catheter connector in the X-Y plane, misalignment of the catheter connector in the Z-direction, low overall energy, and improper energy distribution.

* * * * *